US011129790B2

(12) United States Patent
Zhou et al.

(10) Patent No.: US 11,129,790 B2
(45) Date of Patent: Sep. 28, 2021

(54) CHEMO-ENZYMATIC SITE-SPECIFIC MODIFICATION OF PEPTIDES AND PROTEINS TO FORM CLEAVABLE CONJUGATES

(71) Applicant: Northeastern University, Boston, MA (US)

(72) Inventors: Zhaohui Sunny Zhou, Wellesley, MA (US); George O'Doherty, Boston, MA (US); Shanshan Liu, Boston, MA (US); Kevin Ryan Moulton, Brighton, MA (US); Lincoln Ombelets, Boston, MA (US); Amissi Sadiki, Boston, MA (US)

(73) Assignee: Northeastern University, Boston, MA (US)

(*) Notice: Subject to any disclaimer, the term of this patent is extended or adjusted under 35 U.S.C. 154(b) by 31 days.

(21) Appl. No.: 15/985,494

(22) Filed: May 21, 2018

(65) Prior Publication Data
US 2018/0369131 A1    Dec. 27, 2018

Related U.S. Application Data

(60) Provisional application No. 62/508,999, filed on May 19, 2017, provisional application No. 62/664,659, filed on Apr. 30, 2018.

(51) Int. Cl.
A61K 9/00      (2006.01)
C12P 21/06     (2006.01)
C07K 1/13      (2006.01)
C12N 9/10      (2006.01)

(52) U.S. Cl.
CPC .............. A61K 9/0002 (2013.01); C07K 1/13 (2013.01); C12N 9/1044 (2013.01); C12P 21/06 (2013.01); C12Y 203/02013 (2013.01)

(58) Field of Classification Search
None
See application file for complete search history.

(56) References Cited

U.S. PATENT DOCUMENTS

| | | |
|---|---|---|
| 7,172,877 B2 | 2/2007 | Ting |
| 7,196,180 B2 | 3/2007 | Aeschlimann et al. |
| 7,955,377 B2 | 6/2011 | Melsheimer |
| 8,137,925 B2 | 3/2012 | Ting et al. |
| 8,871,456 B2 | 10/2014 | Ting et al. |
| 8,946,197 B2 | 2/2015 | Dominguez et al. |
| 9,090,937 B2 | 7/2015 | Marionnet et al. |
| 9,284,541 B2 | 3/2016 | Ting et al. |
| 9,347,037 B2 | 5/2016 | Masutani et al. |
| 9,474,885 B2 | 10/2016 | Kline et al. |
| 9,764,120 B2 | 9/2017 | Cline et al. |
| 2003/0095993 A1 | 5/2003 | Bentz et al. |
| 2004/0209317 A1 | 10/2004 | Ting |
| 2005/0233389 A1 | 10/2005 | Ting et al. |
| 2007/0149441 A1 | 6/2007 | Aeschlimann et al. |
| 2009/0149631 A1 | 6/2009 | Ting et al. |
| 2010/0261652 A1 | 10/2010 | Wang et al. |
| 2014/0199325 A1* | 7/2014 | Collighan .............. A61P 35/00 424/158.1 |
| 2015/0125904 A1 | 5/2015 | Ting et al. |
| 2015/0165064 A1* | 6/2015 | Bregeon ................ A61P 35/02 424/181.1 |
| 2015/0238631 A1 | 8/2015 | Kim et al. |
| 2016/0130729 A1 | 5/2016 | Stoessel et al. |
| 2016/0143720 A1 | 5/2016 | Matheny et al. |
| 2016/0144072 A1 | 5/2016 | Matheny et al. |
| 2016/0144076 A1 | 5/2016 | Matheny et al. |
| 2016/0279283 A1 | 9/2016 | Griffin et al. |
| 2016/0289627 A1 | 10/2016 | Masutani et al. |
| 2017/0368224 A1 | 12/2017 | Griffin et al. |
| 2018/0001066 A1 | 1/2018 | Kline et al. |

FOREIGN PATENT DOCUMENTS

| | | |
|---|---|---|
| EP | 1115433 B1 | 12/2004 |
| EP | 1645907 A1 | 4/2006 |
| EP | 1757314 A1 | 2/2007 |
| EP | 3004434 B1 | 4/2016 |
| EP | 2473627 B1 | 12/2016 |
| JP | 2012520863 A | 9/2012 |
| JP | 2016517694 A | 6/2016 |
| WO | 2000016818 A1 | 3/2000 |
| WO | 2000052064 A1 | 9/2000 |
| WO | 2000058450 A1 | 10/2000 |
| WO | 2001054735 A2 | 8/2001 |
| WO | 2009064366 A2 | 5/2009 |

(Continued)

OTHER PUBLICATIONS

Gorman et al. J. Biol.Chem. (1980) 255(3): 1175-1180 (Year: 1980).*
Rachel et al. Chem. Comm. (Jan. 4, 2016) 52: 2541-2544 (Year: 2016).*
Gundersen et al. Appl. Microbiol. Biotechnol. (2014) 98: 219-230 (Year: 2015).*
Streitwieser et al. Intro. Organic Chem. (1981) (Macmillan Publishing: New York) pp. 697-702 (Year: 1981).*
Yang et al. Chem. Soc. Rev. (2014) 43: 6511-6526 (Year: 2014).*
Lee et al. J. Am. Chem. Soc. (2011) 133: 2331-2333 (Year: 2011).*
Endo et al. Angew. Chem. Int. Ed. (2004) 43: 5643-5645 (Year: 2004).*
Coussons et al. Biochem. J. (1991) 273: 73-78 (Year: 1991).*
Valdivia et al. J. Biotechnol. (2006) 122: 326-333 (Year: 2006).*
Villalonga et al. Biotecnol. Bioengineer. (2003) 81(6): 732-737 (Year: 2003).*

(Continued)

Primary Examiner — Susan M Hanley
(74) Attorney, Agent, or Firm — Verrill Dana, LLP

(57) ABSTRACT

A method is provided for reversibly modifying a protein or peptide on its glutamine residue(s) by performing a reaction, such as a transglutaminase-catalyzed reaction, between the protein or peptide and an amine-containing reagent, whereby the reagent is linked through its amine function to a side chain of the glutamine residue. Subjecting the modified protein to an appropriate stimulus regenerates the protein or peptide in its original form.

33 Claims, 16 Drawing Sheets
Specification includes a Sequence Listing.

(56) References Cited

FOREIGN PATENT DOCUMENTS

| | | | |
|---|---|---|---|
| WO | 2009094373 | A1 | 7/2009 |
| WO | 2010117947 | A2 | 10/2010 |
| WO | 2011060321 | A1 | 5/2011 |
| WO | 2013052851 | A9 | 4/2013 |
| WO | 2013148189 | A1 | 10/2013 |
| WO | 2014190443 | A1 | 12/2014 |
| WO | 2015057852 | A1 | 4/2015 |
| WO | 2016011387 | A1 | 1/2016 |
| WO | 2016013949 | A2 | 1/2016 |
| WO | 2016112388 | A1 | 7/2016 |
| WO | 2016168769 | A1 | 10/2016 |
| WO | 2017095806 | A1 | 6/2017 |
| WO | 2017190074 | A1 | 11/2017 |
| WO | 2018017657 | A1 | 1/2018 |

OTHER PUBLICATIONS

Kanda et al. Biochem. Biophys. Acta (1986) 870: 64-76 (Year: 1986).*

Chen, I. et al., "Site-specific labeling of proteins with small molecules in live cells", Current Opinion in Biotechnology 2005, 16:35-40. doi: 10.1016/j.copbio.2004.12.003.

Ehrbar, M. et al., "Enzymatic formation of modular cell-instructive fibrin analogs for tissue engineering", Biomaterials. 28, (2007) 3856-66. doi: 10.1016/j.biomaterials.2007.03.027.

Mosiewicz, K. et al., "In situ cell manipulation through enzymatic hydrogel photopatterning", Nature Materials, vol. 12, Nov. 2013, 1072-1078 doi. 10.1038/NMAT3766.

Fortunati, D. et al., "Cross-linking of collagen I by tissue transglutaminase provides a promising biomaterial for promoting bone healing", Amino Acids (2014) 46:1751-1761 doi: 10.1007/s00726-014-1732-0.

Griffin, D. et al., "Hybrid Photopatterned Enzymatic Reaction (HyPER) for in Situ Cell Manipulation", ChemBioChem 2014, 15, 233-242 doi: 10.1002/cbic.201300687.

van Vught, R. et al., "Site-specific Functionalization of Proteins and Their Applications to Therapeutic Antibodies", Computational and Structural Biotechnology Journal, (2014) vol. No. 9, Issue: 14, e201402001, doi.org/10.5936/csbj.201402001.

Wong, P. et al., "Photocontrolled Release of Doxorubicin Conjugated through a Thioacetal Photocage in Folate-Targeted Nanodelivery Systems", Bioconjugate Chemistry, 2017, 28, 3016-3028, doi: 10.1021/acs.bioconjchem.7b00614.

Brown, T. et al., "Spatiotemporal hydrogel biomaterials for regenerative medicine", Ch em. Soc. Rev., 2017, 46, 6532-6552 doi: 10.1039/c7cs00445a.

* cited by examiner

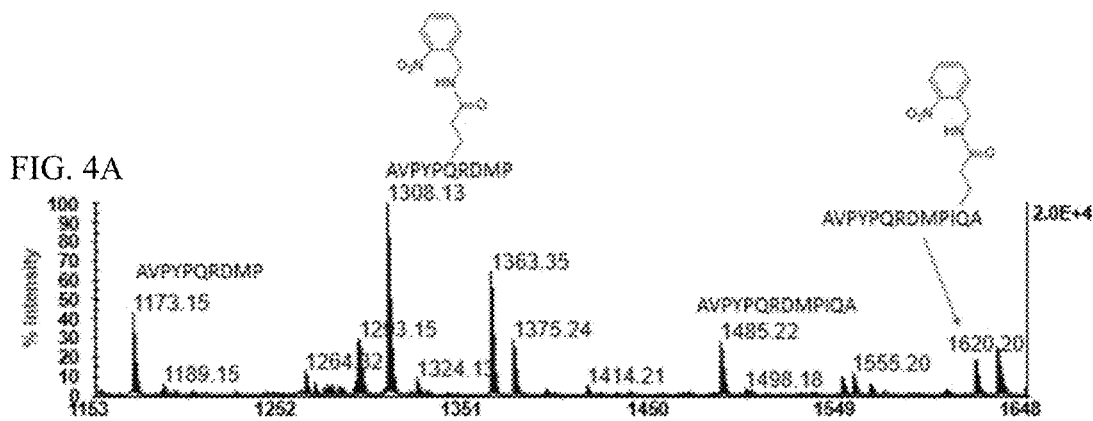
FIG. 4A
FIG. 4B
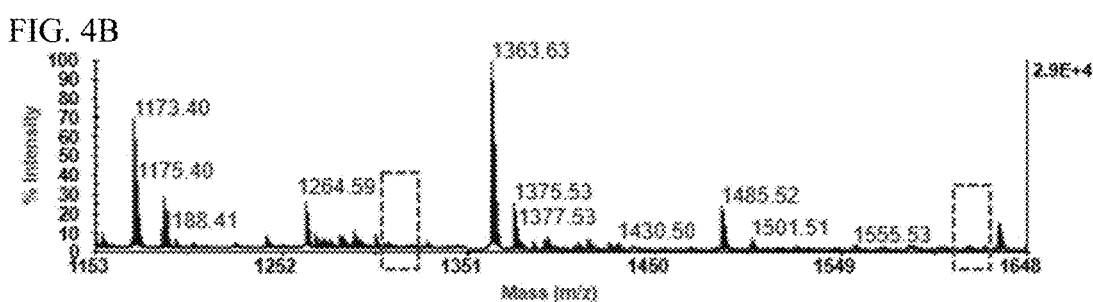
FIG. 5A
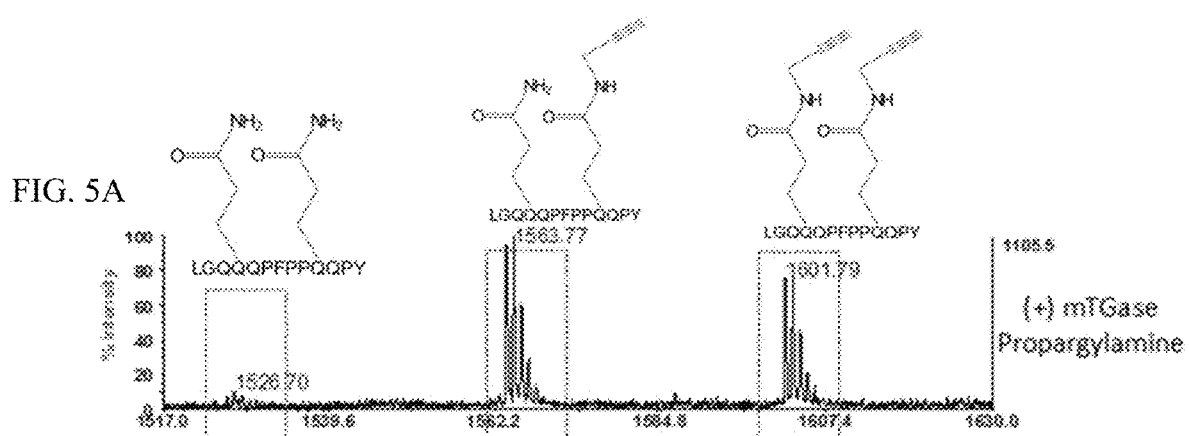
FIG. 5B
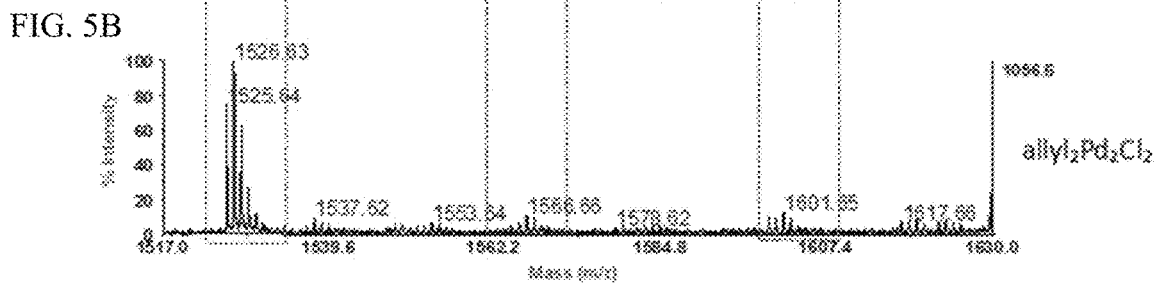

CHEMO-ENZYMATIC SITE-SPECIFIC MODIFICATION OF PEPTIDES AND PROTEINS TO FORM CLEAVABLE CONJUGATES

CROSS REFERENCE TO RELATED APPLICATIONS

This application claims the benefit under 35 U.S.C. § 119 of U.S. Provisional Patent Appl. Nos. 62/508,999, filed May 19, 2017, and 62/664,659, filed Apr. 30, 2018. The disclosures of these applications are incorporated herein by reference in their entireties.

STATEMENT REGARDING FEDERALLY SPONSORED RESEARCH OR DEVELOPMENT

The technology was developed with financial support from Grant No. GM101396 from the National Institutes of Health. The U.S. Government has certain rights in the technology.

BACKGROUND

Tools to exert functional control over proteins by structural modification are limited. Reversible and site-specific chemo-enzymatic modification of proteins can, in theory, be a means to overcome this problem. However, in practice many hurdles are encountered. A special case of the reversible modification of proteins and peptides is caging, a process in which a molecule is covalently modified to form a chemical derivative that typically reduces one or more functions of the molecule. This chemical derivative can be cleaved by a stimuli (e.g., light, metal, chemical reagents, or enzymes) to regenerate the original (native) molecule and thus recover the function. The molecule is often described as being 'caged', and the reverse process is often referred to as "decage" or "uncage".

Photocaging is a type of modification that can be reversed using light. In photocaging, a molecule is covalently modified to form a photolabile derivative that typically abolishes one or more functions of the molecule (Ellis-Davies 2007). Upon photolysis, the photolabile derivative is cleaved to regenerate the molecule and thus also recover the lost function (Adams et al 1993). The molecule is often described as being 'caged.' Photolysis is also commonly referred to as photo-cleavage, photo-activation, photo-release, photo-control, uncaging, or decaging. Photolysis permits both temporal and spatial control over the cleavage reaction and also permits quantitative control of the function being affected by the photocaging process (Klan et al. 2013). As such, photocaging has broad applications in chemistry, biology, medicine, materials sciences, and other fields (Givens et al 2004; Banghart et al 2012, Miesenbck 2011, Tatsu et al 1996; Dougherty et al. 1998; Cho et al 2015, Bao et al 2015; Gao et al 2004).

Photocaging of glutamine, both in free form (Ramesh et al., 1993) and within a peptide (Hiraoka, & Hamachi, 2003) has been described. However, its incorporation involves synthesis from a modified amino acid building block, requiring, e.g., solid-phase peptide synthesis, limiting its scope to small and simple peptides (Kotzur et al 2009, Ramesh et al 1993). Modification of amines (e.g., lysine or N-terminal amine) and thiols (e.g., cysteine) has also been reported, but these chemical methods are not site-specific in that the modification cannot limited to a select amino acid residue on a protein (Marriott 1994, Marriott et al 1998). For larger peptides and proteins, practical chemical modification of glutamyl amide has not been reported as the amide is chemically inert under conditions that most proteins can tolerate. More chemically reactive groups such as amines and thiols can be chemically modified; however, such chemical methods are not site-specific.

There is a need for site-specific methods for caging of peptides and proteins.

SUMMARY

The present technology provides a method for reversibly modifying a protein or peptide through its glutamine residues. An aspect of the method requires performing a transglutaminase-catalyzed reaction between the protein or peptide and an amine-containing reagent, linking the reagent through its amine function to the side chain of a glutamine residue. Subsequently, the modification can be reversed by a stimulus, such as exposure to light or a metal, which releases the amine containing reagent and regenerates the protein or peptide (or a structural homolog thereof). In cases where the transamidation leads to inactivation of the protein, the technology provides a method of temporarily inactivating the protein. The technology also provides a kit with the necessary components and instructions to reversibly modify a glutamine containing protein shortly before its contemplated use. Further, the technology provides a method of treating a disease by controlled release of a therapeutic agent which is linked through an amine function to a glutamine residue of a protein. The therapeutic agent is released at a suitable time and/or location by cleaving the bond linking the agent to the protein.

In one aspect, the technology provides a method for modifying a protein or peptide having one or more glutamine residues. The method includes the steps of performing a transglutaminase-catalyzed reaction between the protein or peptide and an amine-containing reagent, thereby producing a first derivative of the protein or peptide. As a result, the reagent becomes covalently linked through its amine function to a side chain of at least one of the one or more glutamine residues. The original protein or peptide, or a second derivative thereof, can be obtained by a treatment of the first derivative of the protein or peptide.

In another aspect, the technology provides a kit for reversibly modifying a protein or peptide having one or more glutamine residues. The kit includes (i) an amine-containing reagent, (ii) a transglutaminase, and (iii) instructions for reversibly modifying a protein or peptide with the amine-containing reagent. The kit can be used to reversibly modify a protein or peptide provided by the user, or alternatively, the kit can also include a protein or peptide for modification.

In yet another aspect, the technology provides a method of controlled delivery of a therapeutic agent. The method includes the steps of (a) modifying a protein or peptide having one or more glutamine residues by reacting with an amine-containing reagent in a transamidase-catalyzed reaction, such that the amine-containing reagent comprises a therapeutic agent, wherein the amine-containing reagent becomes linked through its amine function to a side chain of at least one of the one or more glutamine residues, thereby producing a derivative of the protein or peptide, (b) administering the derivative to a subject in need of receiving the therapeutic agent, and (c) subjecting the derivative to a treatment for reversing the modification, thereby releasing the therapeutic agent.

In a further aspect, the technology provides a method of controlled release of a therapeutic protein or peptide This the method includes (a) modifying a therapeutic protein or peptide having one or more glutamine residues by reacting the therapeutic protein or peptide with an amine-containing reagent in a transamidase-catalyzed reaction, wherein the amine-containing reagent becomes linked through its amine function to a side chain of at least one of the one or more glutamine residues, thereby producing a derivative of the therapeutic protein or peptide, (b) administering the derivative to a subject in need of receiving the therapeutic protein or peptide, and (c) subjecting the derivative to a treatment for reversing the modification, thereby releasing the amine-containing reagent and regenerating the therapeutic protein or peptide within the subject.

In another aspect, the technology provides a method of derivatizing an enzyme having one or more glutamine residues. This method includes the steps of (a) performing a transglutaminase-catalyzed reaction between the enzyme and an amine-containing reagent, whereby the reagent is linked through its amine function to a side chain of at least one of said one or more glutamine residues, and a first derivative of the enzyme is produced. The original enzyme, or a second derivative thereof, can be obtained by a treatment of the first derivative of the enzyme.

The technology is further summarized by the following listing of embodiments.

1. A method for modifying a protein or peptide having one or more glutamine residues, the method comprising:
performing a transglutaminase-catalyzed reaction between the protein or peptide and an amine-containing reagent, thereby producing a first derivative of the protein or peptide, wherein the reagent becomes covalently linked through its amine function to a side chain of at least one of said one or more glutamine residues; wherein the original protein or peptide, or a second derivative thereof, can be obtained by a treatment of the first derivative of the protein or peptide.
2. The method of embodiment 1, wherein the treatment comprises a photolysis reaction.
3. The method of embodiment 2, wherein the amine-containing reagent is a compound having the formula

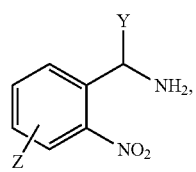

wherein
Y is selected from the group consisting of hydrogen, halogen, hydroxy, thiol, cyano, isocyano, thiocyano, isothiocyano, $(C_1-C_3)$alkyl, halo$(C_1-C_3)$alkyl, $(C_1-C_3)$alkyloxy; halo$(C_1-C_3)$alkyloxy, and cyclopropyl; and
Z is selected from the group consisting of hydrogen; halogen; hydroxy; nitro; cyano;
isocyano; thiocyano; isothiocyano; $(C_1-C_6)$alkyl; halo$(C_1-C_6)$alkyl; phenyl$(C_1-C_6)$alkyl; phenyl optionally substituted with halogen, $(C_1-C_3)$alkyl, halo$(C_1-C_3)$alkyl or $(C_1-C_3)$alkyloxy; $(C_1-C_3)$alkyloxy; cyclopropyl; halo$(C_1-C_3)$alkyloxy; $(C_2-C_4)$alkenyl; $(C_2-C_4)$alkynyl; $(C_1-C_6)$alkylthio; $C(O)OR^1$; $COR^1$; $CON(R^1)_2$; azide; sulfinyl; sulfonyl; sulfonyl halide; sulfino; sulfo; thiol; $(C_4-C_6)$diene; and aryl or aryloxy optionally substituted halogen or $(C_1-C_3)$alkyl;
wherein $R^1$ is hydrogen, halogen, $(C_1-C_3)$alkyl, halo$(C_1-C_3)$alkyl, or aryl optionally substituted with halogen or $(C_1-C_3)$alkyl.
4. The method of embodiment 2, wherein the amine-containing reagent is selected from the group consisting of:

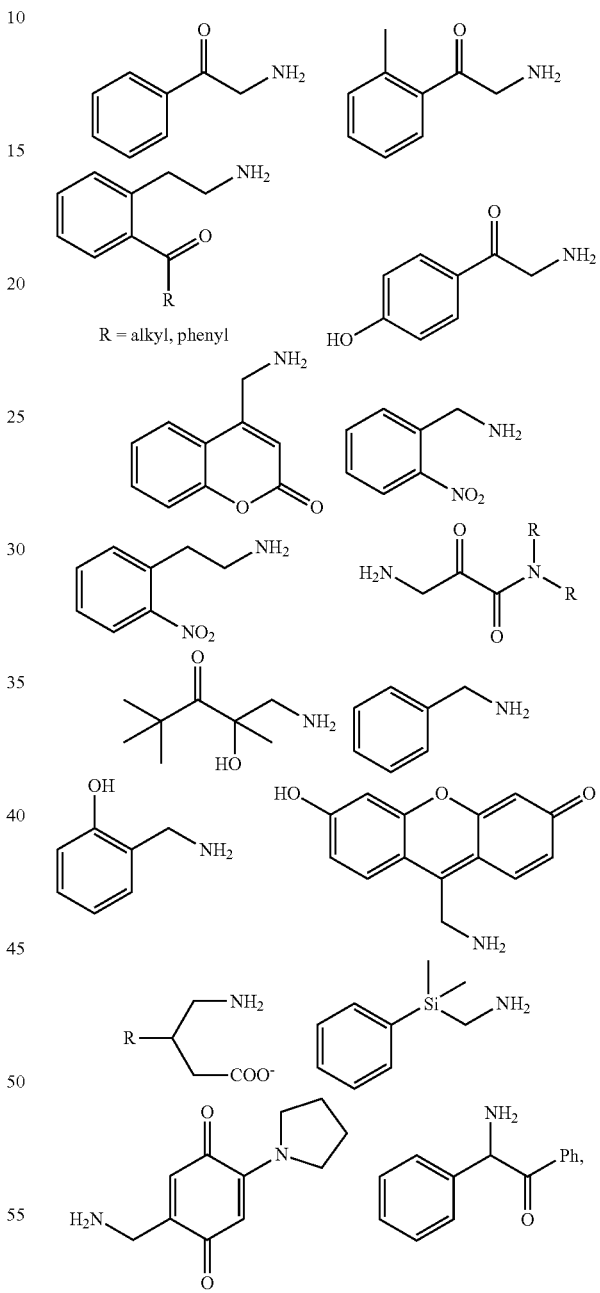

and 4,5-dimethoxy-2-nitrophenylethylamine.
5. The method of embodiment 2, wherein the amine-containing reagent comprises: (1) a hydroxylamine group, and the reagent is linked through the hydroxylamine group to the side chain of the at least one glutamine residue; or (2) a hydrazine group, and the reagent is linked through the hydrazine group to the side chain of the at least one glutamine residue.

6. The method of embodiment 5, wherein the reagent comprising a hydroxylamine group is a compound having the formula

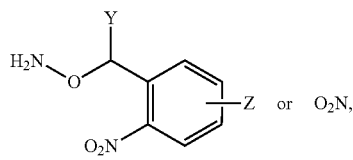

wherein

Y is selected from the group consisting of hydrogen, halogen, hydroxy, thiol, cyano, isocyano, thiocyano, isothiocyano, $(C_1$-$C_3)$alkyl, halo$(C_1$-$C_3)$alkyl, $(C_1$-$C_3)$alkyloxy; halo$(C_1$-$C_3)$alkyloxy, and cyclopropyl; and Z is selected from the group consisting of hydrogen; halogen; hydroxy; nitro; cyano; isocyano; thiocyano; isothiocyano; $(C_1$-$C_6)$alkyl; halo$(C_1$-$C_6)$alkyl; phenyl$(C_1$-$C_6)$alkyl; phenyl optionally substituted with halogen, $(C_1$-$C_3)$alkyl, halo$(C_1$-$C_3)$alkyl or $(C_1$-$C_3)$alkyloxy; $(C_1$-$C_3)$ alkyloxy; cyclopropyl; halo$(C_1$-$C_3)$alkyloxy; $(C_2$-$C_4)$ alkenyl; $(C_2$-$C_4)$alkynyl; $(C_1$-$C_6)$alkylthio; $C(O)OR^1$; $COR^1$; $CON(R^1)_2$; azide; sulfinyl; sulfonyl; sulfonyl halide; sulfino; sulfo; thiol; $(C_4$-$C_6)$diene; and aryl or aryloxy optionally substituted halogen or $(C_1$-$C_3)$alkyl; wherein $R^1$ is hydrogen, halogen, $(C_1$-$C_3)$alkyl, halo$(C_1$-$C_3)$alkyl, or aryl optionally substituted with halogen or $(C_1$-$C_3)$alkyl.

7. The method of embodiment 5, wherein the reagent comprising a hydroxylamine group is selected from the following compounds:

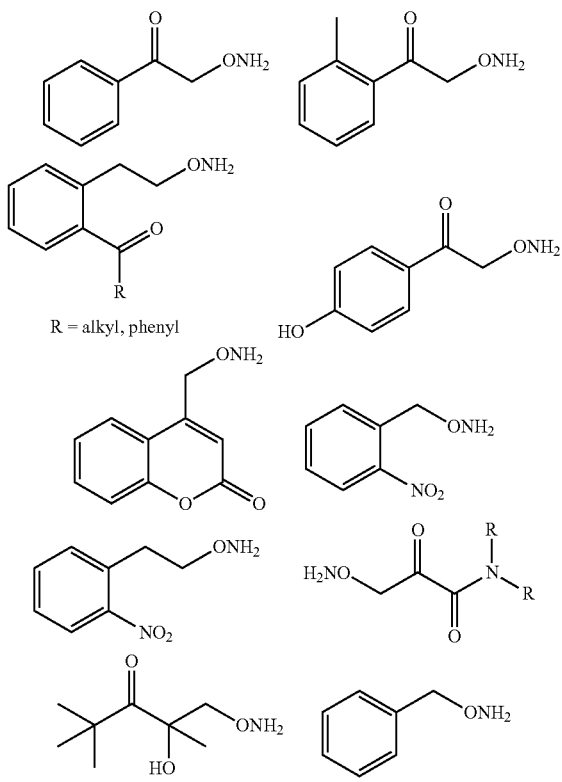

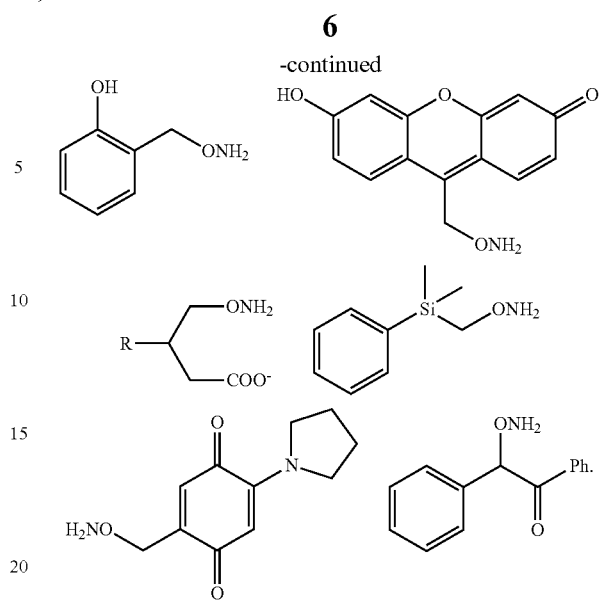

8. The method of embodiment 5, wherein the reagent comprising a hydrazine group is a compound having the formula

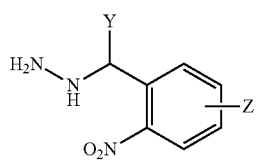

or wherein

Y, $R_1$ and $R_2$ are selected from the group consisting of hydrogen, halogen, hydroxy, thiol, cyano, isocyano, thiocyano, isothiocyano, $(C_1$-$C_3)$alkyl, halo$(C_1$-$C_3)$alkyl, $(C_1$-$C_3)$alkyloxy; halo$(C_1$-$C_3)$alkyloxy, and cyclopropyl; and Z is selected from the group consisting of hydrogen; halogen; hydroxy; nitro; cyano; isocyano; thiocyano; isothiocyano; $(C_1$-$C_6)$alkyl; halo$(C_1$-$C_6)$alkyl; phenyl$(C_1$-$C_6)$alkyl; phenyl optionally substituted with halogen, $(C_1$-$C_3)$ alkyl, halo$(C_1$-$C_3)$alkyl or $(C_1$-$C_3)$alkyloxy; $(C_1$-$C_3)$ alkyloxy; cyclopropyl; halo$(C_1$-$C_3)$alkyloxy; $(C_2$-$C_4)$ alkenyl; $(C_2$-$C_4)$alkynyl; $(C_1$-$C_6)$alkylthio; $C(O)OR^1$; $COR^1$; $CON(R^1)_2$; azide; sulfinyl; sulfonyl; sulfonyl halide; sulfino; sulfo; thiol; $(C_4$-$C_6)$diene; and aryl or aryloxy optionally substituted halogen or $(C_1$-$C_3)$alkyl; wherein $R^1$ is hydrogen, halogen, $(C_1$-$C_3)$alkyl, halo$(C_1$-$C_3)$alkyl, or aryl optionally substituted with halogen or $(C_1$-$C_3)$alkyl.

9. The method of embodiment 5, wherein the reagent comprising a hydrazine group is selected from the following compounds:

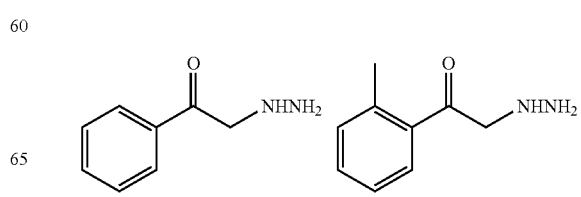

-continued

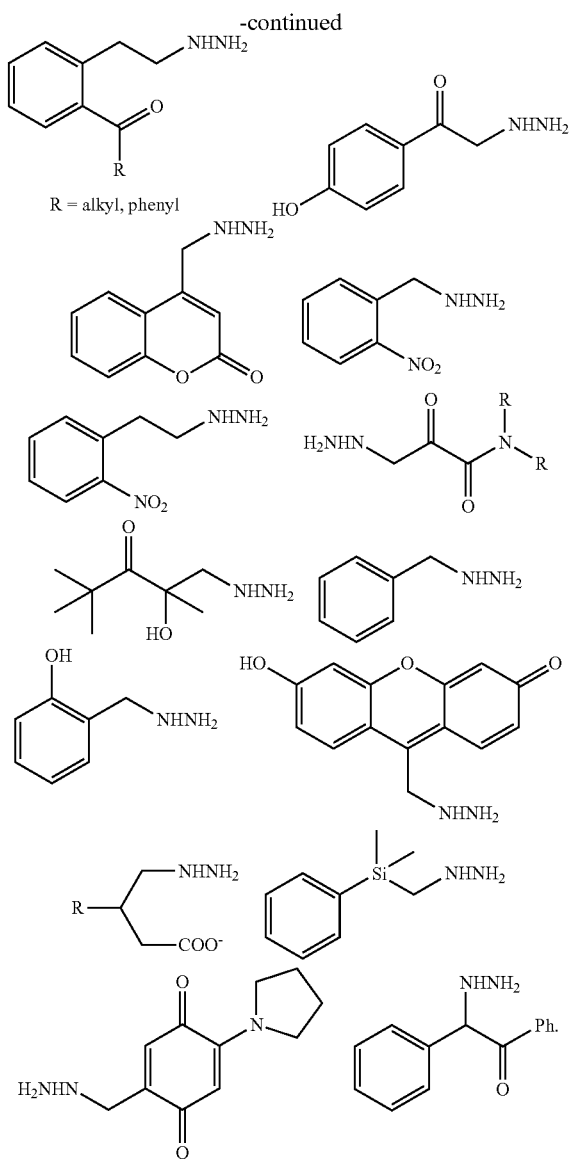

10. The method of embodiment 1, wherein the treatment comprises a reaction catalyzed by a metal in elemental form, a metal in ionic form, or a metal that is part of a complex.
11. The method of embodiment 10, wherein the amine-containing reagent is a compound having the formula

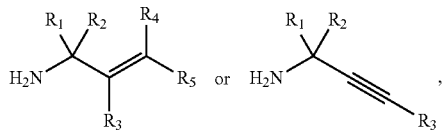

wherein $R_1$, $R_2$, $R_3$, $R_4$, and $R_5$ are independently selected from selected from the group consisting of: hydrogen; halogen; hydroxy; nitro; cyano; isocyano; thiocyano; isothiocyano; $(C_1$-$C_6)$alkyl; halo$(C_1$-$C_6)$alkyl; phenyl$(C_1$-$C_6)$alkyl; phenyl optionally substituted with halogen, $(C_1$-$C_3)$alkyl, halo$(C_1$-$C_3)$alkyl or $(C_1$-$C_3)$alkyloxy; $(C_1$-$C_3)$alkyloxy; cyclopropyl; halo$(C_1$-$C_3)$alkyloxy; $(C_2$-$C_4)$alkenyl; $(C_2$-$C_4)$alkynyl; $(C_1$-$C_6)$alkylthio; C(O)OR$^1$; COR$^1$; CON(R$^1$)$_2$; azide; sulfinyl; sulfonyl; sulfonyl halide; sulfino; sulfo; thiol; $(C_4$-$C_6)$diene; and aryl or aryloxy optionally substituted halogen or $(C_1$-$C_3)$alkyl; wherein R$^1$ is hydrogen, halogen, $(C_1$-$C_3)$alkyl, halo$(C_1$-$C_3)$alkyl, or aryl optionally substituted with halogen or $(C_1$-$C_3)$alkyl.

12. The method of embodiment 10, wherein the amine-containing reagent is a compound having a formula selected from the following compounds:

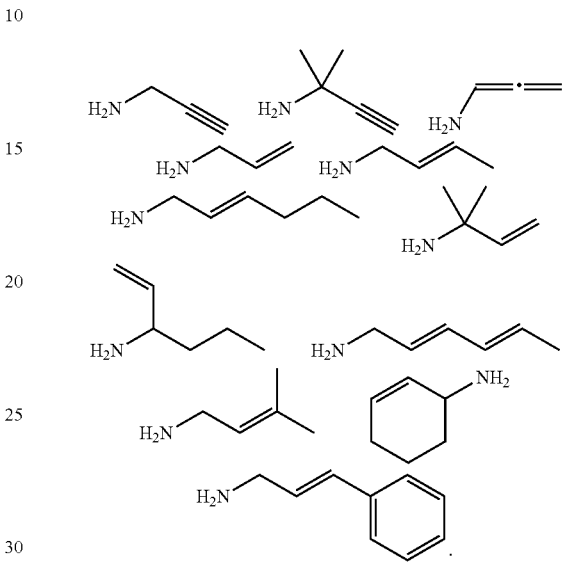

13. The method of embodiment 10, wherein the amine-containing reagent is a reagent comprising a hydroxylamine group, wherein the reagent is linked through the hydroxylamine group to a side chain of the at least one glutamine residue; or a reagent comprising a hydrazine group, wherein the reagent is linked through the hydrazine group to a side chain of the at least one glutamine residue.

14. The method of embodiment 13, wherein the reagent comprising a hydroxylamine group is a compound having the formula

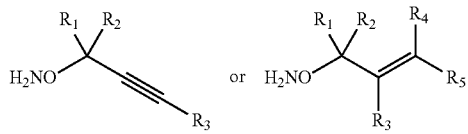

wherein $R_1$, $R_2$, $R_3$, $R_4$, and $R_5$ are independently selected from the group consisting of: selected from the group consisting of: hydrogen; halogen; hydroxy; nitro; cyano; isocyano; thiocyano; isothiocyano; $(C_1$-$C_6)$alkyl; halo$(C_1$-$C_6)$alkyl; phenyl$(C_1$-$C_6)$alkyl; phenyl optionally substituted with halogen, $(C_1$-$C_3)$alkyl, halo$(C_1$-$C_3)$alkyl or $(C_1$-$C_3)$alkyloxy; $(C_1$-$C_3)$alkyloxy; cyclopropyl; halo$(C_1$-$C_3)$alkyloxy; $(C_2$-$C_4)$alkenyl; $(C_2$-$C_4)$alkynyl; $(C_1$-$C_6)$alkylthio; C(O)OR$^1$; COR$^1$; CON(R$^1$)$_2$; azide; sulfinyl; sulfonyl; sulfonyl halide; sulfino; sulfo; thiol; $(C_4$-$C_6)$diene; and aryl or aryloxy optionally substituted halogen or $(C_1$-$C_3)$alkyl; wherein R$^1$ is hydrogen, halogen, $(C_1$-$C_3)$alkyl, halo$(C_1$-$C_3)$alkyl, or aryl optionally substituted with halogen or $(C_1$-$C_3)$alkyl.

15. The method of embodiment 13, wherein the reagent comprising a hydrazine group is a compound having the formula

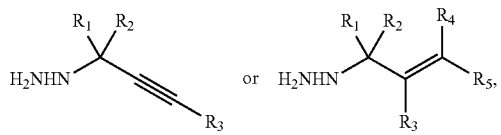

wherein $R_1$, $R_2$, $R_3$, $R_4$, and $R_5$ are independently selected from the group consisting of: selected from the group consisting of hydrogen; halogen; hydroxy; nitro; cyano; isocyano; thiocyano; isothiocyano; ($C_1$-$C_6$)alkyl; halo($C_1$-$C_6$)alkyl; phenyl($C_1$-$C_6$)alkyl; phenyl optionally substituted with halogen, ($C_1$-$C_3$)alkyl, halo($C_1$-$C_3$)alkyl or ($C_1$-$C_3$)alkyloxy; ($C_1$-$C_3$) alkyloxy; cyclopropyl; halo($C_1$-$C_3$)alkyloxy; ($C_2$-$C_4$)alkenyl; ($C_2$-$C_4$)alkynyl; ($C_1$-$C_6$)alkylthio; C(O)OR$^1$; COR$^1$; CON(R$^1$)$_2$; azide; sulfinyl; sulfonyl; sulfonyl halide; sulfino; sulfo; thiol; and ($C_4$-$C_6$)diene; and aryl or aryloxy optionally substituted halogen or ($C_1$-$C_3$)alkyl; wherein R$^1$ is hydrogen, halogen, ($C_1$-$C_3$)alkyl, halo($C_1$-$C_3$)alkyl, or aryl optionally substituted with halogen or ($C_1$-$C_3$)alkyl.

16. The method of embodiment 10, wherein the metal is palladium, iron, ruthenium, or platinum.

17. The method of embodiment 1, wherein the treatment comprises exposure to a physiological condition, altered pH, altered ionic strength, or elevated temperature.

18. The method of embodiment 17, wherein the amine-containing reagent is

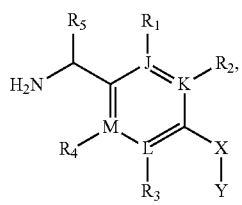

(I)

wherein

X is oxygen, sulfur, nitrogen, phosphorous, or selenium;
Y is hydrogen, alkyl, acyl, sulfo, or phospho;
J, K, L, and M are each independently carbon or nitrogen;
$R_1$, $R_2$, $R_3$, and $R_4$ are each independently hydrogen, halogen, hydroxyl, nitro, cyano, isocyano, thiocyano, isothiocyano, aryl, alkyl, alkenyl, alkynyl, alkoxy, alkylthio, amino, monoalkylamino, dialkylamino, acyl, carbonyl, carboxyl, azide, sulfinyl, sulfonyl, sulfino, sulfo, or thiol; and
$R_5$ is hydrogen, cyano, isocyano, aryl, alkyl, alkenyl, alkynyl, acyl, carbonyl, or carboxyl.

19. The method of embodiment 17, wherein the amine-containing reagent is

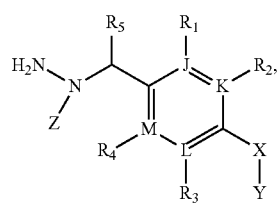

(II)

wherein:
Z is alkyl, aryl, acyl, acyloxy, alkenyl, alkynyl, silyl, sulfo, sulfonyl, sulfinyl, phospho, phosphonyl, acyl, cyano, alkoxy, or nitroso;
X is oxygen, sulfur, nitrogen, phosphorous, or selenium;
Y is hydrogen, alkyl, dialkyl, acyl, sulfo, sulfonyl, sulfinyl, phospho, phosphonyl, hydroxyl, silyl, nitrosyl, thiol, sulfide, or oxo;
J, K, L, and M are each independently carbon or nitrogen;
$R_1$, $R_2$, $R_3$, and $R_4$ are each independently hydrogen, halogen, hydroxyl, nitro, nitroso, cyano, isocyano, thiocyano, isothiocyano, aryl, alkyl, alkenyl, alkynyl, alkoxy, alkylthio, amino, monoalkylamino, dialkylamino, acyl, carbonyl, carboxyl, azide, sulfinyl, sulfonyl, sulfino, sulfo, or thiol; and
$R_5$ is hydrogen, cyano, isocyano, aryl, alkyl, alkenyl, alkynyl, acyl, carbonyl, or carboxyl.

20. The method of embodiment 17, wherein the amine-containing reagent is

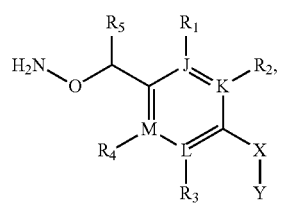

(III)

wherein:
X is oxygen, sulfur, nitrogen, phosphorous, or selenium;
Y is hydrogen, alkyl, dialkyl, acyl, sulfo, sulfonyl, sulfinyl, phospho, phosphonyl, hydroxyl, silyl, nitrosyl, thiol, sulfide, or oxo;
J, K, L, and M are each independently carbon or nitrogen;
$R_1$, $R_2$, $R_3$, and $R_4$ are each independently hydrogen, halogen, hydroxyl, nitro, nitroso, cyano, isocyano, thiocyano, isothiocyano, aryl, alkyl, alkenyl, alkynyl, alkoxy, alkylthio, amino, monoalkylamino, dialkylamino, acyl, carbonyl, carboxyl, azide, sulfinyl, sulfonyl, sulfino, sulfo, or thiol; and
$R_5$ is hydrogen, cyano, isocyano, aryl, alkyl, alkenyl, alkynyl, acyl, carbonyl, or carboxyl.

21. The method of embodiment 17, wherein the amine-containing reagent is

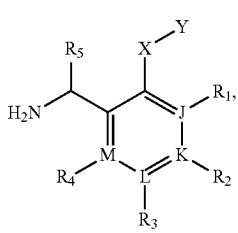

(IV)

wherein:
X is oxygen, sulfur, nitrogen, phosphorous, or selenium;
Y is hydrogen, alkyl, acyl, sulfo, or phospho;
J, K, L, and M are each independently carbon or nitrogen;
$R_1$, $R_2$, $R_3$, and $R_4$ are each independently hydrogen, halogen, hydroxyl, nitro, cyano, isocyano, thiocyano, isothiocyano, aryl, alkyl, alkenyl, alkynyl, alkoxy, alkylthio, amino, monoalkylamino, dialkylamino, acyl, carbonyl, carboxyl, azide, sulfinyl, sulfonyl, sulfino, sulfo, or thiol; and R₅ is hydrogen, cyano, isocyano, aryl, alkyl, alkenyl, alkynyl, acyl, carbonyl, or carboxyl.

22. The method of embodiment 17, wherein the amine-containing reagent is

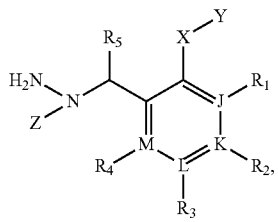

(V)

wherein

Z is alkyl, aryl, acyl, acyloxy, alkenyl, alkynyl, silyl, sulfo, sulfonyl, sulfinyl, phospho, phosphonyl, acyl, cyano, alkoxy, or nitroso;

X is oxygen, sulfur, nitrogen, phosphorous, or selenium;

Y is hydrogen, alkyl, dialkyl, acyl, sulfo, sulfonyl, sulfinyl, phospho, phosphonyl, hydroxyl, silyl, nitrosyl, thiol, sulfide, or oxo;

J, K, L, and M are each independently carbon or nitrogen;

$R_1$, $R_2$, $R_3$, and $R_4$ are each independently hydrogen, halogen, hydroxyl, nitro, nitroso, cyano, isocyano, thiocyano, isothiocyano, aryl, alkyl, alkenyl, alkynyl, alkoxy, alkylthio, amino, monoalkylamino, dialkylamino, acyl, carbonyl, carboxyl, azide, sulfinyl, sulfonyl, sulfino, sulfo, or thiol; and $R_5$ is hydrogen, cyano, isocyano, aryl, alkyl, alkenyl, alkynyl, acyl, carbonyl, or carboxyl.

23. The method of embodiment 17, wherein the amine-containing reagent is

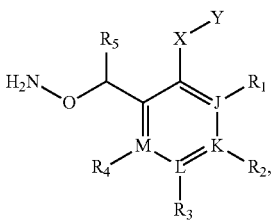

(VI)

wherein:

X is oxygen, sulfur, nitrogen, phosphorous, or selenium;

Y is hydrogen, alkyl, dialkyl, acyl, sulfo, sulfonyl, sulfinyl, phospho, phosphonyl, hydroxyl, silyl, nitrosyl, thiol, sulfide, or oxo;

J, K, L, and M are each independently carbon or nitrogen;

$R_1$, $R_2$, $R_3$, and $R_4$ are each independently hydrogen, halogen, hydroxyl, nitro, nitroso, cyano, isocyano, thiocyano, isothiocyano, aryl, alkyl, alkenyl, alkynyl, alkoxy, alkylthio, amino, monoalkylamino, dialkylamino, acyl, carbonyl, carboxyl, azide, sulfinyl, sulfonyl, sulfino, sulfo, thiol; and $R_5$ is hydrogen, cyano, isocyano, aryl, alkyl, alkenyl, alkynyl, acyl, carbonyl, or carboxyl.

24. The method of embodiment 17, wherein the amine-containing reagent is

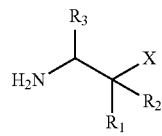

(VII)

wherein:

X is halogen, sulfonyl, sulfinyl, sulfoxo, cyano, isocyano, alkoxy, alkylthio, nitro, phospho, sulfo, or thiol;

$R_1$, and $R_2$ are each independently hydrogen, halogen, hydroxyl, nitro, cyano, isocyano, aryl, alkyl, alkenyl, alkynyl, alkoxy, alkylthio, amino, monoalkylamino, dialkylamino, acyl, carbonyl, carboxyl, azide, sulfinyl, sulfonyl, sulfino, sulfo, or thiol; and $R_3$ is hydrogen, cyano, aryl, alkyl, alkenyl, alkynyl, acyl, carbonyl, or carboxyl.

25. The method of embodiment 17, wherein the amine-containing reagent is

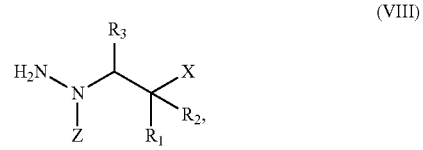

(VIII)

wherein:

Z is alkyl, aryl, acyl, acyloxy, alkenyl, alkynyl, silyl, sulfo, sulfonyl, sulfinyl, phospho, phosphonyl, acyl, cyano, alkoxy, or nitroso;

X is halogen, sulfonyl, sulfinyl, sulfo, sulfino, selenide, selenoxide, selenone, cyano, isocyano, alkoxy, alkylthio, nitro, amine oxide, phospho, or thiol;

$R_1$, and $R_2$ are each independently hydrogen, halogen, hydroxyl, nitro, cyano, isocyano, aryl, alkyl, alkenyl, alkynyl, alkoxy, alkylthio, amino, monoalkylamino, dialkylamino, acyl, carbonyl, carboxyl, azide, sulfinyl, sulfonyl, sulfino, sulfo, or thiol; and $R_3$ is hydrogen, cyano, aryl, alkyl, alkenyl, alkynyl, acyl, carbonyl, or carboxyl.

26. The method of embodiment 17, wherein the amine-containing reagent is

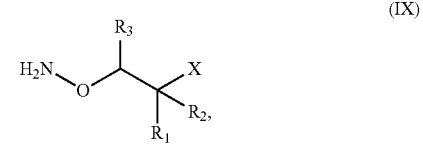

(IX)

wherein:

X is halogen, sulfonyl, sulfinyl, sulfo, sulfino, selenide, selenoxide, selenone, cyano, isocyano, alkoxy, alkylthio, nitro, amine oxide, phospho, or thiol;

$R_1$, and $R_2$ are each independently hydrogen, halogen, hydroxyl, nitro, cyano, isocyano, aryl, alkyl, alkenyl, alkynyl, alkoxy, alkylthio, amino, monoalkylamino, dialkylamino, acyl, carbonyl, carboxyl, azide, sulfinyl, sulfonyl, sulfino, sulfo, or thiol; and $R_3$ is hydrogen, cyano, aryl, alkyl, alkenyl, alkynyl, acyl, carbonyl, or carboxyl.

27. The method of any of the preceding embodiments, further comprising carrying out said treatment of the first derivative.
28. The method of any of the preceding embodiments, wherein the amine containing reagent is covalently linked to an effector moiety.
29. The method of embodiment 28, wherein the effector moiety is an effector peptide or protein, a PEG moiety, a DNA, a RNA, a carbohydrate, or a small molecule (having a molecular weight of 900 Daltons or less).
30. The method of embodiment 29 wherein the effector protein is an antibody or antigen binding fragment thereof, or an adjuvant.
31. The method of embodiment 29, wherein the small molecule is a pharmaceutical agent.
32. The method of embodiment 29, wherein the small molecule is a chromophore or a fluorophore.
33. The method of any of the preceding embodiments, wherein the transglutaminase is naturally occurring.
34. The method of any of embodiments 1-32, wherein the transglutaminase is engineered.
35. The method of any of the preceding embodiments, wherein the transglutaminase is microbial transglutaminase or mammalian transglutaminase.
36. The method of any of the preceding embodiments, wherein the amine-containing reagent is labeled at its amine function with $^{15}N$.
37. A method of modifying a protein or peptide, the method comprising performing an acyl-transfer reaction between the protein or peptide and an amine-containing reagent, whereby an amide bond is formed between the reagent and the protein or peptide.
38. The method of embodiment 37, wherein the acyl-transfer reaction is enzymatic.
39. The method of embodiment 37, wherein the acyl-transfer reaction is non-enzymatic.
40. The method of embodiment 37, wherein the acyl-transfer reaction occurs between a COOH or a $CONH_2$ group on the protein or peptide and the amine containing reagent.
41. A kit for reversibly modifying a protein or peptide having one or more glutamine residues, the kit comprising:
   (i) an amine-containing reagent,
   (ii) a transglutaminase, and
   (iii) instructions for reversibly modifying a protein or peptide with the amine-containing reagent.
42. The kit of embodiment 41, further comprising said protein or peptide.
43. The kit of embodiment 41 or 42, further comprising a reagent for reversing the modification of the protein or peptide.
44. A method of controlled delivery of a therapeutic agent, the method comprising:
   (a) modifying a protein or peptide having one or more glutamine residues by reacting with an amine-containing reagent in a transamidase-catalyzed reaction, wherein the amine-containing reagent comprises a therapeutic agent, wherein the amine-containing reagent becomes linked through its amine function to a side chain of at least one of the one or more glutamine residues, thereby producing a derivative of the protein or peptide,
   (b) administering the derivative to a subject in need of receiving the therapeutic agent,
   (c) subjecting the derivative to a treatment for reversing the modification, thereby releasing the therapeutic agent.
45. The method of embodiment 44, wherein the treatment for reversing the modification comprises performing the method of any one of embodiments 2-36.
46. The method of embodiment 44, wherein the protein or peptide having at least one glutamine residue is an antibody or an antigen binding fragment thereof with specificity to a tumor, and the therapeutic agent is an anticancer drug or a toxin.
47 The method of embodiment 46, wherein the toxin is a bacterial toxin.
48. The method of embodiment 47, wherein the bacterial toxin is *pseudomonas* exotoxin A or a fragment thereof, or diphtheria toxin or a fragment thereof
49. The method of embodiment 46, wherein the toxin is a plant toxin.
50. A method of controlled release of a therapeutic protein or peptide, the method comprising:
   (a) modifying a therapeutic protein or peptide having one or more glutamine residues by reacting the therapeutic protein or peptide with an amine-containing reagent in a transamidase-catalyzed reaction, wherein the amine-containing reagent becomes linked through its amine function to a side chain of at least one of the one or more glutamine residues, thereby producing a derivative of the therapeutic protein or peptide,
   (b) administering the derivative to a subject in need of receiving the therapeutic protein or peptide,
   (c) subjecting the derivative to a treatment for reversing the modification, thereby releasing the amine-containing reagent and regenerating the therapeutic protein or peptide within the subject.
51. The method of embodiment 50, wherein the therapeutic protein or peptide is an antibody or antigen-binding fragment thereof, a toxin, or an enzyme.
52. A method of derivatizing an enzyme having one or more glutamine residues, the method comprising:
   (a) performing a transglutaminase-catalyzed reaction between the enzyme and an amine-containing reagent, whereby the reagent is linked through its amine function to a side chain of at least one of said one or more glutamine residues, and a first derivative of the enzyme is produced; wherein the original enzyme, or a second derivative thereof, can be obtained by a treatment of the first derivative of the enzyme.
53. The method of embodiment 52, wherein the treatment comprises performing the method of any one of embodiments 2-36.
54. The method of embodiment 52, wherein the first derivative of the enzyme is inactive, and the original enzyme or second derivative of the enzyme is active.
55. The method of any of embodiments 52-54, wherein the enzyme is stable at a temperature range above ambient temperature, and the treatment comprises subjecting the first derivative to a temperature in said temperature range, thereby regenerating active enzyme.
56. The method of embodiment 55, wherein the enzyme is alpha-amylase from *Bacillus licheniformis*.
57. The method of embodiment 55, wherein the enzyme is made heat stable following step (a) by incorporating it in a matrix of non-reducing sugar.

BRIEF DESCRIPTION OF THE DRAWINGS

FIGS. 4A and 4B are positive mode MALDI-TOF-MS spectra demonstrating photolysis efficiency of beta casein thermolysin peptides AVPYPQRDMP (SEQ ID NO:1) and AVPYPQRDMPIQA (SEQ ID NO:2) caged with 2-nitrobenzylamine. FIG. 4A shows the spectrum before photolysis. Peaks at m/z 1308.13 and 1620.20 correspond to the modified AVPYPQRDMP (SEQ ID NO: 1) and AVPYPQRDMPIQA (SEQ ID NO: 2) peptides, respectively. FIG. 4B shows the spectrum after photolysis.

FIG. 5A is a negative mode MALDI TOF-MS spectrum of LGQQQPFPPQQPY (SEQ ID NO:3), alpha gliadin peptide (amino acids 31-43) obtained by mTGase catalyzed transamidation reaction with propargylamine (3 hours at 37° C., pH 8). Peaks at m/z 1563.77 and m/z 1601.79 correspond to alpha gliadin peptides modified at one and two glutamine residues, respectively. FIG. 5B shows the spectrum upon removal of the propargyl group, carried out in a reaction using allyl$_2$Pd$_2$Cl$_2$. The reaction was carried out for 2 hours at 37° C. The peak at m/z 1525.64 shows the original peptide.

FIG. 6B). One glutamine residue (Q10) was modified. FIG. 6B). Two glutamine residues (Q3 and Q10) were modified.

DETAILED DESCRIPTION

Figure 1A:
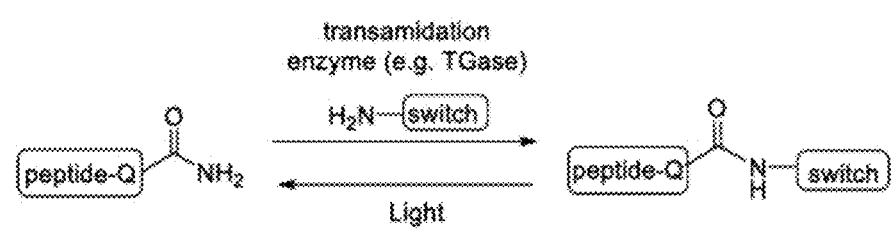
FIGS. 1A, 1B, and 1C are schematic diagrams showing transglutaminase-mediated (TGase-mediated) transamidation of a peptide and reversal of the transamidation by light (1A), a metal-catalyzed reaction (1B), and through tunable self-cleavage (1C).
Figure 1B:
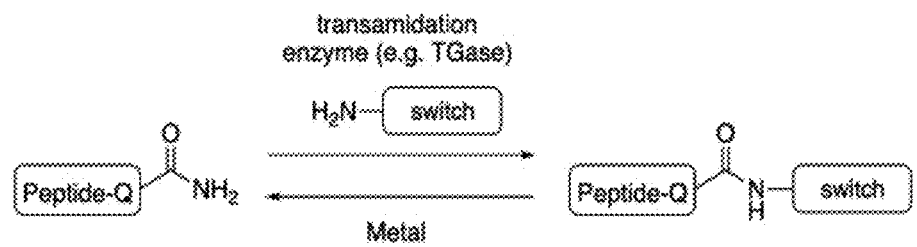
Figure 1C:
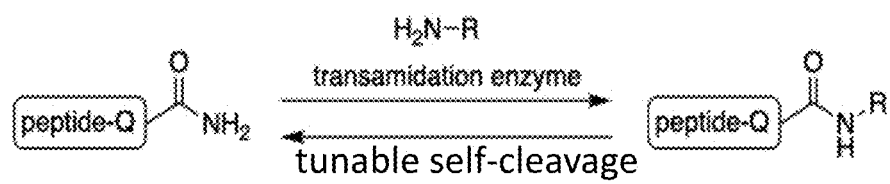

The present technology provides chemo-enzymatic methods for reversible site-specific modification of peptides or proteins. Specifically, the technology provides methods of linking a glutamine residue in a peptide or protein to a group using a transglutaminase (TGase) catalyzed transamidation reaction. The group can be removed in a subsequent reaction. The subsequent reaction can, for example, be photolysis or a metal catalyzed reaction, allowing regeneration of the original peptide or protein at a desired time and location. The methods also provide for further chemical modification of the group for generating additional peptide or protein derivatives, e.g., additional photo-releasable caged peptide/protein derivatives. Schemes illustrating caging strategy and resulting caged-conjugates methods are shown below:

Caging

Generally, "caging" refers to reducing the normal activity of a molecule by adding a group to the molecule thus generating a "caged" molecule. The group, when removed, releases the native (and active) form of the molecule.

A general scheme for incorporation of a photo-cleavable 'cage' or 'switch' into peptide or protein using an enzyme-mediated transamidation reaction is shown in Scheme I below. The "switch" substituent is meant to depict any nitrogen-containing substituent (e.g., a nucleophile). Photolysis can be used to regenerate the native peptide.

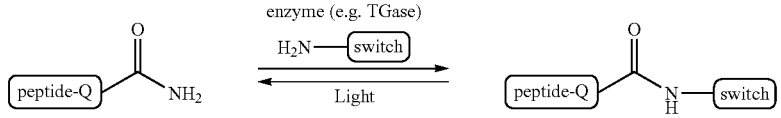

I

Conjugates

A general scheme for generating a photo-cleavable switch conjugate is shown in Scheme II below (either a one-step or a multi-step approach can be used). Again, the switch substituent is meant to depict any nitrogen-containing substituent (e.g., a nucleophile), and photolysis can be used to release the switch-conjugate and regenerate the native peptide.

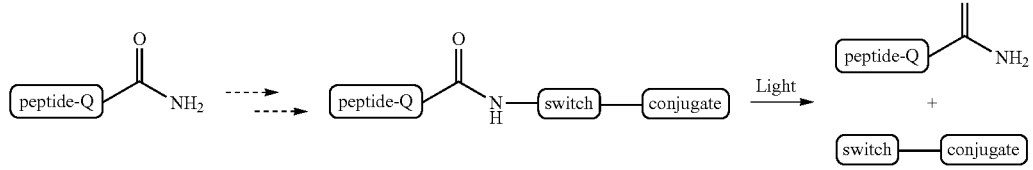

II

Exemplary photocaging groups, general caging properties, and photolytic reaction mechanisms are described below.

Photocaging Groups

Photocaging groups shown below (see Table 1, page 20, Klan, P. et al. 2013) may be used with the present technology

TABLE 1

| Photoremovable Protecting Groups | |
|---|---|
| [structure: phenacyl, PhC(O)CH2-X] | Section 2.1 |
| [structure: o-methylphenacyl] | Section 2.2 |
| [structure: 2-(o-acylphenyl)ethyl-X] | Section 2.2 |
| [structure: p-hydroxyphenacyl] | Section 2.3 |
| [structure: α-phenyl desyl, PhCH(X)C(O)Ph] | Section 2.4 |
| [structure: o-nitrobenzyl] | Section 3.1 |
| [structure: o-nitrophenethyl] | Section 3.2 |
| [structure: o-nitroanilide] | Section 3.3 |
| [structure: (coumarin-4-yl)methyl] | Section 4 |

TABLE 1-continued

| Photoremovable Protecting Groups | |
|---|---|
| [structure: benzyl-X] | Section 5.1 |
| [structure: o-hydroxybenzyl] | Section 5.2 |
| [structure: Ru(bpy)$_2$(R)(X)$^{2+}$] | Section 6 |
| [structure: α-hydroxy ketone] | Section 7.1 |
| [structure: o-benzoylbenzoate] | Section 7.2 |
| [structure: phenyl sulfonate] | Section 7.3 |
| [structure: α-keto ester] | Section 7.4 |
| [structure: carboxylate with R, X] | Section 7.5 |
| [structure: phenyldimethylsilylmethyl-X] | Section 7.6 |
| [structure: o-hydroxycinnamate] | Section 7.7 |
| [structure: α-keto amide] | Section 7.8 |

TABLE 1-continued

Photoremovable Protecting Groups

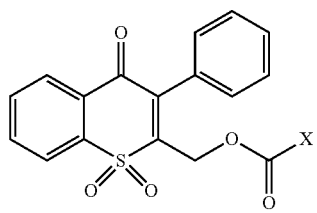
Section 7.9

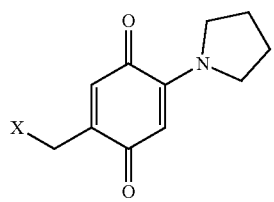
Section 7.10

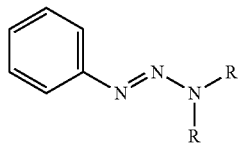
Section 7.11

TABLE 1-continued

Photoremovable Protecting Groups

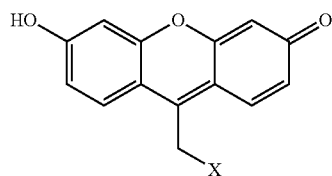
Section 7.12

Properties of Photocaging Groups

General requirements for successful photocaging and subsequent photolysis are described in CRC Handb. Org. Photochem. Photobiol. (2nd Ed.), 2004. The photocaging process generally requires the substrate (peptide or protein), caged substrate, and photoproducts to have good aqueous solubility. The photochemical release generally should be efficient ($\varphi > 0.10$). The departure of the substrate from the protecting group should primarily be a be photochemical process, i.e., occurring directly from the excited state of the cage chromophore. The photoproducts should be stable in the photolysis environment. The excitation wavelength should preferably be greater than 300 nm, and the medium, photoproducts, and the substrate should be such that they do not absorb in the region of the excitation wavelength. The chromophore should have a reasonable absorptivity (a) to efficiently capture incident light.

Photolytic Reaction Mechanisms of Photocaging Groups

The photolysis mechanism of 2-nitrobenzyl and 2-nitrophenylethyl groups is shown below.

2-nitrobenzyl group: 2-nitrobenzyl photolytic release mechanism is depicted in the scheme below (see Klan, P. et al. 2013, page 138). The mechanism proceeds through an aci-nitro intermediate to liberate the leaving group. In the example below, the leaving group is methanol, whereas in the technology described herein, the leaving group is the regenerated peptide or protein which, through one or more of its glutamine residues, was linked to the 2-nitrobenzyl group.

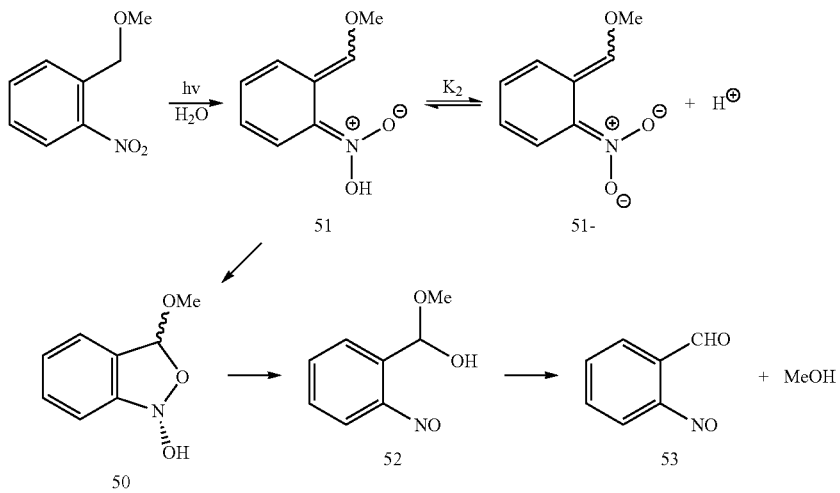

The photolytic release of the leaving group has been shown to be influenced by substituents at benzylic position as well as on the aromatic ring. Substitutions at each of these positions have been shown to directly impact quantum yields.

2-nitrophenylethyl group: The general reaction mechanism for photolysis of 2-nitrophenylethyl derivatives is depicted in the scheme below (Klan, P. et al. 2013). This mechanism also proceeds through an aci-nitro intermediate. However, in this case, the leaving group "X" is released via beta-elimination. In the present technology, the leaving group is the regenerated peptide or protein, which through one or more of its glutamine residues was linked to the 2-nitrophenylethyl group.

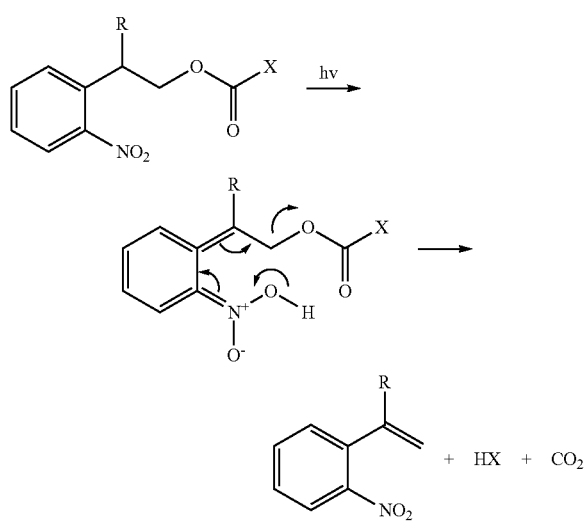

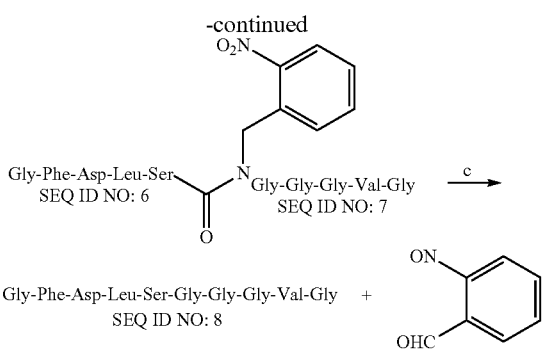

a - Nitrobenzaldehyde, NaBH₄, and Fmoc-Cl; b - solid phase peptide synthesis; and, c - UV irradiation. This strategy is limited to small peptides.

Previous Approaches to Protein Photocaging

Proteins have been photocaged with commercially available reagents that covalently modify amino acid residues in a non-specific manner (sometimes referred to as a 'shotgun' approach). A diagram depicting photocaging of G-actin protein using such a strategy is shown in the scheme below (Marriot, Biochemistry, 1994, 33 (31), pp 9092-9097).

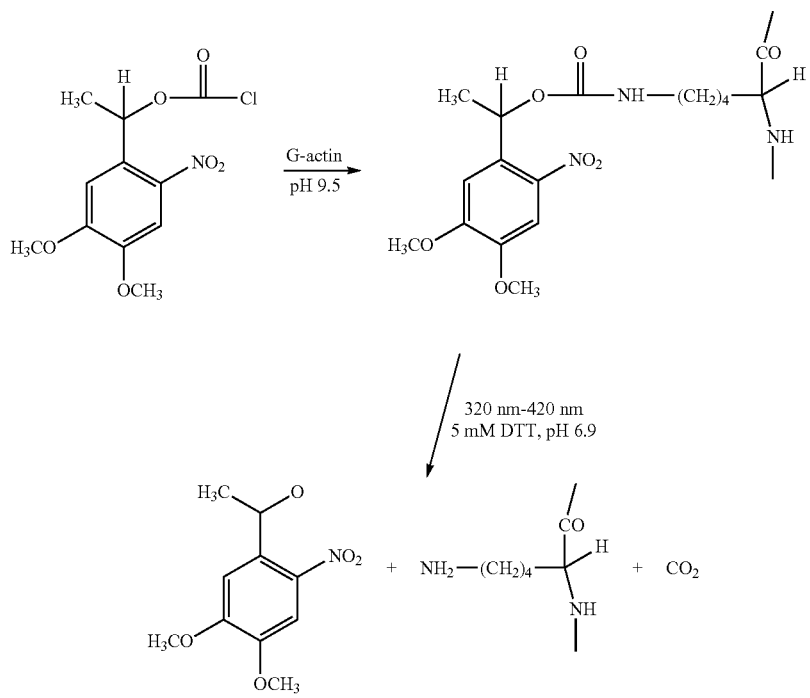

Previous Approaches to Photocaging of Peptides

Photocaging of peptides has thus far been carried out chemically during solid phase synthesis of the peptides. An example of photocaging of a peptide backbone is shown below (Y. Tatsu et al., 2002). The reagents and reactions used were as follows:

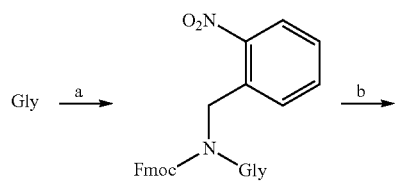

Specifically, the scheme shows the reaction mechanism of [(nitrophenyl)ethyl]carbamate photo-deprotection reaction. Unlike the methods of the present technology, this approach lacks the site-specificity afforded by use of enzymes. For example, in this approach, although the photocaging strategy is amino-specific, it is not known with certainty if groups such as serine or threonine would escape modification. Further, these non-specific approaches may also alter the charge of the protein, e.g., by modifying the charged amino acid lysine. The methods of the present technology do not, in general, alter charge, glutamine being neutral. As such, there is more likelihood of the protein maintaining solubility and stability.

25

Chemistry of Switch Installation and Photolysis

The term "switch" is used herein to describe a substituent on a caged derivative of a peptide or protein. The generated derivative as well as the released product (through photolysis or other means) are expected to be useful and functional. A "switch reagent" is a reagent that can be reacted with a peptide or protein to yield a switch-containing derivative of the peptide or protein.

"Nitrogen-containing reagents" are switch reagents containing a group that can be utilized in a catalyzed transamidation reaction to incorporate a switch into one or more glutamine residues in a peptide or protein. Nitrogen-containing reagents contemplated for use in the technology includes amine-containing reagents (amine-containing switch reagents), which include hydrazine-containing reagents (hydrazine-containing switch reagents), and hydroxylamine-containing reagents (hydroxylamine-containing switches).

Amine-Containing Reagents Used to Generate Photolabile Amides by Modifying Glutamine Residues A general scheme for modifying a protein or peptide having at least one glutamine residue with an amine containing photolabile reagent according to the present technology is shown below. The method includes performing an enzyme-catalyzed transamidation reaction (e.g., using transglutaminase as the enzyme) between the protein or peptide and an amine-containing photolabile reagent, whereby an amide bond is formed between the photolabile substituent (switch) and the side chain of the glutamine residue to yield a caged peptide or caged protein. Native peptide or protein is regenerated upon photolysis of the caged peptide or caged protein.

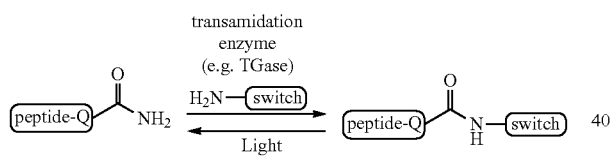

The method allows site-specific installation of a switch. Previously described non-specific chemical methods could not be used to specifically modify only glutamine residues in a protein or a peptide. The present method is generally applicable to glutamine-containing proteins and peptides. However, not all amines can serve as substrates for the transglutaminase enzyme. For example, experiments have revealed that 2-nitrobenzylamine is an excellent transglutaminase substrate, but methylation at the benzylic position abolished recognition by transglutaminase (likely due to steric effects).

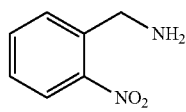 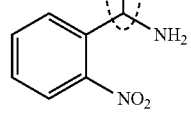

2-nitrobenzylamine        1-(2-Nitrophenyl)ethanamine

TGase substrate            Not TGase substrate

26

Photoremovable protecting groups generally useful in many applications in biology are described in Klan, P. et al. 2013. Some amine containing switch reagents suitable for use in the present technology are shown below.

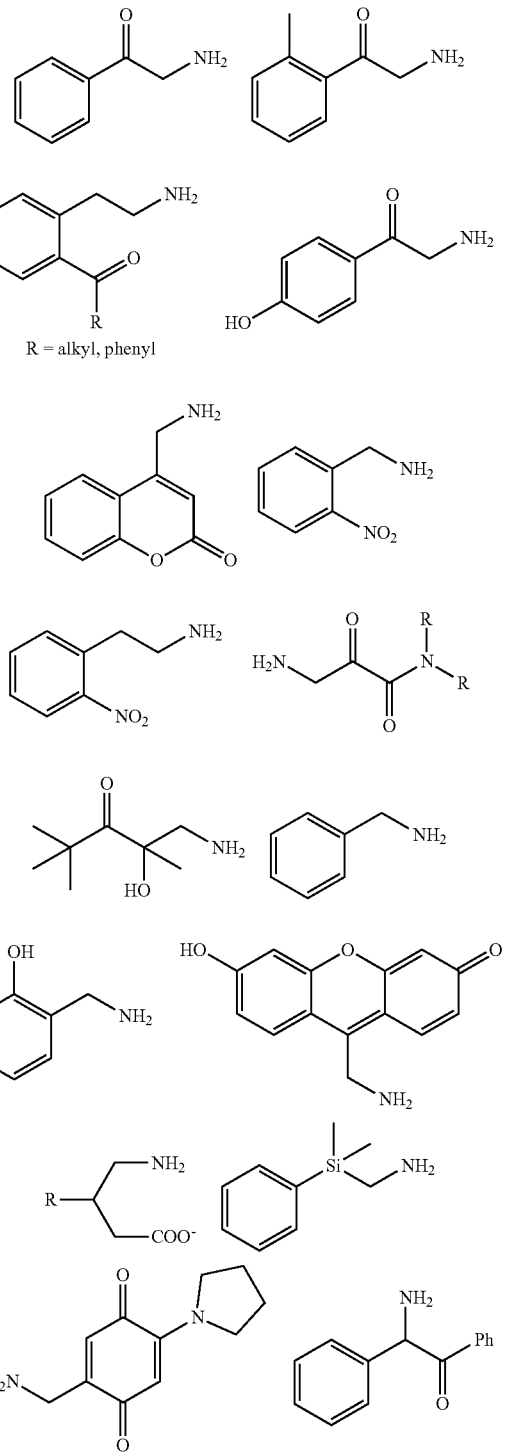

The amine-containing switch reagent can also be 2-nitrobenzylamine or a variant thereof with any combination of substituent Z on the aromatic ring at any position, and substituent Y at the benzylic carbon.

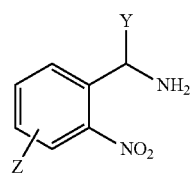

Additionally, the switch can be 2-(2-nitrophenyl)ethan-1-amine or a variant thereof with any combination of substituents Z on the aromatic ring at any position, and substituent Y at the benzylic carbon.

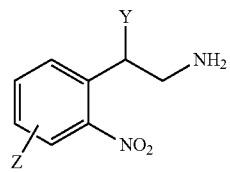

In the above two formulas, Y is selected from the group consisting of hydrogen, halogen, hydroxy, thiol, cyano, isocyano, thiocyano, isothiocyano, $(C_1-C_3)$alkyl, halo$(C_1-C_3)$alkyl, $(C_1-C_3)$alkyloxy; halo$(C_1-C_3)$alkyloxy, and cyclopropyl; and Z is selected from the group consisting of hydrogen; halogen; hydroxy; nitro; cyano; isocyano; thiocyano; isothiocyano; $(C_1-C_6)$alkyl; halo$(C_1-C_6)$alkyl; phenyl$(C_1-C_6)$alkyl; phenyl optionally substituted with halogen, $(C_1-C_3)$alkyl, halo$(C_1-C_3)$alkyl or $(C_1-C_3)$alkyloxy; $(C_1-C_3)$alkyloxy; cyclopropyl; halo$(C_1-C_3)$alkyloxy; $(C_2-C_4)$alkenyl; $(C_2-C_4)$alkynyl; $(C_1-C_6)$alkylthio; $C(O)OR^1$; $COR^1$; $CON(R^1)_2$; azide; sulfinyl; sulfonyl; sulfonyl halide; sulfino; sulfo; thiol; $(C_4-C_6)$diene; and aryl or aryloxy optionally substituted halogen or $(C_1-C_3)$alkyl; wherein $R^1$ is hydrogen, halogen, $(C_1-C_3)$alkyl, halo$(C_1-C_3)$alkyl, or aryl optionally substituted with halogen or $(C_1-C_3)$alkyl.

Switch Installation with Hydroxylamine-Containing Switch Reagents

A general scheme for modifying a protein or peptide having at least one glutamine residue with a hydroxylamine containing photolabile reagent according to the method of the present technology is shown below. The method includes performing an enzyme-catalyzed transamidation reaction (e.g. transglutaminase) between the protein or peptide and a hydroxylamine-containing photolabile reagent, whereby an oxyamide structure (see boxed structure below) is formed between the photolabile reagent (switch) and the side chain of the glutamine residue. Native peptide or protein (or a close structural homolog) is regenerated upon photolysis.

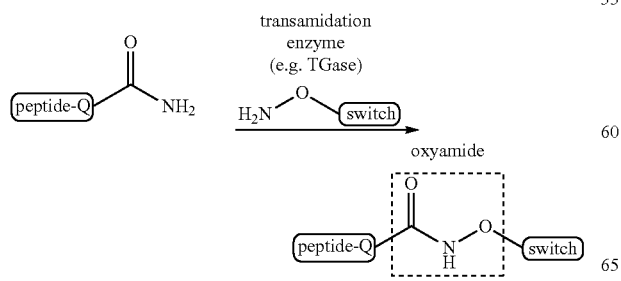

Some hydroxylamine containing switch reagents suitable for use in the methods described hereinabove are shown below (see Klan, P. et al. 2013).

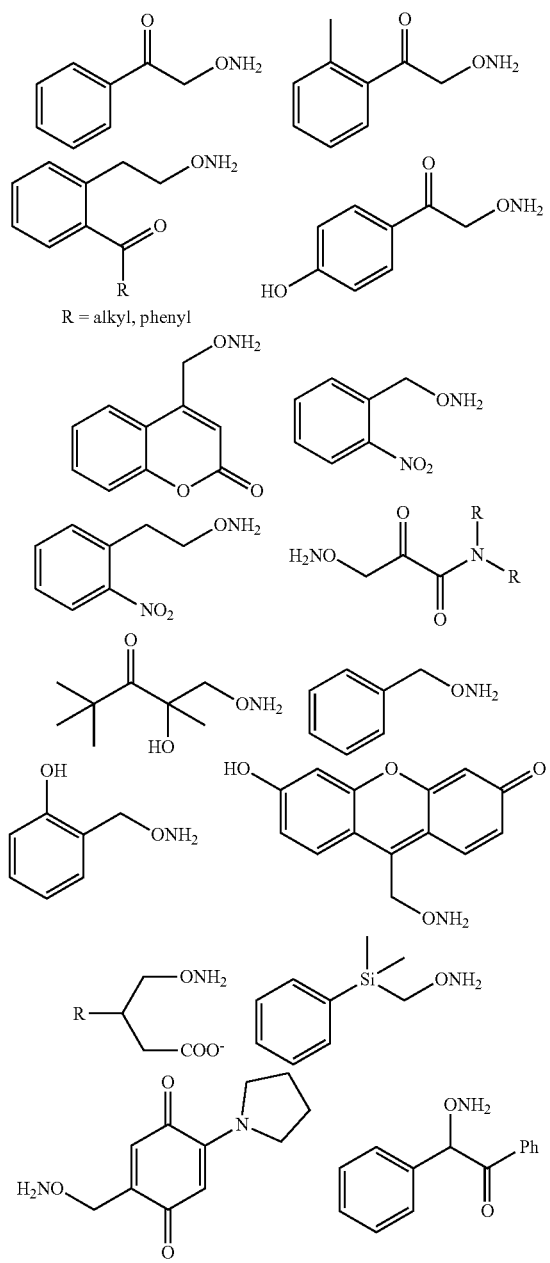

R = alkyl, phenyl

The switch reagent can also be hydroxylamine, O-[(2-nitrophenyl)methyl]- or a variant thereof with any combination of substituents on the aromatic ring (Z) and the benzylic carbon (Y).

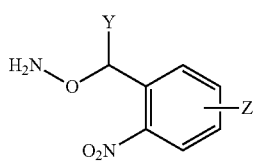

Additionally, the switch reagent can be a hydroxylamine, O-[2-(2-nitrophenyl)ethyl]- or variant thereof with any combination of substituents on the aromatic ring (Z) and the benzylic carbon (Y).

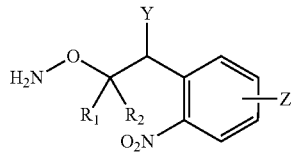

In the above two formulas, Y, $R_1$, and $R_2$ are selected from the group consisting of hydrogen, halogen, hydroxy, thiol, cyano, isocyano, thiocyano, isothiocyano, $(C_1-C_3)$alkyl, halo$(C_1-C_3)$alkyl, $(C_1-C_3)$alkyloxy; halo$(C_1-C_3)$alkyloxy, and cyclopropyl; and Z is selected from the group consisting of hydrogen; halogen; hydroxy; nitro; cyano; isocyano; thiocyano; isothiocyano; $(C_1-C_6)$alkyl; halo$(C_1-C_6)$alkyl; phenyl$(C_1-C_6)$alkyl; phenyl optionally substituted with halogen, $(C_1-C_3)$ alkyl, halo$(C_1-C_3)$alkyl or $(C_1-C_3)$alkyloxy; $(C_1-C_3)$ alkyloxy; cyclopropyl; halo$(C_1-C_3)$alkyloxy; $(C_2-C_4)$ alkenyl; $(C_2-C_4)$alkynyl; $(C_1-C_6)$alkylthio; $C(O)OR^1$; $COR^1$; $CON(R^1)_2$; azide; sulfinyl; sulfonyl; sulfonyl halide; sulfino; sulfo; thiol; $(C_4-C_6)$diene; and aryl or aryloxy optionally substituted halogen or $(C_1-C_3)$alkyl; wherein $R^1$ is hydrogen, halogen, $(C_1-C_3)$alkyl, halo$(C_1-C_3)$alkyl, or aryl optionally substituted with halogen or $(C_1-C_3)$alkyl. Furthermore, the reagent can be $^{15}N$ isotope-labeled or non-isotope labeled.

Switch Installation with Hydrazine-Containing Switch Reagents

A general scheme for modifying a protein or peptide having a least one glutamine residue with a hydrazine group-containing photolabile reagent according to the present technology is shown below. The method includes performing an enzyme-catalyzed transamidation reaction (e.g. transglutaminase) between the protein or peptide and a hydrazine group-containing photolabile reagent, whereby a photolabile hydrazide (see boxed structure below) is formed between switch and the side chain of the glutamine residue. Native peptide or protein is regenerated upon photolysis.

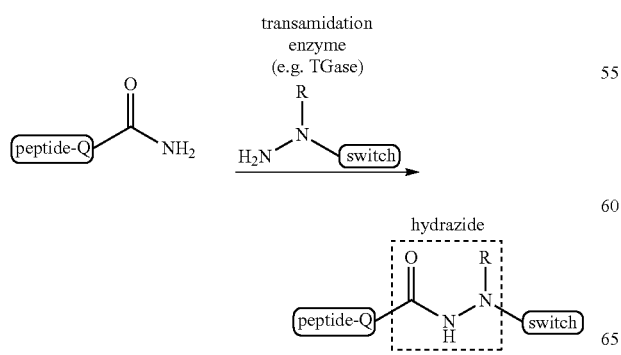

Some hydrazine group containing switch reagents suitable for use in the technology are shown below (see Klan et al. 2013).

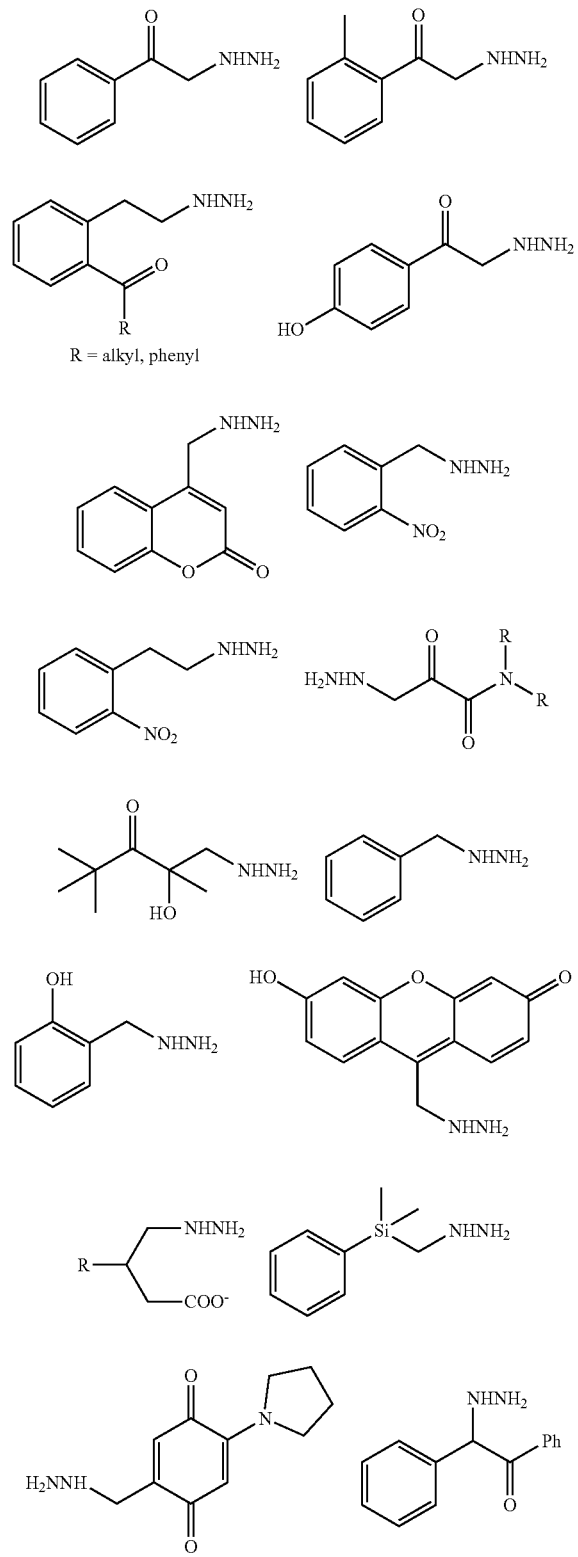

The switch can also be hydrazine, [(2-nitrophenyl)methyl]-hydrazine or a variant thereof with any combination of substituents on the aromatic ring (Z) and the benzylic carbon (Y).

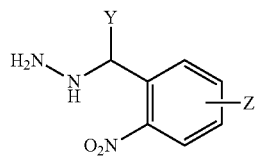

Additionally, the switch can be hydrazine, [2-(2-nitrophenyl)ethyl]-hydrazine or variant of hydrazine, [2-(2-nitrophenyl)ethyl]- with any combination of substituents on the aromatic ring (Z) and the benzylic carbon (Y).

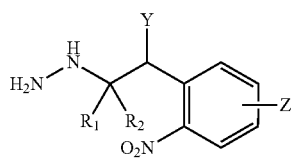

In the above two formulas, Y, $R_1$, and $R_2$ are selected from the group consisting of hydrogen, halogen, hydroxy, thiol, cyano, isocyano, thiocyano, isothiocyano, $(C_1-C_3)$alkyl, halo$(C_1-C_3)$alkyl, $(C_1-C_3)$alkyloxy; halo$(C_1-C_3)$alkyloxy, and cyclopropyl; and Z is selected from the group consisting of hydrogen; halogen; hydroxy; nitro; cyano; isocyano; thiocyano; isothiocyano; $(C_1-C_6)$alkyl; halo$(C_1-C_6)$alkyl; phenyl$(C_1-C_6)$alkyl; phenyl optionally substituted with halogen, $(C_1-C_3)$alkyl, halo$(C_1-C_3)$alkyl or $(C_1-C_3)$alkyloxy; $(C_1-C_3)$ alkyloxy; cyclopropyl; halo$(C_1-C_3)$alkyloxy; $(C_2-C_4)$alkenyl; $(C_2-C_4)$alkynyl; $(C_1-C_6)$alkylthio; C(O)O$R^1$; CO$R^1$; CON$(R^1)_2$; azide; sulfinyl; sulfonyl; sulfonyl halide; sulfino; sulfo; thiol; $(C_4-C_6)$diene; and aryl or aryloxy optionally substituted halogen or $(C_1-C_3)$alkyl; wherein $R^1$ is hydrogen, halogen, $(C_1-C_3)$alkyl, halo$(C_1-C_3)$alkyl, or aryl optionally substituted with halogen or $(C_1-C_3)$alkyl.

Incorporation of a switch using hydrazine chemistry can also be performed in two steps in which the first step adds a hydrazide group to the protein or peptide glutamine residue through a transglutaminase catalyzed reaction.

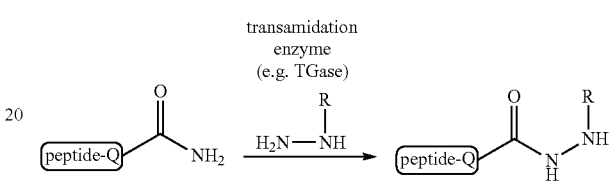

The hydrazide derivative obtained is further modified by reacting with a photolabile switch containing a hydrazide-reactive functional group (several are outlined below) thereby modifying the hydrazide derivative. The original terminal hydrazide may be substituted or unsubstituted.

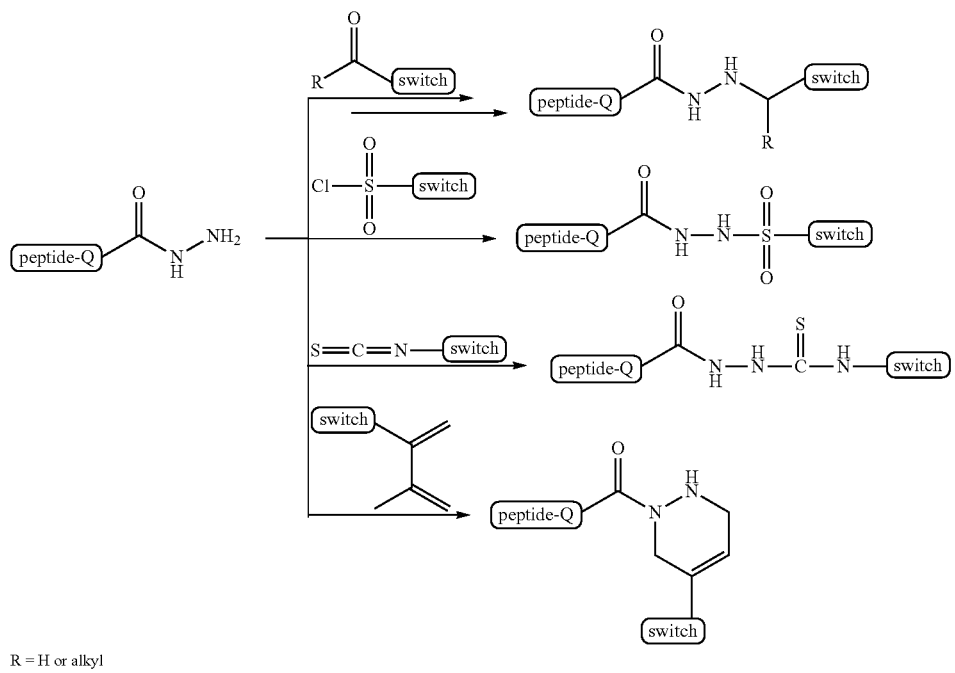

R = H or alkyl

Photolysis

During photolysis a chromophore covalently linked to peptide or protein absorbs a photon of light, triggering it to enter an 'excited-state' which leads to electron rearrangement and ultimate release of caged leaving group. While UV light (>300 nm, such as having a wavelength between 300 nm and 400 nm) is generally utilized for most of the photocaging groups previously described, there are other means, e.g., infrared (IR) light two- or multiphoton absorption (see Piant et al 2016), that can generate the desired decaging depending on the chromophore being utilized. Quantum yield is a key measure of photolytic efficiency. Products obtained by photolysis of molecules resulting from reaction between the switch reagents and the side chain of the glutamine residue are shown below.

Photolytic products of oxyamide or hydrazide switches: A general scheme of products obtained by photolysis of oxyamide or hydrazide switches derived molecules is shown below. Oxyamide switch derived product can also give rise to glutamic acid containing regenerated peptide.

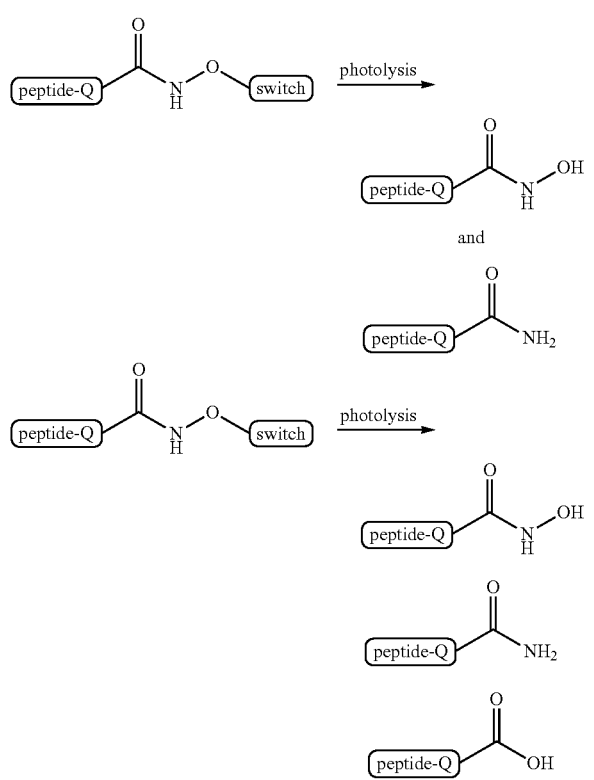

Photolysis of switch conjugate: Upon photolysis of a switch-conjugate linked to glutamine, the native peptide or functional equivalent of native peptide is regenerated and switch conjugate is released as depicted below.

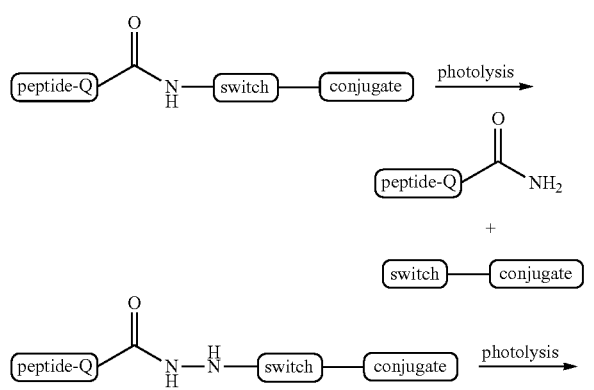

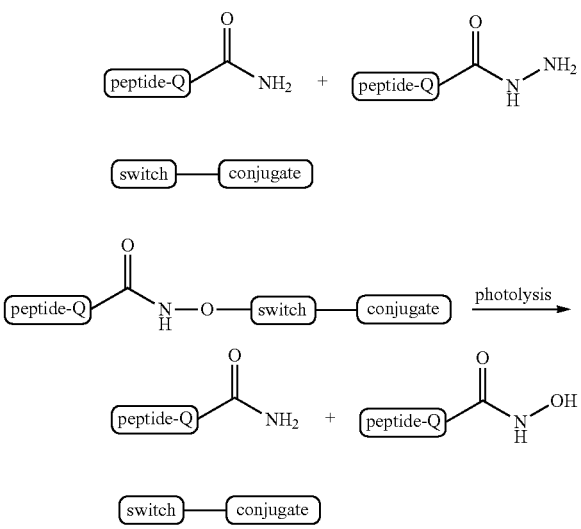

The method allows light-controlled release of the switch conjugate. Switch conjugate and photolytic products are each contemplated to be useful and functional. Further, the method allows control and modulation of activity based on different quantum yields of the installed switch (e.g., amine vs hydrazine).

Incorporation and Removal of $^{15}$N-Isotope Labeled Groups

Any photolabile switch (or switch conjugate) listed above (amine, hydrazine, hydroxylamine, etc.) can be $^{15}$N-isotope labeled. The newly generated $^{15}$N-labeled peptide and protein conjugates can be used as probes alone or together with photo-cleavable moiety in a variety of applications. Moreover, a $^{15}$N-labeled glutamine side chain can be generated upon photolysis, thus providing a method for site-specific N-labeling of peptides and proteins.

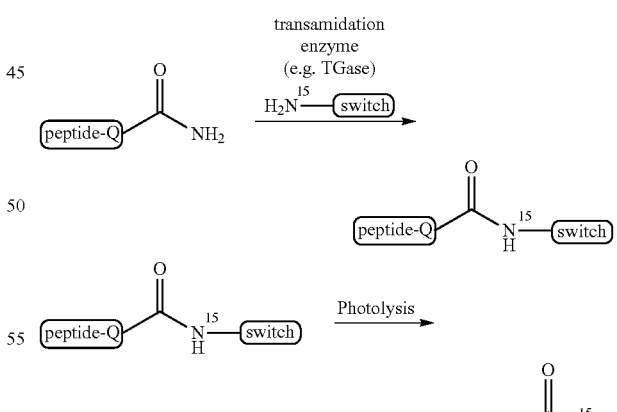

Alternatively, a glutamine-containing peptide or protein having $^{15}$N-labeled carboxamide group can be the starting material. By performing an enzyme-mediated transamidation reaction with non-isotopically labeled switch, the $^{15}$N label originally present on the glutamine side chain can be removed upon photolysis.

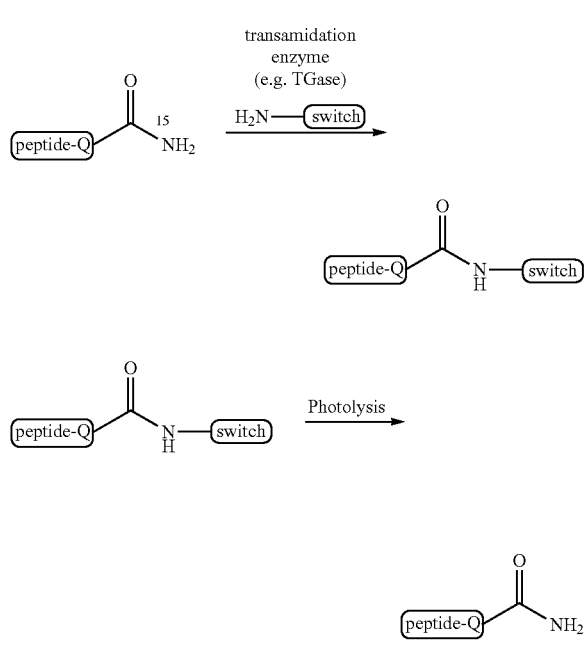

Acyl-Transfer Reaction:

It is contemplated that the method of installing photolabile switches or switch-conjugates into peptides or proteins is not limited to glutamine side chain transamidation, but can also be achieved by any acyl-transfer reaction between a protein or peptide and an amine-containing switch, whereby an amide bond is formed between the switch and the protein or peptide (see schematic diagram below). The acyl-transfer reaction can either be enzyme-mediated or non-enzymatic and the amine switch can optionally be labeled with $N^{15}$-labeled or non-isotope labeled.

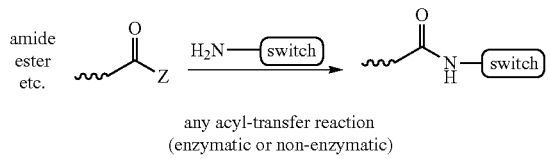

any acyl-transfer reaction
(enzymatic or non-enzymatic)

The product from acyl-transfer reaction seen above can be expected to generate an amide upon photolysis.

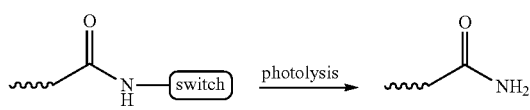

For example, non-enzymatic modification using nitrogen containing reagent (as denoted above) as nucleophiles may be achieved as shown below.

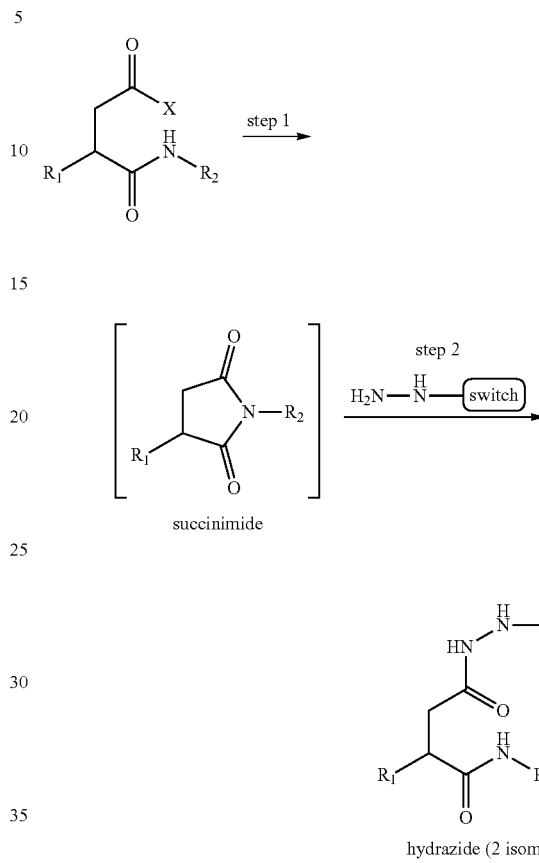

in which X is $NH_2$, or OH

Deamidation of asparagine or isomerization of aspartic acids and similar functional groups results in a succinimide intermediate (step 1). $R_1$, $R_2$, and Z groups in this step can be a typical peptide backbone residue, as well as other structures that can form succinimide. The labile intermediate can be trapped with various nucleophiles (such as water, hydrazines, and hydroxylamines) to form new derivatives. Two isomers (having alpha and beta peptide linkage) can be formed. Of note, original functional group or a close structural homolog is necessarily regenerated upon photolysis.

Metal-Mediated Cleavage Reactions

Certain groups introduced by enzyme-mediated transamidation may be removed using a metal-mediated cleavage reaction. Cleavage can be mediated by metal ions, metal complexes, or elemental metal. If the modification resulted in a loss of activity of the molecule, the removal is accompanied by recovery of the lost function.

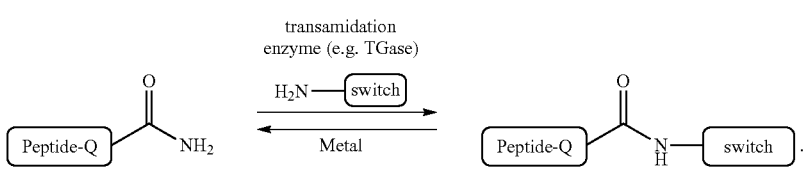

In this reaction scheme, the term "switch" describes a metal-cleavable substituent on a caged derivative of a peptide or protein. The generated derivative as well as the metal-released product are expected to be useful and functional. A "switch reagent" is a reagent that can be reacted with a peptide or protein to yield a switch-containing derivative of the peptide or protein. Unless specified, metal in all cases means either metal ions, or a metal in its elemental state, or a metal in a complex.

Conjugates

A general scheme for generating a metal-cleavable switch conjugate is shown in Scheme II below (either a one-step or a multi-step approach can be used). Again, the switch substituent is meant to depict any nitrogen-containing substituent (e.g., a nucleophile), and metal ions can be used to release the switch-conjugate and regenerate the native peptide.

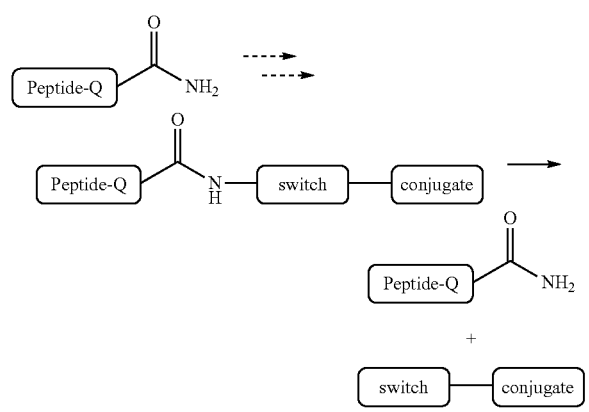

The technology encompasses metal-cleavable groups, and metal-mediated reaction mechanisms described below.

Amine-Containing Reagents Used to Generate Metal-Cleavable Amides by Modifying Glutamine Residues Exemplary metal-cleavable groups that may be used generate metal-cleavable amides by modifying glutamine residues are described below.

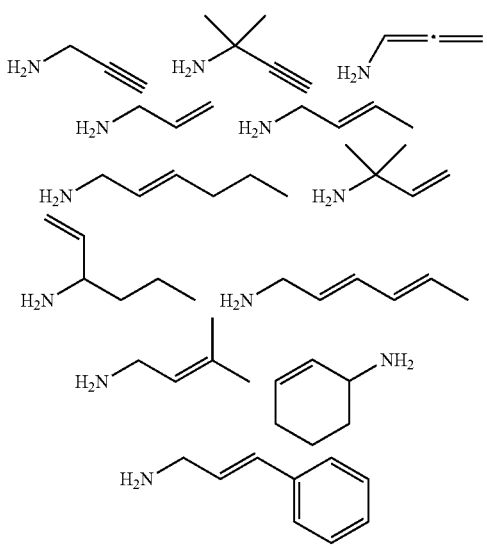

Alkene-Amine Series

In one embodiment, the switch is an alkene-containing derivative on a substitute amide group that may undergo de-alkylation upon addition of a metal.

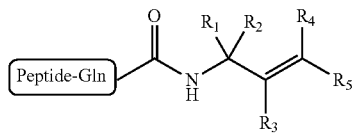

The switch can be an allylamine or a variant thereof with any combination of substituents $R_1$, $R_2$, $R_3$, $R_4$, and $R_5$ on the allyl group.

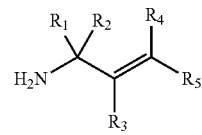

In the above formulas, $R_1$, $R_2$, $R_3$, $R_4$, and $R_5$ are independently one of: hydrogen; halogen; hydroxy, nitro, cyano, isocyano, thiocyano, isothiocyano, $(C_1\text{-}C_6)$alkyl; halo$(C_1\text{-}C_6)$alkyl; phenyl$(C_1\text{-}C_6)$alkyl, phenyl being optionally substituted with halogen, $(C_1\text{-}C_3)$alkyl, halo$(C_1\text{-}C_3)$alkyl and $(C_1\text{-}C_3)$alkyloxy; cyclopropyl; $(C_1\text{-}C_3)$alkyloxy; halo$(C_1\text{-}C_3)$alkyloxy; alkenyl or alkynyl having up to four carbon atoms; $(C_1\text{-}C_6)$alkylthio; C(O)OR$^1$, COR$^1$, and CON(R$^1$)$_2$, wherein R$^1$ is hydrogen, halogen, $(C_1\text{-}C_6)$alkyl, halo$(C_1\text{-}C_6)$alkyl, and aryl, optionally substituted with halogen or $(C_1\text{-}C_6)$alkyl; azide; sulfinyl; sulfonyl; sulfonyl halide; sulfino; sulfo; thiol; and aryl or aryloxy optionally substituted halogen or $(C_1\text{-}C_3)$alkyl.

Alkyne-Amine Series

In another embodiment, the switch is an alkyne-containing derivative on the glutamine amide group that can undergo de-alkylation upon addition of a metal.

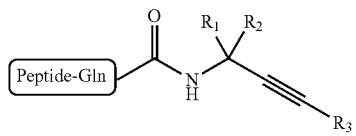

The amine-containing switch reagent that may be used to produce the above derivative can be propargylamine or a variant thereof as shown below.

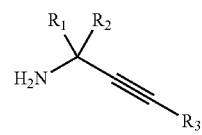

In the above formula, $R_1$, $R_2$, and $R_3$, are independently one of: hydrogen; halogen; hydroxy, nitro, cyano, isocyano, thiocyano, isothiocyano, $(C_1\text{-}C_6)$alkyl; halo$(C_1\text{-}C_6)$alkyl; phenyl$(C_1\text{-}C_6)$alkyl, phenyl being optionally substituted with halogen, $(C_1\text{-}C_3)$alkyl, halo$(C_1\text{-}C_3)$alkyl and $(C_1\text{-}C_3)$alkyloxy; cyclopropyl; $(C_1\text{-}C_3)$alkyloxy; halo$(C_1\text{-}C_3)$alkyloxy; alkenyl or alkynyl having up to four carbon atoms;

($C_1$-$C_6$)alkylthio; C(O)OR$^1$, COR$^{1-}$, and CON(R$^1$)$_2$, wherein R$^1$ is hydrogen, halogen, ($C_1$-$C_6$)alkyl, halo($C_1$-$C_6$)alkyl, and aryl, optionally substituted with halogen or ($C_1$-$C_6$) alkyl; azide; sulfinyl; sulfonyl; sulfonyl halide; sulfino; sulfo; thiol; and aryl or aryloxy optionally substituted halogen or ($C_1$-$C_3$)alkyl.

Switch Installation with Hydroxylamine-Containing Switch Reagents

A general scheme for modifying a protein or peptide having at least one glutamine residue with a hydroxylamine containing metal-cleavable reagent according to the method of the present technology is shown below.

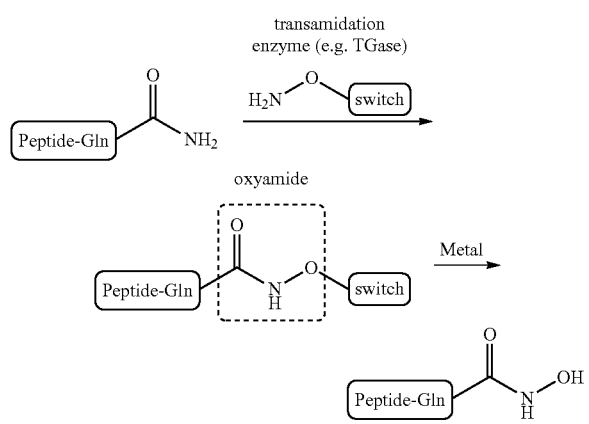

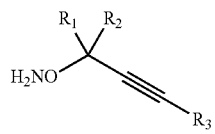

The switch reagent can be hydroxylamine, O-2-propynyl- or a variant thereof with any combination of substituents R$_1$, R$_2$, and R$_3$.

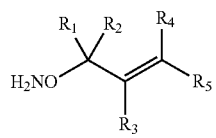

Alternatively, the switch reagent can be a hydroxylamine, O-2-propenyl- or variant thereof with any combination of substituents R$_1$, R$_2$, R$_3$, R$_4$, and R$_5$.

In the above two formulas, R$_1$, R$_2$, R$_3$, R$_4$, and R$_5$ are independently selected from the group consisting of: hydrogen; halogen; hydroxy, nitro, cyano, isocyano, thiocyano, isothiocyano, ($C_1$-$C_6$)alkyl; halo($C_1$-$C_6$)alkyl; phenyl($C_1$-$C_6$)alkyl, phenyl being optionally substituted with halogen, ($C_1$-$C_3$)alkyl, halo($C_1$-$C_3$)alkyl and ($C_1$-$C_3$)alkyloxy; cyclopropyl; ($C_1$-$C_3$)alkyloxy; halo($C_1$-$C_3$)alkyloxy; alkenyl or alkynyl having up to four carbon atoms; ($C_1$-$C_6$)alkylthio; C(O)OR$^1$, COR$^1$, and CON(R$^1$)$_2$, wherein R$^1$ is hydrogen, halogen, ($C_1$-$C_6$)alkyl, halo($C_1$-$C_6$)alkyl, and aryl, optionally substituted with halogen or ($C_1$-$C_6$)alkyl; azide; sulfinyl; sulfonyl; sulfonyl halide; sulfino; sulfo; thiol; and aryl or aryloxy optionally substituted halogen or ($C_1$-$C_3$)alkyl.

Switch Installation with Hydrazine-Containing Switch Reagents

A general scheme for modifying a protein or peptide having a least one glutamine residue with a hydrazine group-containing metal-cleavable reagent according to the method of the present technology is shown below.

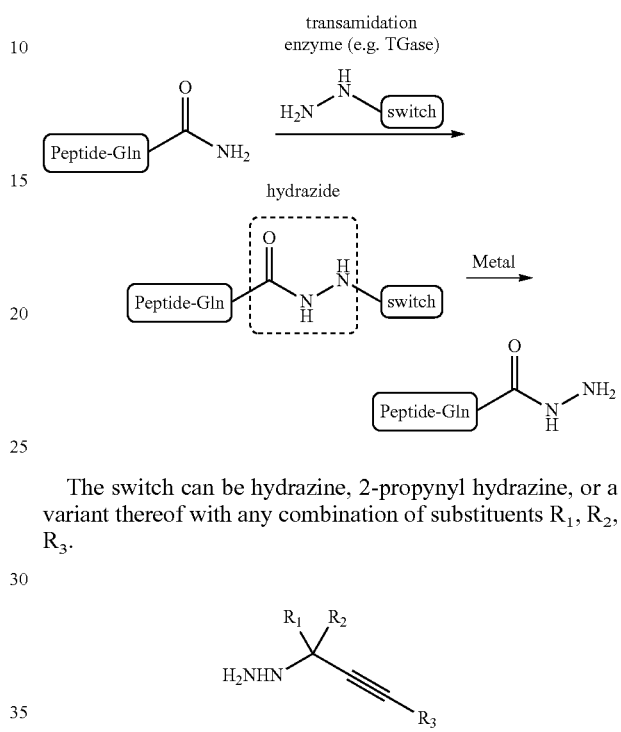

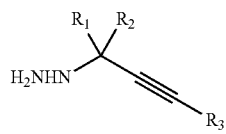

The switch can be hydrazine, 2-propynyl hydrazine, or a variant thereof with any combination of substituents R$_1$, R$_2$, R$_3$.

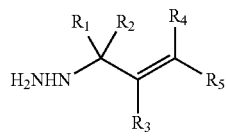

Alternatively, the switch can be hydrazine, 2-propenyl hydrazine, or a variant thereof with any combination of substituents R$_1$, R$_2$, R$_3$, R$_4$, and R$_5$.

In the above two formulas, R$_1$, R$_2$, R$_3$, R$_4$, and R$_5$ (as the case may be) are independently selected from the group consisting of: hydrogen; halogen; hydroxy, nitro, cyano, isocyano, thiocyano, isothiocyano, ($C_1$-$C_6$)alkyl; halo($C_1$-$C_6$)alkyl; phenyl($C_1$-$C_6$)alkyl, phenyl being optionally substituted with halogen, ($C_1$-$C_3$)alkyl, halo($C_1$-$C_3$)alkyl and ($C_1$-$C_3$)alkyloxy; cyclopropyl; ($C_1$-$C_3$)alkyloxy; halo($C_1$-$C_3$)alkyloxy; alkenyl or alkynyl having up to four carbon atoms; ($C_1$-$C_6$)alkylthio; C(O)OR$^1$, COR$^1$, and CON(R$^1$)$_2$, wherein R$^1$ is hydrogen, halogen, ($C_1$-$C_6$)alkyl, halo($C_1$-$C_6$)alkyl, and aryl, optionally substituted with halogen or ($C_1$-$C_6$)alkyl; azide; sulfinyl; sulfonyl; sulfonyl halide; sulfino; sulfo; thiol; and aryl or aryloxy optionally substituted halogen or ($C_1$-$C_3$)alkyl. Furthermore, the hydrazine can be $^{15}$N-labeled.

Incorporation of a switch using hydrazine chemistry can also be performed in two steps in which the first step adds a hydrazide group to the protein or peptide glutamine residue through a catalyzed transamidation reaction.

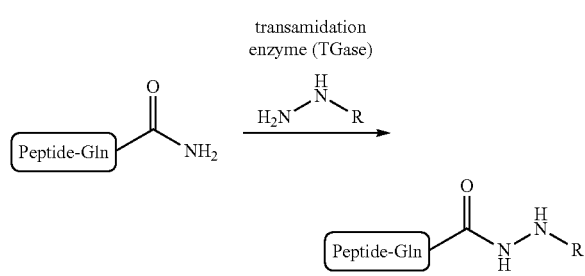

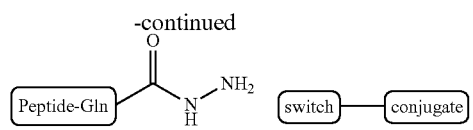

The hydrazide derivative obtained is further modified by reacting with a metal-cleavable switch containing a hydrazide-reactive functional group (several are outlined below) thereby modifying the hydrazide derivative. The original terminal hydrazide may be substituted or unsubstituted.

Switch conjugate and metal-catalyzed products are each contemplated to be useful and functional. Further, the method allows control and modulation of activity based on different yields of the installed switch (e.g., amine vs hydrazine).

Incorporation and Removal of $^{15}$N-Isotope Labeled Groups

Any metal-catalyzed switch (or switch conjugate) listed above (amine, hydrazine, hydroxylamine, etc.) can be $^{15}$N-isotope labeled. The newly generated $^{15}$N-labeled peptide and protein conjugates can be used as probes alone or

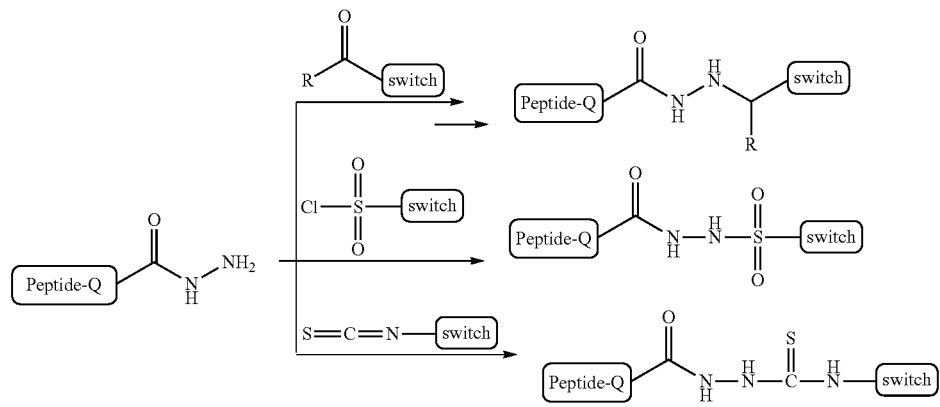

Cleavage of switch conjugate: Metal-catalyzed cleavage of a switch-conjugate linked to glutamine leads to the regeneration of the native peptide or functional equivalent of native peptide and release of the switch conjugate as shown below.

together with metal-cleavable moiety in a variety of applications. Moreover, a $^{15}$N-labeled glutamine side chain can be generated upon metal-catalyzed reaction, thus providing a method for site-specific $^{15}$N-labeling of peptides and proteins.

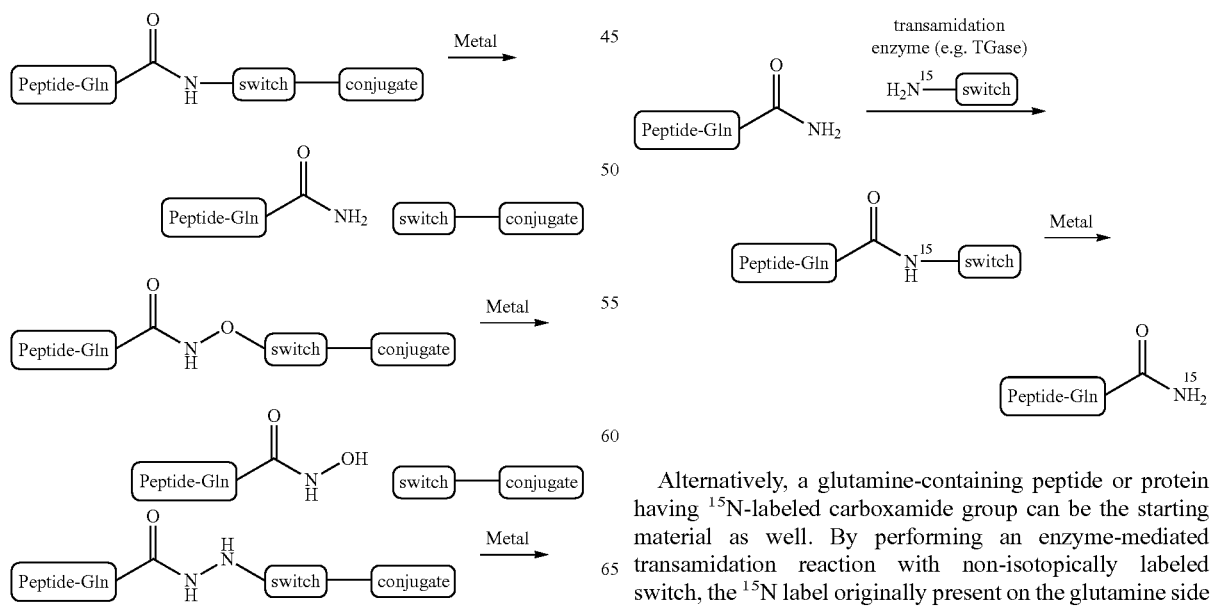

Alternatively, a glutamine-containing peptide or protein having $^{15}$N-labeled carboxamide group can be the starting material as well. By performing an enzyme-mediated transamidation reaction with non-isotopically labeled switch, the $^{15}$N label originally present on the glutamine side chain can be removed upon addition of metal ion.

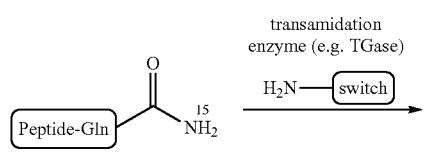

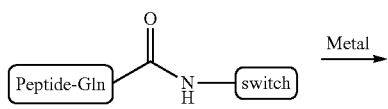

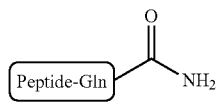

Reaction Mechanisms of Metal-Mediated Cleavage

Possible mechanisms of de-alkylation of propargyl-derivatives with Pd(0) and Pd(II) species are listed below. Pd(0) species proceeds through an allene-intermediate, and hydrolysis to restore the biomolecule (Rambabu, D et al., 2013; Wang, J et. al., 2016). Based on analogous reactions of ethers (Liu, B et al., 2012), Pd(2+) species can also cleave C—N bond.

Pd(0) Mediated Cleavage Reaction

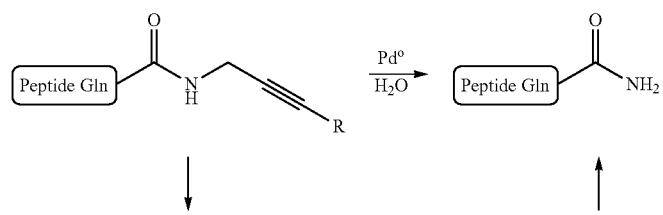

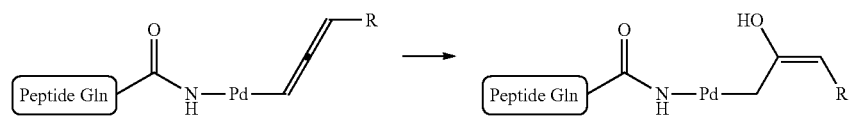

Pd(2+) Mediated Cleavage Reaction

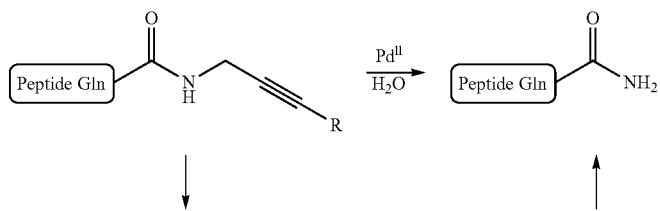

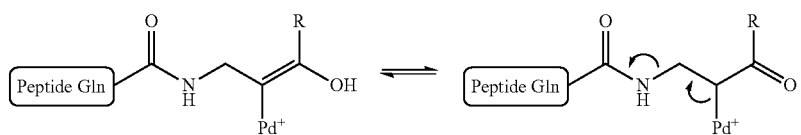

Metal for Cleavage of Modified Proteins

Metals, including copper, ruthenium, iridium, iron, or palladium have been used for bioorthogonal reactions ranging from labeling biomolecules to synthesis of organic molecules. More specifically, transition metals such as palladium, ruthenium, and iron have been utilized for several cleavage reactions within biological environment (Chankeshwara, S. V. et al., 2014; Li, J et al., 2016; Volker, T et al. 2015). Some of the applications include activation of proteins, cell engineering, and prodrug activation. For example, OspF variant, bacterial phospholyase, was activated in living cells by a palladium-mediated cleavage reaction (Li, J et al. 2014). These metals, in different forms including elemental metal, metal ions, and their complexes, can be used in the present technology.

Platinum derivatives, including those already in use, e.g., cisplatin and its derivatives used as anticancer drugs, may be used in the methods described herein as in vivo reagents for releasing chemical switches (e.g., a drug payload) in a biological environment. Examples of anticancer cisplatin derivatives can be found in Johnstone, T. C. et al., 2016, some of which are shown below.

The methods described may be used as a platform for drug development using platinum compounds including cisplatin and its derivatives (see examples listed below). These platinum drugs can be used as reagents for in-vivo metal-mediated cleavage reactions. Cisplatin and its derivatives are used to release chemical switches in biological environment. For therapeutics purpose, use of platinum-based drug synergistically to release a drug payload is envisioned. To the best of our knowledge, platinum-based moieties have not been reported in cleavage (e.g., decaging or uncaging) reactions.

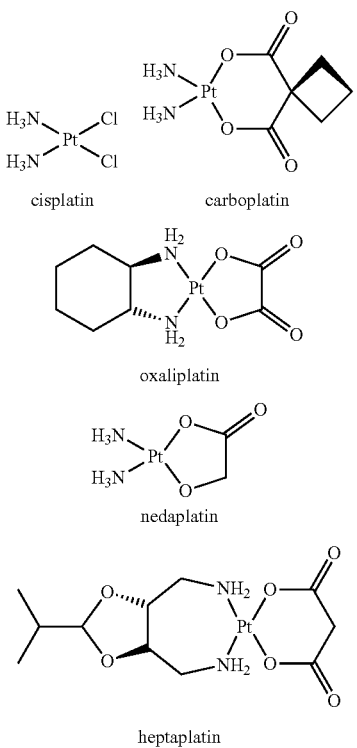

cisplatin carboplatin oxaliplatin nedaplatin heptaplatin

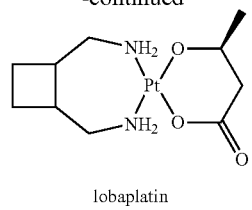

lobaplatin

Tuned, spontaneous release of native polypeptide

In addition to using external stimuli to unblock modified residue(s) in a peptide or protein, the present technology encompasses the use of rate-controlled self-cleavage under desired conditions, restoring the native polypeptide.

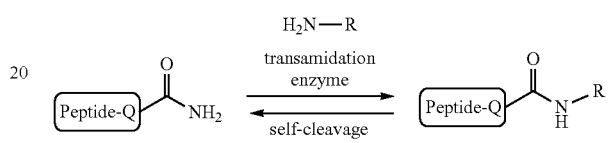

The amine-containing reagent that modifies the protein or peptide is designed such that it will undergo self-cleavage under certain conditions through an elimination-like reaction at a rate appropriate for the intended application. Importantly, a molecular "trigger" can optionally be incorporated to prevent self-cleavage until certain conditions are imposed on the construct. By changing the chemical nature of the modifying reagent, the rate and method of initiation of self-cleavage can be tuned for diverse applications.

Such a construct is desirable for a broad range of applications, including extended-release therapeutic formulations that enable release of an active ingredient at a controlled rate and/or in certain physiological or cellular milieu. Although many extended release formulations are known and are widely used to modulate the biological half-life of pharmaceuticals, none relying on reversible modification of a glutamyl amide has been reported. In the present technology, the polypeptide, the conjugated moiety, or both can be active ingredients and produce a desired effect on a system. In addition, the modified polypeptide can undergo changes in its properties at a controlled rate and/or in response to a stimulus, allowing, among others, development of environment-responsive materials, e.g., sensors (e.g., nanoscale sensors).

Examples of conditions that could cause decomposition include but are not limited to physiological temperature, pH, exposure to cellular enzymes (e.g., an esterase), and ionic strength. Such conditions would be imposed by the milieu in which this construct is used, and would result in the gradual release of the native polypeptide. The kinetics and mechanism of decomposition could be varied by using different substituents in the modifying reagent. By tuning the nature of the groups and the conditions, the design of systems with decomposition half lives in the range of seconds to hours to weeks to years is envisioned.

Mechanisms of decomposition include but are not limited to the two shown in the schemes below. These species may be generated via other transformations, e.g., chemo-enzymatic transformations, photolysis, and metal-mediated cleavage as commonly known in the art of prodrugs and controlled release, or they may themselves lead to species which undergo further transformations.

Mechanism 1: Aryl-1,n-Elimination (n=4, 6, 8, Etc. 1,4- and 1,6-Elimination Shown)

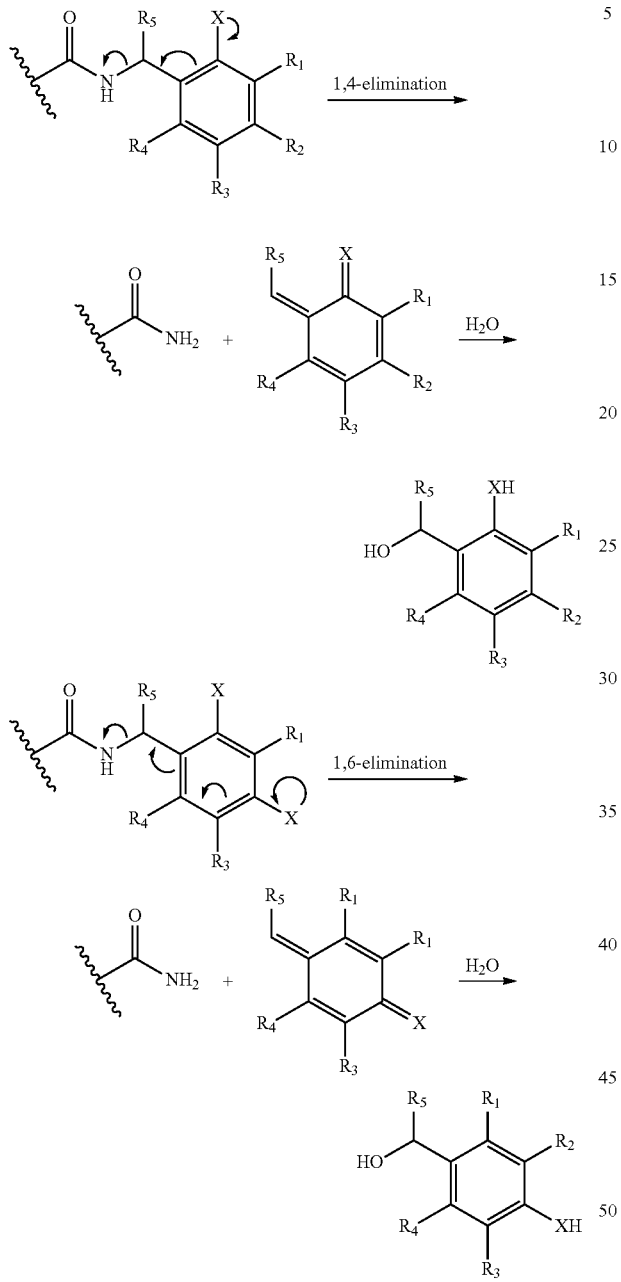

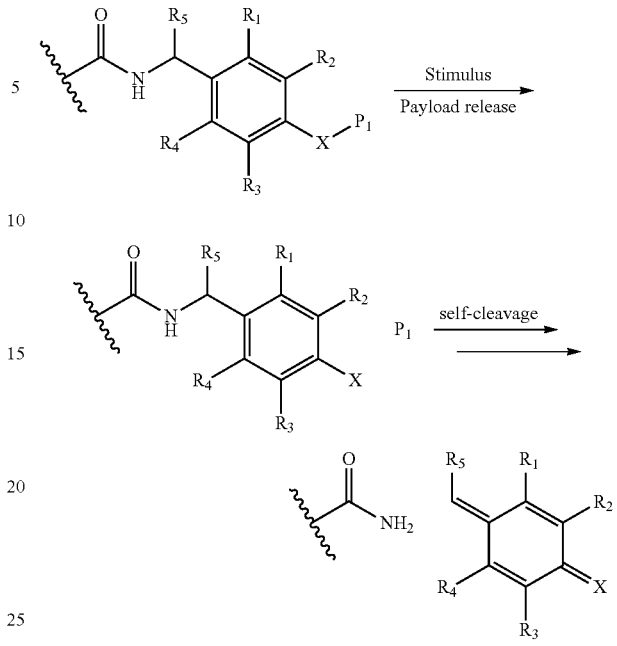

Mechanism 1 involves an elimination from an aromatic moiety with an electron-donating heteroatom X, such as oxygen, nitrogen, sulfur, phosphorus, or selenium. This mechanism is well known in the art of drug release and antibody-drug conjugates. The byproduct is a quinone methide-type species that is quenched by ambient water to give a benzylic alcohol.

By masking the electron-donating atom X with a cleavable group, P1, a payload can be released in response to various stimuli, concurrent to the initiation of self-cleavage. The blocking group can also be an active payload that is released in response to stimulus.

The linkage $X$-$P_1$ can comprise a variety of functional groups, including but not limited to ether, ester, carbonate, carbamate, alkylamine, dialkylamine, amide, urea, thioester, thioether, and hydroxylamine allowing ample tuning of chemical properties, trigger conditions and rates of cleavage.

In one prototypical embodiment, the amine-containing reagents used to generate this construct are the ortho and para isomers of (aminomethyl)phenol:

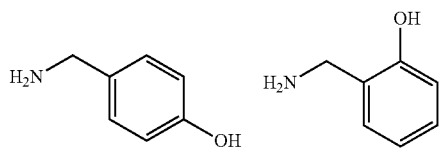 [SMILES: NCc1ccc(O)cc1 ; NCc1ccccc1O]

In another embodiment, the electron-donating phenol can be masked as a labile group such as an ester, cleavage of which triggers self-cleavage:

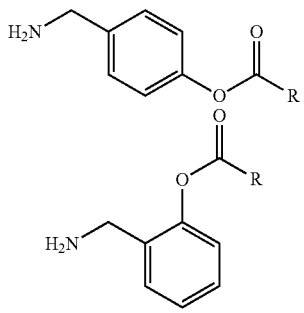

In another embodiment, the electron-donating group X is sulfur or nitrogen, affording additional opportunity for substitution and customization.

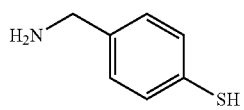

Note that a nitrogen can be substituted up to two times, allowing for further customization and tuning of the properties of the group. Shown is a dimethoxy derivative, one typical electron-rich embodiment.

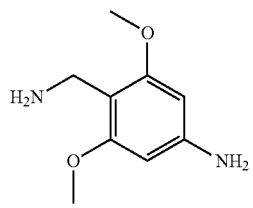

In another embodiment, the trigger for self-cleavage is the hydrolysis of a glucuronic acid moiety by the enzyme beta-glucuronidase. This mechanism has been employed in advanced drug delivery preparations (see Renoux et. al., Chem. Sci. 2017, 8, 3427-3433). The functionality is installed with an amine-containing reagent similar to the one below:

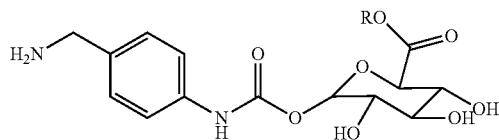

in which R represents the possibility of using a glucuronic ester to delay enzymatic cleavage until it is hydrolyzed to the free acid.

Upon enzyme recognition of the free acid, the glycosidic bond is cleaved, exposing a free carbamate which spontaneously decarboxylates to release the self-cleavage group:

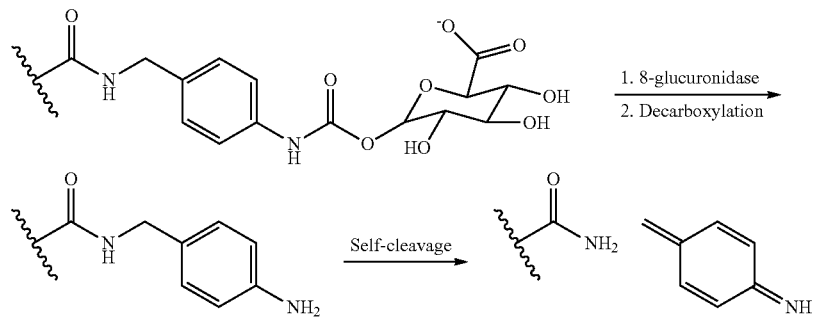

The reagents required for each of these embodiments are simple, stable, and largely commercially available compounds.

With several sites available for customization (denoted by $R_1$-$R_5$ above), this system provides ample opportunity for tuning reactivity. While the glutamine side chain amide is a relatively poor leaving group, as shown above, the N-(o-nitrophenethyl)-caged glutamine may be uncovered via a photolysis process, the key step of which involves a similar long-range elimination process on an aci-nitro methide with the glutamine amide as leaving group:

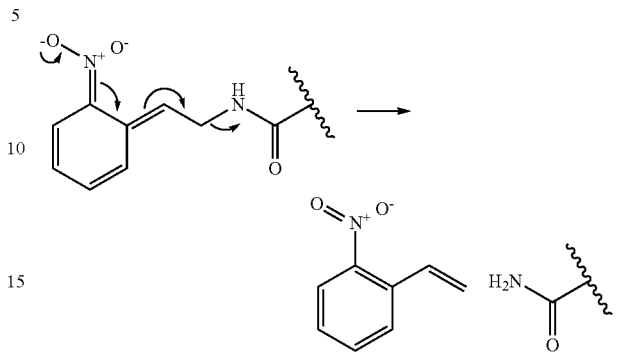

The effects of different structures and triggers on the rate of this type of elimination reaction have been reviewed for phenol leaving groups (see Alouane et. al., Angew. Chem. Int. Ed. 2015, 54, 7492-7509). Substituents $R_1$-$R_4$ on the aromatic core can include diverse electron-donating and electron-withdrawing groups, according to the desired rate and payload to deliver. Also known are substituted heterocyclic derivatives such as pyridines and pyrimidines. Also known are fused polycyclic aromatic derivatives such as phenanthrene, coumarinyl derivatives, and styrenyl derivatives that undergo 1,8-elimination (X=oxygen, nitrogen; LG=leaving group):

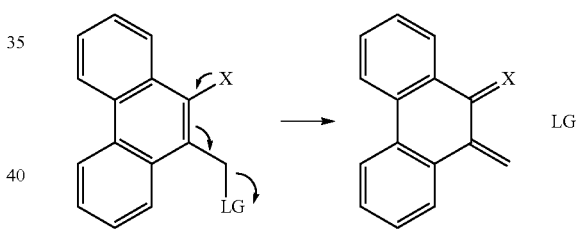

-continued

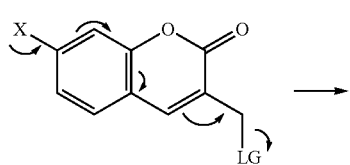

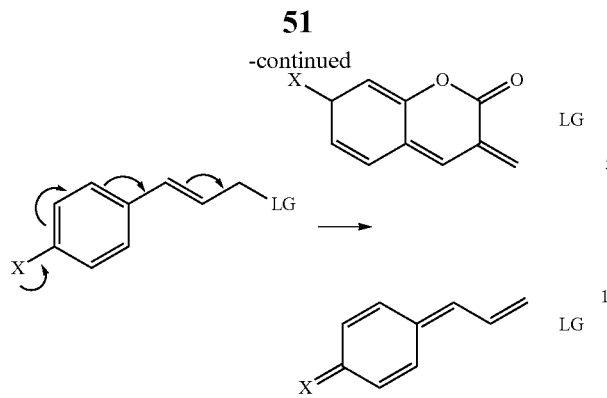

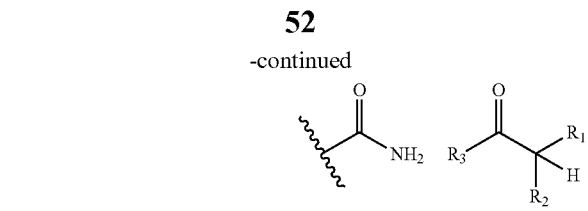

With phenolic, carbamate and amino leaving groups, these systems as well as others have been shown to undergo self-cleavage with half-lives ranging from several milliseconds to nearly 30 hours, a span of four orders of magnitude. As mentioned before, the glutamyl amide's lower proficiency as a leaving group may raise the half-lives observed when these same systems are applied in the present technology, providing half-lives extending in the longest cases to months or years. These timescales are desirable for drug formulations and materials applications.

As expected from basic mechanistic organic chemistry, the rate of elimination tends to increase with increasing electron-donating substituents on the aromatic core, and with decreasing aromaticity of the core. Thus, placing several electron-donating substituents (e.g., methoxy) on the aromatic core provides some of the fastest rates, and pyridine, pyrimidine, or polycyclic aromatic groups also result in faster self-cleavage.

Mechanism 2: Alkyl-1,2-Elimination Followed by Hydrolysis of Enamide

Mechanism 2 involves two distinct steps to release the native polypeptide and a carbonyl-containing byproduct. In the first step, a proficient leaving group X, such as sulfone, sulfoxide, selenone, selenoxide, halogen, phosphate, sulfate, acyloxy, or others is eliminated along with the adjacent proton to generate an N-vinyl amide derivative, also known as an enamide. In the second step, the enamide is cleaved hydrolytically to restore the native glutamine residue and a carbonyl-containing byproduct. The hydrolysis of enamides is well-known and has been shown to proceed by the following acid-catalyzed mechanism in aqueous solution (see Csizmadia et. al., *J. Am. Chem. Soc.* 1979, 101:4, 979-979 for details).

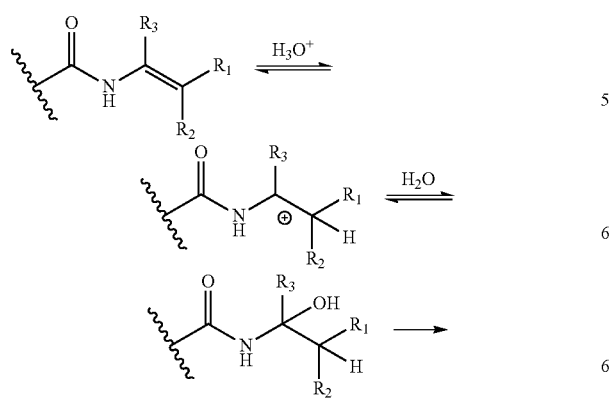

In one typical embodiment, two amine-containing reagents are shown below, each of which contains a sulfone leaving group:

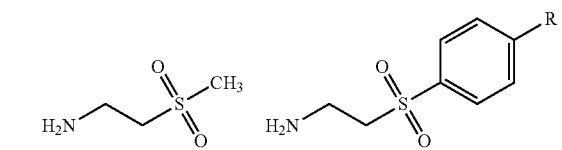

The R group provides an opportunity for diverse payloads or substituents.

In another embodiment, the elimination is triggered by oxidation of a heteroatom to provide a more competent leaving group, for example of a sulfide to a sulfoxide, a selenide to a selenoxide, or an amine to an amine oxide:

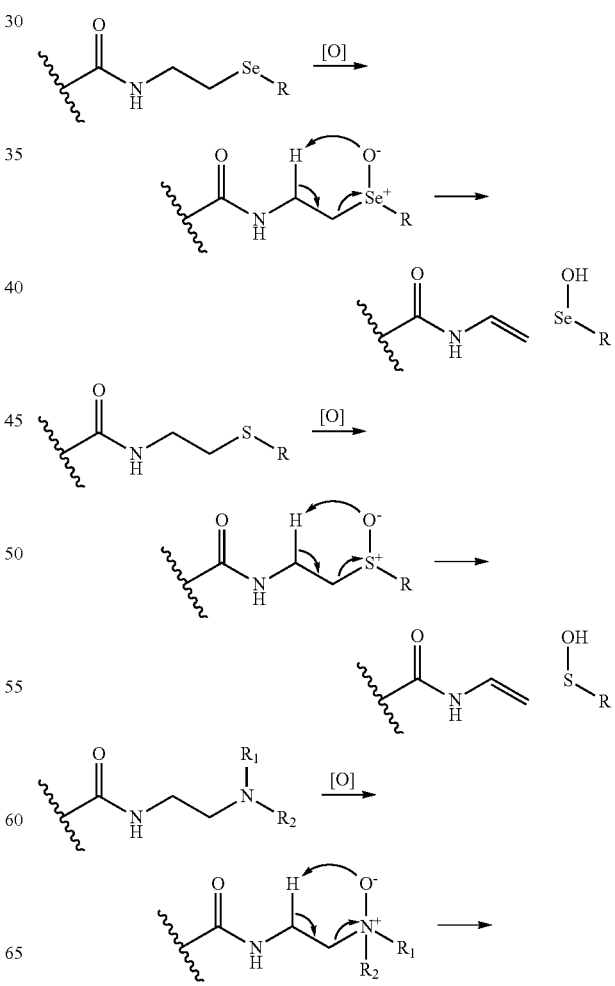

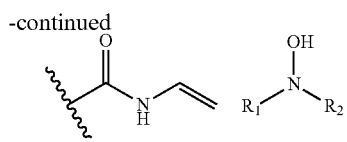

The oxidant can come from diverse sources in the system of interest, including but not limited to air, reactive oxygen species (ROS) in living cells, oxidizing metals, and oxidizing chemicals such as bleach and hydrogen peroxide. The rate of oxidation can be tuned to the desired application, providing a third tunable handle for the system in addition to the elimination and hydrolysis steps. Both sulfoxide and selenoxide eliminations have been shown to occur under physiological conditions (see Zhou et. al., 1997 and Fishkin et. al., 2011), so this method is believed to be especially applicable to biological sensing, drug delivery and other medicinal and biological fields. Amine-containing reagents containing sulfoxides, selenoxides and N-oxides can also be directly employed in the present technology.

With two separate eliminations proceeding by distinct mechanisms, the present technology offers the opportunity to tune the rates of both steps, and also to release two different payloads over the course of restoring the native polypeptide. For example, the initial leaving group, X in the general scheme, could be conjugated to a small molecule of interest, including but not limited to a fluorophore or a small molecule drug. The elimination of X would concomitantly release this conjugate at a controlled rate. The resulting enamide could contain on its substitution sites, $R_1$-$R_3$ in the general scheme, another payload of interest, which would then be released by hydrolysis at a different controlled rate. Importantly, the second release step occurs strictly after the first release step. This method provides a unique order-enforced mechanism for rate-controlled payload release in diverse systems. For example, in the scheme below, $P_1$ and P2 represent the payloads and the leaving group is a substituted phenylsulfone group. The native protein or peptide is also released after the second step, restoring its original activity or function.

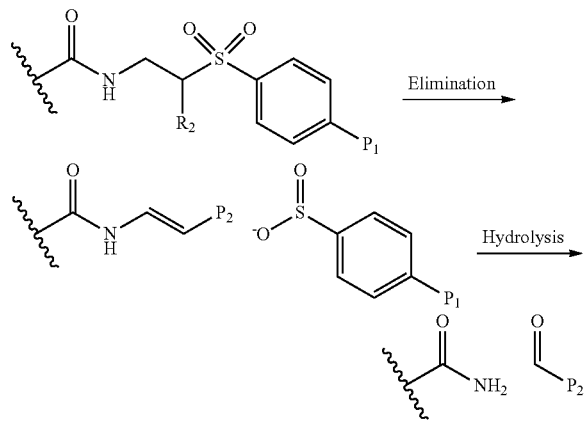

In a variation on the above embodiments, a hydrazine or hydroxylamine derivative of the amine-containing reagents outlined above can be used to form a hydrazide or hydroxamic acid derivative, respectively. When the construct undergoes self-cleavage by Mechanism 1 or 2, the product will be an optionally substituted hydrazide or a hydroxamic acid, not an amide:

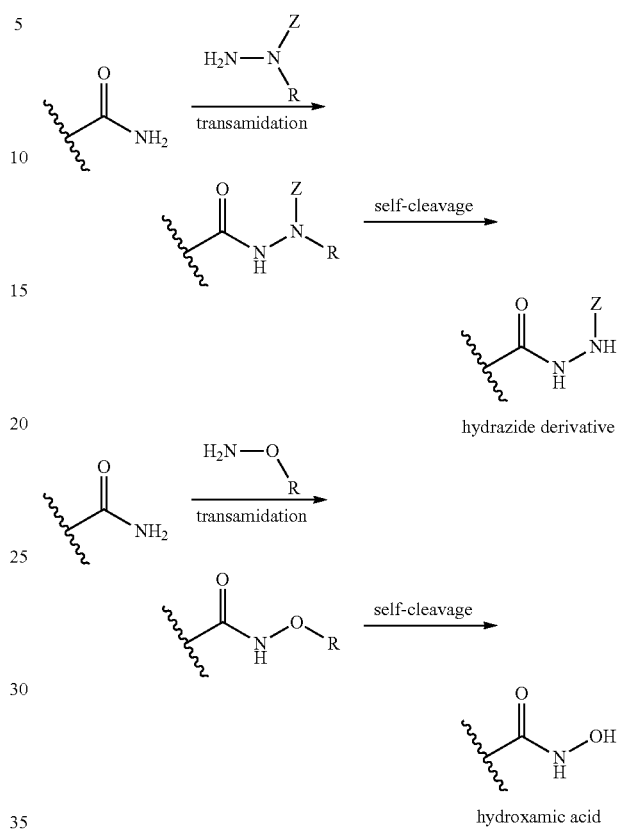

This embodiment enables further tuning of the kinetics of self-cleavage, as the hydrazide and hydroxamic acid groups are significantly more acidic than the amide group, and should be more facile leaving groups. Additionally, the product of self-cleavage is a very close homologue to the native peptide or protein, differing by the substitution of a hydrazide or hydroxamic acid for an amide on a glutamine sidechain. This change may allow introduction of new properties in the system, such as changing the isoelectric point and metal chelating properties. Also possible are other chemistries that cleave the N—N or N—O bond to regenerate the native amide. It should be noted also that the hydrazide can have a substituent that is retained upon self-cleavage, represented by Z in the above schematic diagram.

The opportunity for diverse substituents on the groups described, and the several mechanisms by which self-cleavage may occur, allows for extensive tuning of kinetics. Some of these mechanisms are well-known and used as release strategies in prodrugs and controlled-release entities, such as antibody-drug conjugates. In the present technology, both the released native polypeptide and the released blocking group could exert an effect on the surrounding system. Thus, this technology is envisioned to provide rate-controlled release of a polypeptide and a blocking entity in a system of interest. The present technology may be applied both in biological contexts, such as cell culture and organisms, and in other contexts, such as materials and sensors. The associated reagents and enzymes are commercially available and well-known, adding to the practicality of the method.

Enzymes

Transglutaminase enzymes: Transglutaminases (TGases, E.C. 2.3.2.13) are a large family of enzymes that catalyze an acyl group transfer reaction in which glutamine substrates act as acyl-donors and various nucleophiles (including amines) act as acyl-acceptors (Folk et al 1966). Microbial and several mammalian transglutaminase isoforms have been well studied, with tissue and microbial transglutaminases each displaying broad acyl acceptor substrate specificity (Gnaccarini et al 2012, Gundersen et al 2014). Each transglutaminase isoform displays unique substrate specificity requirements, thus providing an excellent platform for site-specific conjugation applications (Ohtsuka et al. 2000). A consensus sequence around glutamine substrates is yet to be described. Factors such as flexibility and solvent accessibility are believed to greatly influence substrate recognition. As a result, only one or a few of the glutamine residues in a protein or peptide may act as a substrate and be modified by a nucleophile, giving rise to selective modification of the protein or peptide. If the modified glutamine is near the active site, the modification would likely lead to alteration of the activity of the protein or peptide. Removal of the modifying group by, for example, photolysis, or a metal-catalyzed reaction, or by other means as described herein, would regenerate the protein or peptide.

Figure 14:
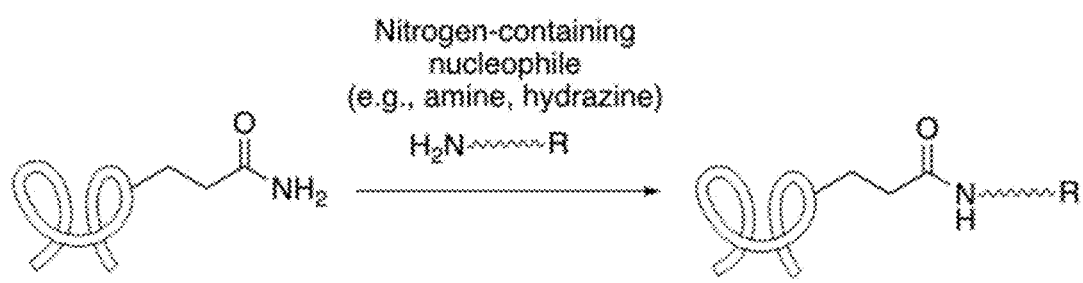
FIG. 14 shows a general scheme depicting a transglutaminase-mediated transamidation reaction with a nitrogen-containing nucleophile.

A general scheme depicting a transglutaminase-mediated transamidation reaction with a nitrogen-containing nucleophile is shown in FIG. 14.

A variety of different transglutaminase enzymes can be used in the technology, including microbial (e.g., bacterial) TGase, mammalian tissue TGase, and engineered TGase (Malešević, M. et al., 2015; Zhao, X. et al., 2010).

In addition to transglutaminases, other enzymes (e.g. proteases, esterases) capable of installing switches or switch-conjugates via acyl transfer reactions are also known. For example, a protease can be used to incorporate a switch into a protein or peptide as shown below using the prototypical serine protease trypsin, which forms an acyl-enzyme intermediate C-terminal to arginine or lysine residues.

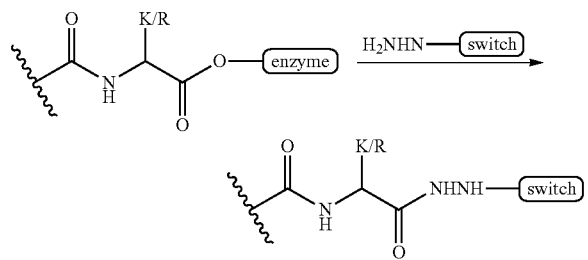

A multi-step approach also can be used. For example, unsubstituted hydrazine can be used to generate an unsubstituted hydrazide derivative of the protein or peptide, which can be further derivatized. Moreover, the nucleophile does not necessarily have to be hydrazine as depicted above. Other suitable reagents include amines, hydroxylamines and nitrogen containing nucleophiles.

Transglutaminase Substrates

A large number of proteins have been characterized as transglutaminase substrates (http:/genomics.dote.hu/wiki/index.php/Main Page). These proteins are suitable for use with the present technology. Examples of the proteins that have been shown to be transglutaminase substrates are listed below.

Substrate Proteins for FXIIIa

Intercellular adhesion molecule 2; Keratin, type II cytoskeletal 1; Laminin; Lipoprotein A (FXIIIa); Lumican; Mannan-binding lectin serine protease 1; Melanocyte protein PMEL; Monocyte differentiation antigen CD14; Myosin (FXIIIa); N-acetylglucosamine-1 phosphotransferase subunit gamma; N-acetylmuramoyl-L-alanine amidase; Neurogenic locus notch homolog protein 2; Osteopontin (FXIIIa); Peptidase inhibitor 16; Phosphatidylinositol-glycan-specific phospholipase D; Phospholipase A2 (FXIIIa); Phospholipid transfer protein; Plasma kallikrein; Plasma protease C1 inhibitor; Plasminogen (FXIIIa); Platelet glycoprotein Ib alpha chain; Platelet-derived growth factor AB; Procarboxypeptidase B/U (FXIIIa); Properdin; Protein HEG homolog 1; Protein MENT; Protein synthesis initiation factor 5A (FXIIIa); Proteoglycan 4; Selenoprotein P; Semenogelin I, II; Serum paraoxonase/arylesterase 1; Sex hormone-binding globulin; SPARC-like protein 1; Tetranectin; Thrombospondin; Transforming growth factor-beta-induced protein ig-h3; Uteroglobin (FXIIIa); Vasorin; Vinculin; Vitamin D-binding protein; Vitamin K-dependent protein C; Vitamin K-dependent protein S; Vitamin K-dependent protein Z; Vitronectin (FXIIIa); Von Willebrand factor.

Substrate Proteins for TG1 Keratinocyte Transglutaminase

Beta actin (TG1); Desmoplakin (TG1); Elafin (TG1); Filaggrin (TG1); Huntingtin (TG1); Involucrin (TG1); Keratin intermediate filaments (TG1); Loricrin (TG1); Microtubule-associated protein tau; S100A10 (TG1); S100A11 (TG1); Small proline rich proteins SPRs-1 (TG1); Small proline rich proteins SPRs-2 (TG1); Small proline rich proteins SPRs-3 (TG1).

Substrate Proteins for TG2 Tissue Transglutaminase 40S ribosomial protein Sal; Acidic proline rich protein; Aconitase; ACTH; Actin (TG2); ADP/ATP translocase 1; Aldolase A; Alpha lactalbumin (TG2); Alpha synuclein; Alpha-2 macroglobulin receptor; Alpha-2 plasmin inhibitor (TG2); Alpha-2-HS-glycoprotein; Alpha-ketoglutarate dehydrogenase; Alpha-tubulin; Amyloid beta A4 peptide; Androgen receptor; Angiocidin; Ankyrin; Annexin I; Antileukoproteinase; Apolipoprotein B-100; Apolipoprotein E (TG2 Substrate); Arginase I; AT-rich interactive domain-containing protein 1A; Ataxin-1; ATP synthase; Band 3 anion transport protein; Band 4.1 protein; Bcr—Breakpoint cluster region; Beta casein; Beta endorphin; Beta lactoglobulin; Beta tubulin (TG2); Beta-2-microglobulin; Betaine-homocysteine S-methyltransferase; BiP protein; Bone sialoprotein; C-CAM; $C_1$ inhibitor; Calbindin; Calpain; Carboxypeptidase B2; Caspase-3; Cathepsin D; CD38; Clathrin heavy chain; Collagen (TG2); Complement $C_3$; Crystallin; Cyclic Thymosin beta 4; Cytochrome C; Decorin; Deoxyribonuclease γ; Dihydropyrimidinase-like 2 protein; DNAJA1 (TG2 substrate); Dual leucine zipper-bearing kinase (DLK); EGF Receptor; Elafin (TG2); Elongation factor 1α; Elongation factor 1γ; Enolase; Envelope glycoprotein gp120; Envelope glycoprotein gp41; Ephrin A; Eucaryotic initiation factor 4F (eIF-4F); Exendin 4; Ezrin-Radixin-Moesin binding phosphoprotein 50; F-box only protein; Fatty acid synthase; Fibrillin-1; Fibrinogen alpha chain (TG2); Fibrinogen gamma chain (TG2); Fibronectin (TG2); Filamin 1; Fructose 1,6-bisphosphatase; Galectin 3; Gliadin; Gliadoralin A; Glucagon; Glutathione S-transferase; Glyceraldehyde-3-phosphate dehydrogenase; Hepatitis C virus core protein; Histamine; Histatin; Histone H1 (transglutaminase); Histone H2B type 1-C/E/F/G/I (TG2 substrate); Histone octamer (transglutaminase); HIV-1 aspartyl protease (TG2); Hsp 27; Hsp60; Hsp70; Hsp70/90 organizing protein; Hsp90; Human Clara-cell 10 kDa protein; Huntingtin (TG2); Hyphal wall protein-1; Ig kappa chain C region; Immunoglobulin gamma-1 heavy chain; Immunoglobulin heavy constant delta; Immunoglobulin heavy constant gamma 3; Importin β1 subunit; Insulin; Insulin-like growth factor I; Insulin-like growth factor-binding protein-1; Insulin-like growth factor-binding protein-3 (transglutaminase); Inter-alpha-inhibitor; Lactoylglutathione lyase; Lamin A, C; Latent transforming growth factor beta binding protein 1; Lipoprotein A (TG2); Low-density lipoprotein receptor-related protein 6; Melittin; Microfibril-associated glycoprotein (MAGP); Midkine; Myelin basic protein; Myosin (TG2); Neurofilament proteins; Neuropeptide Y; NF-kappa-B inhibitor alpha; Nidogen; Nuclease sensitive element binding protein-1; Nucleophosmin; Orexin B; Osteonectin; Osteopontin (TG2); Parkin; Periphilin; Periplakin; Phosphoglycerate dehydrogenase; Phospholipase A2 (TG2); Phosphorylase kinase; Plasminogen (TG2); Plasminogen activator inhibitor-2; *Plasmodium falciparum* liver stage antigen-1; Platelet-derived growth factor subunit B; Procarboxypeptidase B/U (TG2); Prohibitin; Protein kinase C delta type; Protein synthesis initiation factor 5A (TG2); RAP—Alpha-2 macroglobulin related protein; Retinoblastoma protein (transglutaminase); Rho associated, coiled coil, containing protein kinase 2; RhoA; S100A10 (TG2); S100A11 (TG2); S100A4; S100A7; Seminal vesicle secretory protein IV; Serotonin; SNAP-25; SP1 transcription factor; Spectrin; Statherin; Substance P; Suprabasin (TG2); Synapsin 1; Synapsin I; T-complex protein 1ε subunit; Tau protein; Thymosin beta 4; Thyroglobulin; Troponin; Tumor rejection antigen-1; Ubiquitin; Uteroglobin (TG2); UV excision repair protein RAD23 homolog B; Valosin; Vasoactive intestinal peptide; VEGFR-2; Vigilin; Vimentin (TG2); Vitronectin (TG2); Y-box binding protein.

Substrate Proteins for TG3 Epidermal Transglutaminase

Cystatin A; Desmoplakin (TG3); Elafin (TG3); Envoplakin; Filaggrin (TG3); Hornerin; Huntingtin (TG3); Involucrin (TG3); Keratin intermediate filaments (TG3); Loricrin (TG3); Sciellin; Serine protease inhibitor Kazal-type 6; Small proline rich proteins SPRs-1 (TG3); Small proline rich proteins SPRs-2 (TG3); Small proline rich proteins SPRs-3 (TG3); Suprabasin (TG3).

Substrate Proteins for TG4

Seminal vesicle secretory protein 1; Seminal vesicle secretory protein 2; Seminal vesicle secretory protein 3.

Substrate Proteins for TG5

Involucrin (TG5); Loricrin (TG5); Small proline rich proteins SPRs-3 (TG5); Vimentin (TG5).

Substrate Proteins for Microbial Transglutaminase

Alpha lactalbumin; Bacteriorhodopsin; Dispase autolysis inducing protein (DAIP); Gelatin; Lysozyme C; Myosin heavy chain subfragment 1 (TGM); Phaseolin; Serotransferrin; *Streptomyces* Subtilisin and TAMEP Inhibitor; Type I collagen.

Additional TGase (not among those listed above) include: oxytocin (a neuropeptide), TAT peptide (commonly used cell-penetrating peptide), peptide derived from Lymphocytic Choriomeningitis Virus (LCMV) Glycoprotein, beta lactalbumin, beta casein, Switch Conjugates In addition to installing a switch into peptides or proteins, further derivatization of the switch to generate a 'switch-conjugate' is also contemplated. The switch-conjugate and the resulting photolytic product are expected to be functional and useful in their own rights. Installation of a switch conjugate can be achieved via a one-step or multi-step process as outlined below. Exemplary conjugates include PEG, recombinant antibody, a drug, a fluorophore, and an adjuvant One-step installation of switch-conjugate: The linkage between the switch and conjugate is generated first and the resulting switch-conjugate is then installed into a glutamine residue in proteins or peptides via direct enzyme-catalyzed transamidation reaction. Three examples are illustrated below:

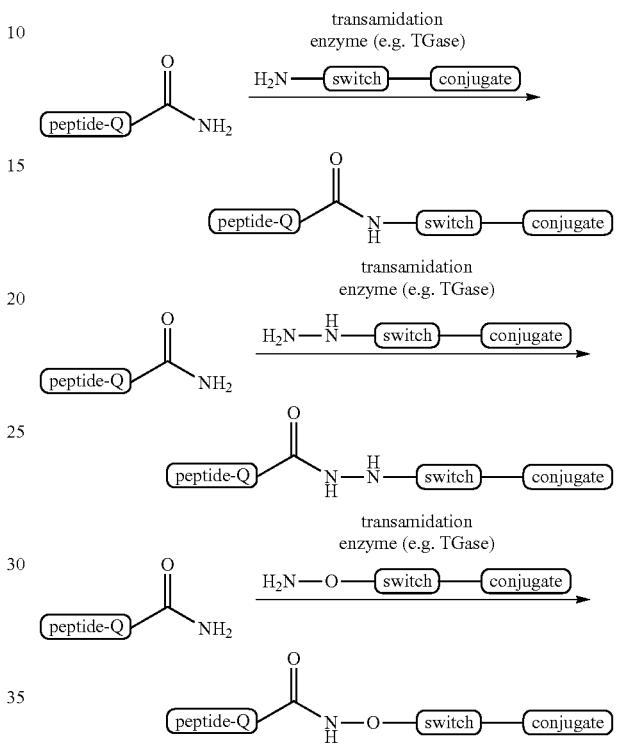

Multi-step installation of switch conjugate: The switch conjugate is installed via one of several multi-step processes. A few options are shown below:

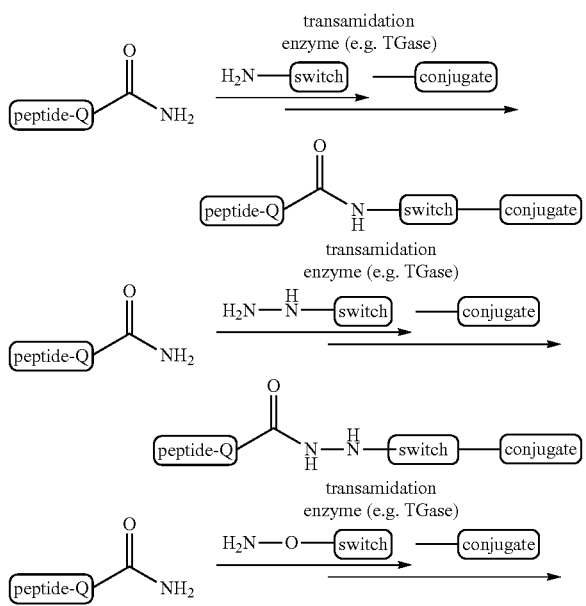

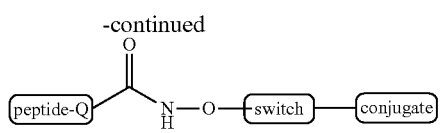

The following is an example using click chemistry to generate a switch conjugate.

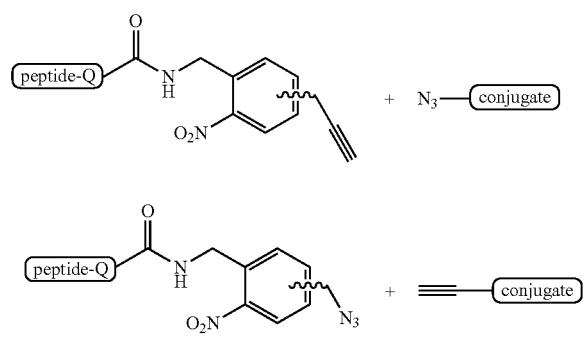

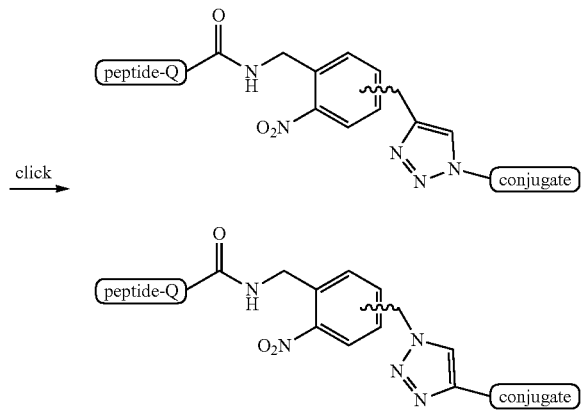

The methods of the present technology can be used to introduce an effector moiety into a system, such as a mammalian subject, which may be a human subject, or into a cell, a fermentation, a cell culture, or an industrial chemical process. An effector moiety is any chemical moiety that can be introduced as the amine-containing reagent or linked to the amine containing reagent. The effector moiety can be, for example, a protein or peptide that carries out a function where introduced, an antibody or antigen-binding fragment thereof, a therapeutic moiety such as a drug or toxin, or a labeling moiety, such as a fluorescent tag, optical tag, or radioactive tag.

The methods described in the present technology may be used for producing probes and drugs. For example, a substituent labeled with a radioisotope or an isotope suitable for NMR or PET imaging can be added to a protein or peptide via TGase, and the modified protein or peptide can be used as a probe, relying on its inherent binding affinity for a protein (e.g., a receptor) on a cell to find its target, or for a protein in circulation (e.g., an enzyme). Antibodies can be labeled and used as probes or diagnostics in this manner. A labile conjugate made with TGase by a method described herein can serve as a prodrug, being only released at a time or location chosen as part of a treatment regime for a disease. In this manner, otherwise toxic peptides or proteins can be targeted with high specificity to a target tissue or cell type (e.g., a tumor), with release only, or selectively, at the target location through one or more of the release mechanisms described above, providing on demand dosing or on demand drug release. Such methods can be used for screening drugs or identifying or characterizing their targets or receptors. The methods and compositions of the present technology may also be used in drug delivery systems, light-controlled 3D protein printing, protein printing on surfaces (e.g. microarray), antibody drug conjugates (ADCs), and IR two- or three-photon absorption. The use of caged pharmaceutical agents, such as therapeutic proteins or peptides can provide improved storage, including long term storage, with release and activation performed just prior to administering the agent. The ability to photorelease drugs, including peptides and proteins, offers the opportunity to use them in optogenetic applications and for photo stimulation. Photolabile proteins and peptides can be employed in imaging, such as bioimaging using an array of caged biomolecules, and to provide real-time imaging. Such arrays can be used as biosensors. The methods and compositions of the technology can also be utilized for in vivo applications where a reagent is administered to a subject and endogenous TGase within the subject leads to caging of certain proteins or peptides within cells or tissues of the subject.

Enzymes, including those used commercially may be caged using the present technology. Caging may be used to temporarily inactivate the enzymes which may subsequently be activated by using conditions under which the enzymes retain activity, including elevated temperature and low pH. Examples of such enzymes are: cellulase, used, e.g., in textiles for the purposes of stonewashing denim and polishing of cotton; catalase, used, e.g., in textiles for removing hydrogen peroxide; pectinase, used, e.g., in textiles for bioscouring; alpha amylase, used, e.g., in textiles for desizing at low temperatures; proteases, used, e.g., in the manufacture of baby food; and lipase, used, e.g., in biological detergents.

Many peptides that are either bioactive or have other properties making them suitable for use in treating diseases may also be modified using the present technology. Included among such peptides are multifunctional and cell penetrating peptides, and peptide drug conjugates (Fosgerau, K. et. al., 2015), as well as neuropeptides and bioactive peptides (Fricker, 2012 and Perboni et al., 2013). Proteins of therapeutic value may also be modified using the present technology. Such proteins include, but are not limited to antibody drug-conjugates (Dennler et al., 2014), anticoagulants, enzymes, erythropoietin, hormones, interferons, interleukins, monoclonal antibodies, thrombolytic agents, vaccines (see Walsh, 2014 for details). Furthermore, toxins such as cholera toxin subunit B, recombinant pertussis toxin, and botulism antitoxin, diphtheria toxin (Wang et al., 2017), and immunotoxins (Mazora et al., 2018 and Alewine et al., 2015) may also be used with the technology described herein.

Using the aforementioned proteins and peptides in the technology described herein, a large number of diseases and conditions may be treated. These diseases and conditions encompass several therapeutic areas including oncology, infectious disease, neurology, metabolism and endocrinology, dermatology, gastroenterology, inborn errors, cardiology, ophthalmology, pulmonary diseases, rheumatology, hematology, and bone diseases. Specific diseases include cancer, neurodegenerative disorders, inflammation-related conditions, hemophilia, metabolic disorders, diabetes, neutropenia, cystic fibrosis, and migraine.

EXAMPLES

Example 1. Chemo-Enzymatic Site-Specific Modification and Reversal Using Photolysis Chemo-enzymatic site-specific modification of glutamine (Gln or Q) using a transamidation enzyme (e.g. transglutaminase or engineered transglutaminase) is shown in the schematic diagram below (also see FIG. 1A). Modification of glutamine residue present in peptides or proteins is achieved through enzyme-mediated transamidation of an amine-containing photocaging reagent. Photolysis regenerates the native peptide or protein and releases the photocaging group.

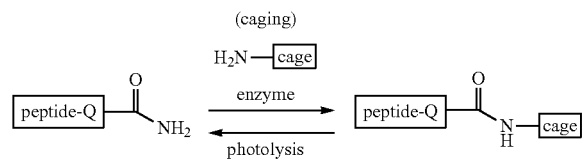

The degree of modification can be controlled by optimizing reaction conditions (pH, temperature, time, enzyme concentration, photocaging reagent concentration, etc.). The photocaging group can then be removed upon photolysis with UV light irradiation (>300 nm).

To demonstrate the feasibility of this approach two photolabile reagents, 2-nitrobenzylamine and 2-(2-nitrophenyl)ethan-1-amine were tested in microbial transglutaminase-mediated transamidation reactions using beta-casein, a 24 kDa phosphoprotein found in cow's milk, as the glutamine-containing protein. Neither of these photolabile amines has been previously utilized as transglutaminase substrates. As an intrinsically disordered protein, beta-casein is one of the most commonly tested transglutaminase substrates, with multiple glutamines reported that can serve as acyl donors.

Using mass spectrometry analysis, it was established that both reagents can be used to modify glutamines following transamidation with microbial transglutaminase. Following proteolysis with thermolysin, it was confirmed that photocaging had occurred.

Alpha gliadin peptide LGQQQPFPPQQPY (SEQ ID NO: 3), (amino acids 31-43; 1.5 kDa) was also used as the glutamine-containing peptide in certain experiments. This peptide is also reported to be a transglutaminase substrate.

Experimental

Modification of beta casein using microbial TGase and 2-nitrobenzylamine: To an aqueous solution of bovine beta-casein (1 mg/mL, 40 µM) in 0.1 M Tris-HCl (pH 8), 2 µL of 0.5 M dithiothretol, 6 µL of 1.0 M 2-nitrobenzylamine and 0.01 units microbial TGase (Ajinomoto ACTIVA-TI, final 50 units mTGase/g beta casein) were added in a final reaction volume of 200 µL. Transamidation reaction mixture was briefly vortexed and then incubated at 37° C. for 24 hrs. The enzyme was inactivated by briefly incubating the transamidation mixture at 80° C. for 5 minutes.

Modification of beta casein using microbial TGase and 2-(2-nitrophenyl)ethan-1-amine: To an aqueous solution of bovine beta-casein (1 mg/mL, 40 µM) in 0.1M Tris-HCl (pH 8), 2 µL of 0.5 M dithiothretol, 6 µL of 1.0 M 2-(2-nitrophenyl)ethan-1-amine and 0.01 units microbial TGase (Ajinomoto ACTIVA-TI, final 50 units mTGase/g beta casein) were added in a final reaction volume of 200 µL. Transamidation reaction mixture was briefly vortexed and then incubated at 37° C. for 24 hrs. The enzyme was then inactivated by briefly incubating the transamidation mixture at 80° C. for 5 minutes.

Thermolysin digestion of modified beta casein protein: Prior to proteolytic digestion, excess unreacted amine was removed from the beta casein protein using Amicon Ultra centrifugal filters (MWCO 10,000 Da). Briefly, 100 µL of modified beta-casein was mixed with 300 µL of 0.1 M Tris-HCl (pH 8) and centrifuged at 14,000×g for 5 minutes at room temperature. Fresh 0.1M Tris-HCl buffer (300 µL, pH 8) was added to the concentrated modified protein sample and centrifuged under previously described conditions. This process was repeated an additional three times. Samples were recovered by flipping filter device upside down and centrifuging at 1000×g for 2 minutes. To 100 µL of this modified beta casein protein (1 mg/mL), 5 µL of thermolysin endoproteinase (1 mg/mL, Promega) and 2 µL of 50 mM CaCl$_2$ were added. Digestion mixture was briefly vortexed and incubated at 80° C. for 3 hrs. Of note, as beta-casein contains no cysteine residues, typical reduction and alkylation of cysteines prior to proteolysis was not performed.

Sample desalting and spotting for MALDI-TOF-MS analysis: The proteolytic mixtures were desalted using C18 ZipTip desalting columns prior to analysis. Briefly, 10 µL of thermolysin digested beta casein mixture was mixed with 0.5 µL of an aqueous 5% trifluoroacetic acid (TFA) solution. C18 ZipTip was initially equilibrated with 100% acetonitrile (ACN) followed by aqueous 0.1% TFA. Sample was loaded onto equilibrated C18 ZipTip, washed with aqueous 0.1% TFA (5×10 µL) and finally eluted into 4 µL of 0.1% TFA in 50:50 ACN/water. The mixtures were mixed 1:1 with 10 mg/mL alpha-Cyano4-hydroxycinnamic acid (CHCA) in a solution of 0.1% trifluoroacetic acid (TFA) in 50:50 ACN/water and dried at room temperature prior to MALDI analysis. Mass spectrometry was performed on a 5800 MALDI-TOF/TOF analyzer (Applied Biosystems, Waltham, Mass.) operated in positive ion mode. System was calibrated using a peptide standard mixture from Anaspec (Des-Arg1-Bradykinin, Angiotensin 1, neurotensin) prior to analysis of digest mixtures.

Photolysis of 2-nitrobenzylamine caged beta casein peptides: Thermolysin digested beta casein sample modified with 2-nitrobenzylamine (50 µL) was placed in a cuvette for photolysis studies. Orel Instruments housing with an Osram 150 W XBO xenon short-arc lamp, fitted with Schott WG-320 filter to eliminate UV light below 320 nm, was used for photolysis. UV light irradiation was performed for 20 minutes. The sample was analyzed by MALDI-TOF-MS to determine extent of d photo-cleavage.

Modification with 2-nitrobenzylamine

Figure 2A:
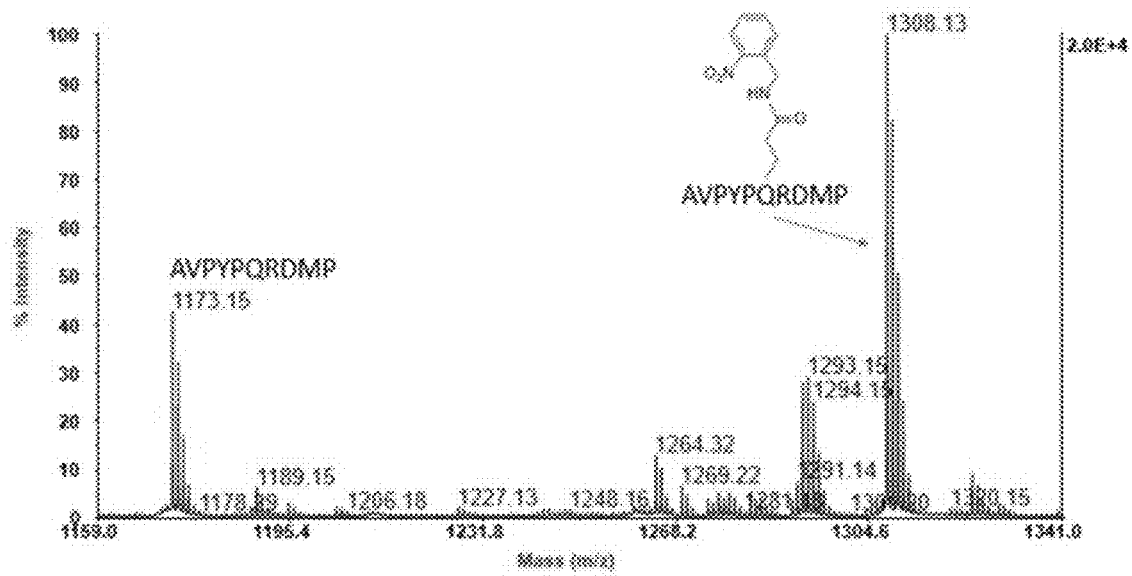
FIG. 2A is a positive mode MALDI-TOF-MS spectrum showing mTGase-mediated transamidation of beta casein with 2-nitrobenzylamine as the acyl acceptor. Transamidation reaction was carried out in 0.1M Tris-HCl (pH 8.0) for 24 hrs at 37° C. using 20 mM of 2-nitrobenzylamine and 50 units mTGase/gram of beta-casein. Singly charged unmodified beta casein thermolysin peptide (AVPYPQRDMP (SEQ ID NO:1); amino acids 177-186) is observed at m/z 1173.15 (theoretical m/z 1173.57) and modified glutamine product is observed at m/z 1308.13 (AVPYPQRDMP; SEQ ID NO: 1; theoretical m/z 1308.74).
Figure 2B:
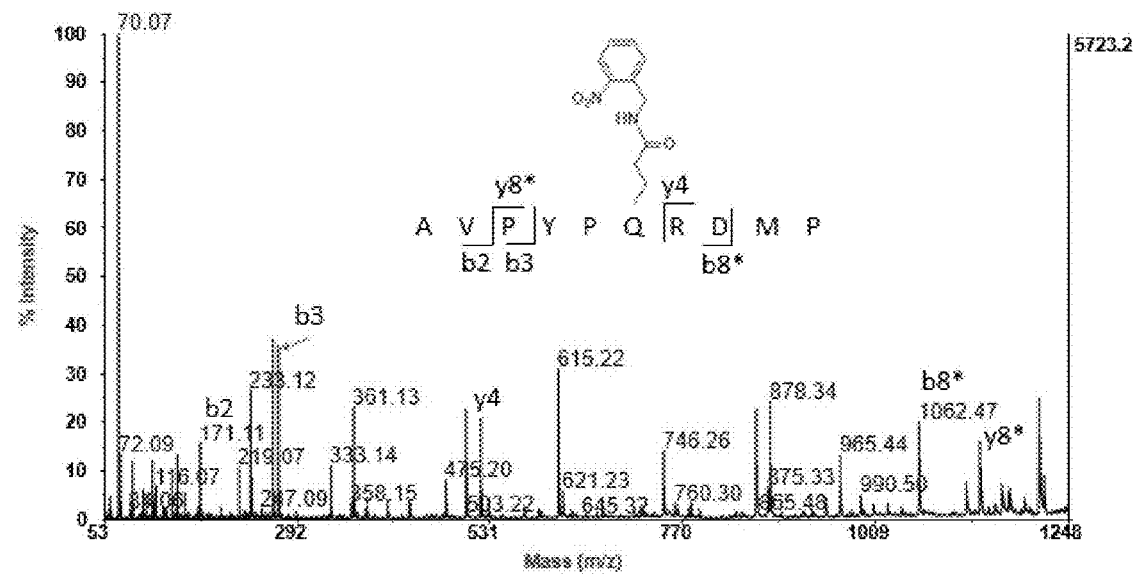
FIG. 2B is a MALDI-TOF-MS/MS spectrum of fragment ions derived from the singly charged precursor having m/z 1308.13 (modified glutamine product). Fragment ions that include modified Q are indicated by "*".

2-Nitrobenzylamine was found to be incorporated into beta casein based on MALDI-TOF mass spectrometry results (FIG. 2A). The spectrum shows singly charged unmodified beta casein thermolysin peptide (AVPYPQRDMP; SEQ ID NO:1; amino acids 177-186) at m/z 1173.15 (theoretical m/z 1173.57) and modified glutamine product at m/z 1308.13 (AVPYPQRDMP; SEQ ID NO: 1; theoretical m/z 1308.74). Analysis of fragment ions derived from the singly charged precursor having m/z 1308.13 confirmed modification of the Q in the peptide (FIG. 2B). Fragment ions confirming the presence of modified Q are indicated with "*".

Another set of experiments were carried out to test regeneration of glutamine containing peptide following photolysis. MALDI-TOF-MS spectra shown in FIGS. 4A and 4B demonstrate photolysis efficiency of beta casein thermolysin peptides AVPYPQRDMP (SEQ ID NO: 1) and AVPYPQRDMPIQA (SEQ ID NO: 2) modified with 2-nitrobenzylamine. The spectrum before photolysis is shown in FIG. 4A. Peaks at m/z 1308.13 and 1620.20 correspond to the caged AVPYPQRDMP (SEQ ID NO: 1) and AVPYPQRDMPIQA (SEQ ID NO: 2) peptides, respectively. Photolysis led to complete removal of the 2-nitrobenzyl group (FIG. 4B).

Figure 3A:
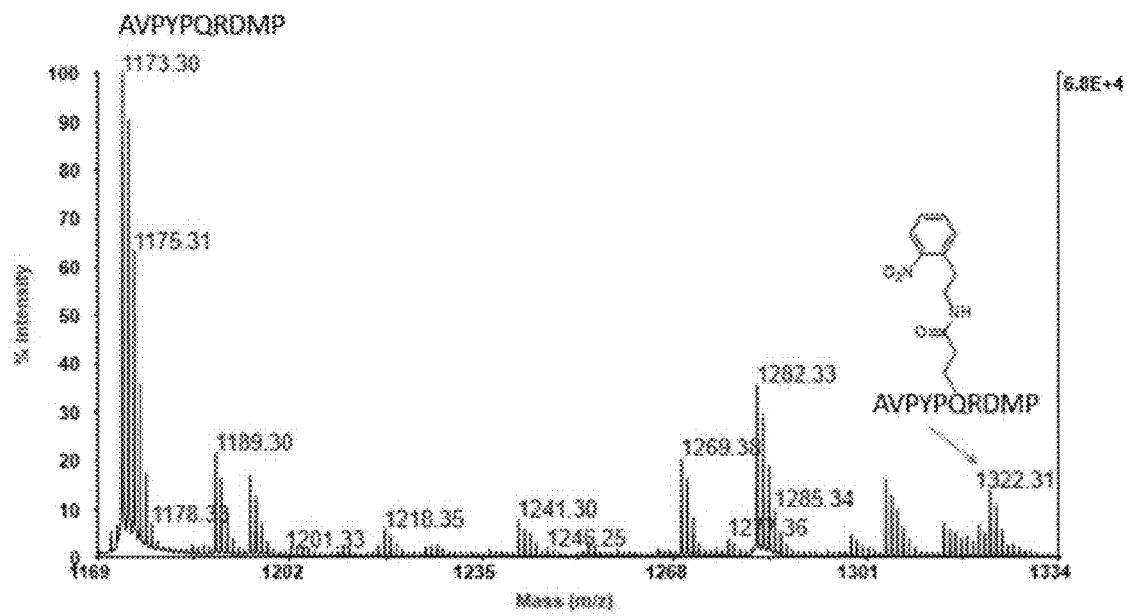
FIG. 3A is a positive mode MALDI-TOF-MS spectrum showing mTGase-mediated transamidation of beta casein using 2-(2-nitrophenyl)ethan-1-amine as the acyl acceptor. Transamidation was carried out in 0.1M Tris-HCl (pH 8.0) for 24 hrs at 37° C. using 20 mM of 2-(2-nitrophenyl)ethan-1-amine and 50 units mTGase/gram of beta-casein. Singly charged unmodified beta casein thermolysin peptide is observed at m/z 1173.30 (AVPYPQRDMP (SEQ ID NO:1), theoretical m/z 1173.57) and the modified glutamine product is observed at m/z 1322.13 (AVPYPQRDMP, SEQ ID NO: 1; theoretical m/z 1322.74).
Figure 3B:
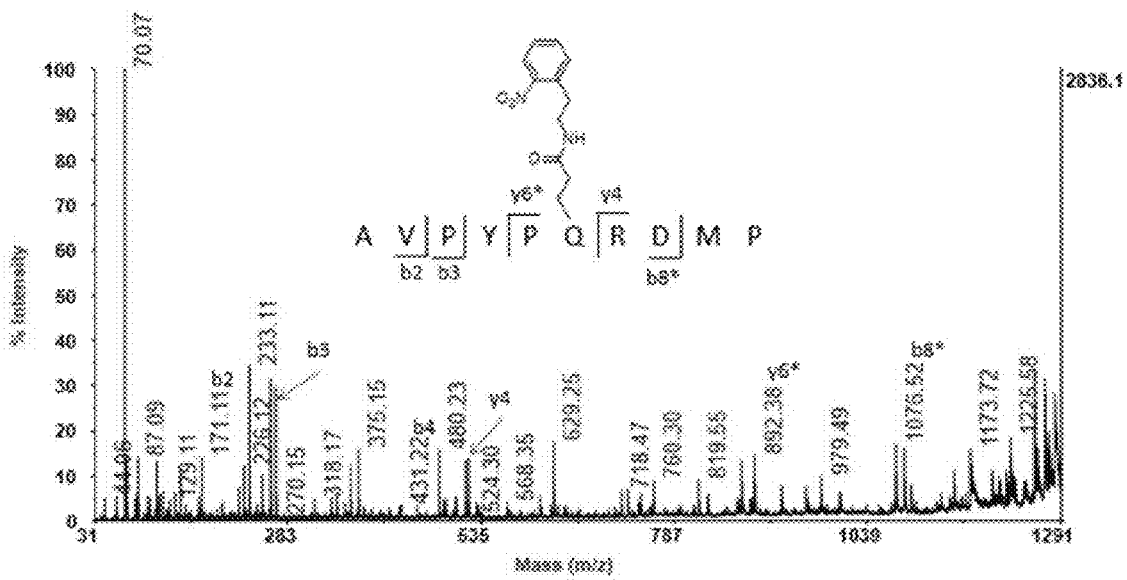
FIG. 3B is a MALDI-TOF-MS/MS spectrum of fragment ions derived from the singly charged precursor having m/z 1322.13. Fragment ions that include modified Q are indicated with (*).
Figures 12A, 12B, 12C:
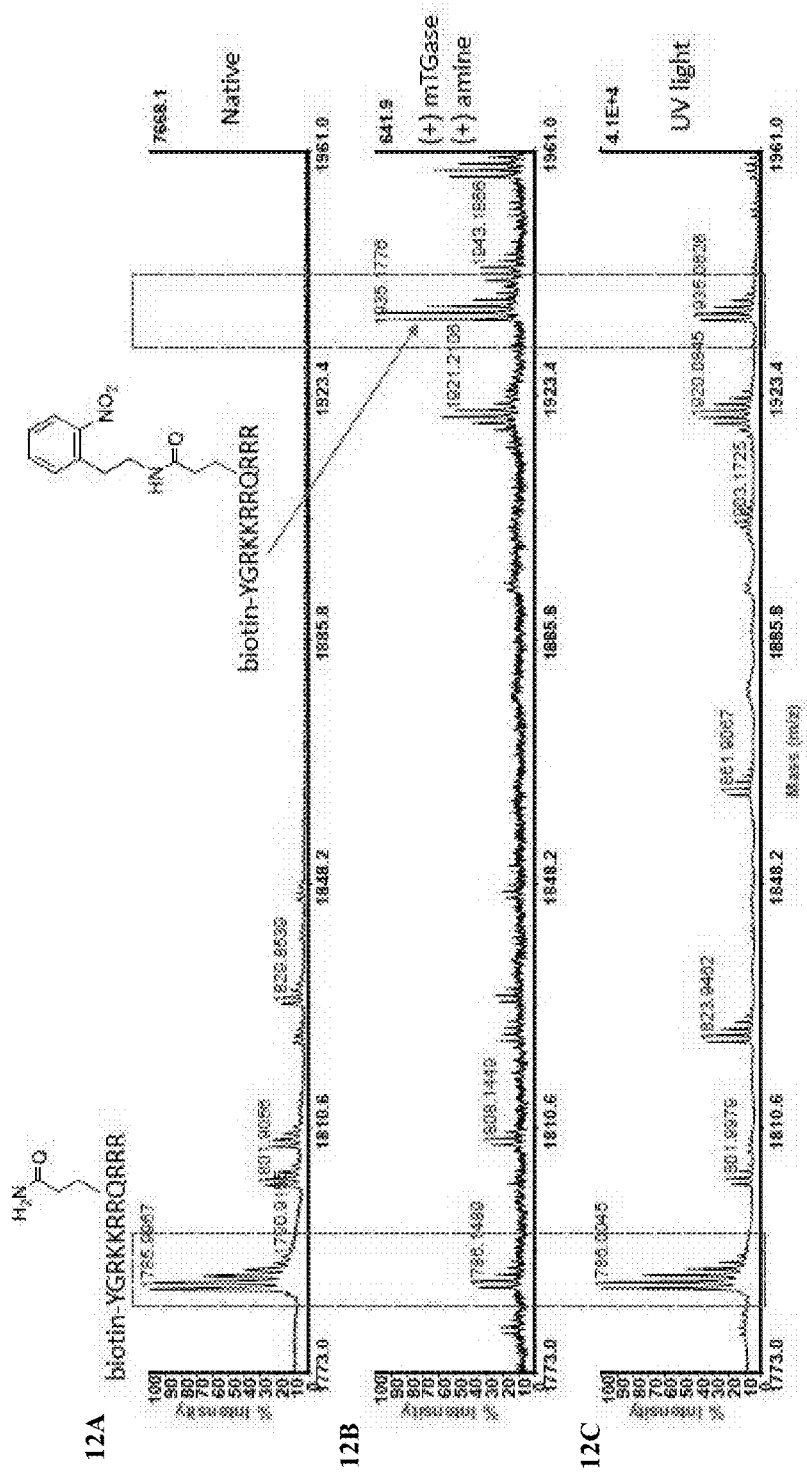
FIG. 12A is a MALDI-TOF-MS spectrum of biotin-TAT peptide biotin-YGRKKRRQRRR (SEQ ID NO:4). The peak at m/z 1785.99 corresponds to the native peptide (theoretical m/z 1786.03, mass difference 0.04).
FIG. 12B is a MS spectrum of biotin-TAT peptide modified with a nitrophenylethyl group using mTGase. The peak at m/z 1935.17 corresponds to the modified peptide (theoretical m/z 1935.18, mass difference 0.01).
FIG. 12C is a MS spectrum of nitrophenylethyl modified biotin-TAT peptide following photolysis. Intensity of the peak at m/z 1786.00 is increased and that at m/z 1935 is reduced, indicating removal of nitrophenylethyl group and regeneration of the native peptide.

Modification with 2-(2-nitrophenyl)ethan-1-amine 2-(2-Nitrophenyl)ethan-1-amine was shown to be incorporated into beta casein using MALDI-TOF mass spectrometry (FIG. 3A). Singly charged unmodified beta casein thermolysin peptide was observed at m/z 1173.30 (AVPYPQRDMP, SEQ ID NO: 1, theoretical m/z 1173.57) and modified glutamine product was observed at m/z 1322.13 (AVPYPQRDMP, SEQ ID NO: 1, theoretical m/z 1322.74). Analysis of fragment ions derived from the singly charged precursor having m/z 1322.13 confirmed modification of Q in the peptide (FIG. 3B). Fragment ions confirming the presence of modified Q are indicated with "*". See also FIGS. 12A-12C for the modification of biotin-TAT peptide biotin-YGRKKRRQRRR (SEQ ID NO: 4) with 2-(2-nitrophenyl)ethan-1-amine and the removal of the modifying group.

Modification with Nitrophenylpropylamine

Figures 10A, 10B, 10C:
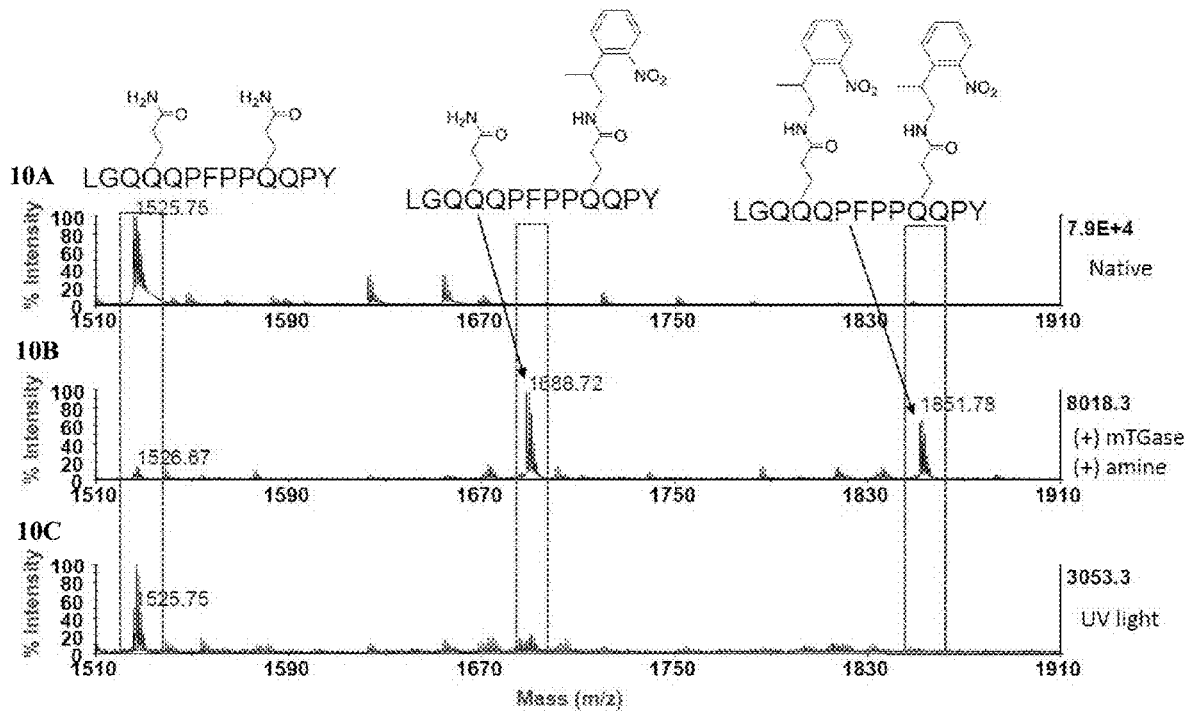
FIG. 10A is a negative mode MALDI TOF-MS spectrum of alpha gliadin peptide LGQQQPFPPQQPY (SEQ ID NO:3) (see peak at m/z 1525.748).
FIG. 10B is a negative mode MALDI-TOF-MS spectrum of alpha gliadin peptide following mTGase-catalyzed transamidation reaction with nitrophenylpropylamine. Two major products having peaks at m/z 1688.72 and m/z 1851.78 were observed.
FIG. 10C is a negative mode MALDI-TOF-MS spectrum of modified alpha gliadin peptide (FIG. 10B) subjected to photolysis for 20 minutes at 320 nm to regenerate alpha-gliadin peptide (see peak at m/z 1525.75 for the regenerated peptide).

Nitrophenylpropylamine was also used for modifying a glutamine containing peptide and subsequently regenerating the peptide by photolysis (FIGS. 10A-10C). Alpha gliadin peptide LGQQQPFPPQQPY (SEQ ID NO: 3) was used in this study. The peak at m/z 1525.748 shown in the MALDI TOF-MS spectrum of FIG. 10A corresponds to the peptide. The spectrum of the peptide following transamidation is shown in FIG. 10B. Two major products were observed at m/z 1688.72 and m/z 1851.78 corresponding, respectively, to modification of one or two glutamine residues. Photolysis led to regeneration of the native peptide (FIG. 10C, peak at m/z 1525.75).

Modification with 4,5-dimethoxy-2-nitrophenylethylamine

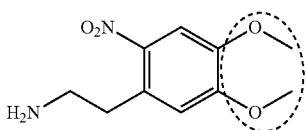

Figures 11A, 11B:
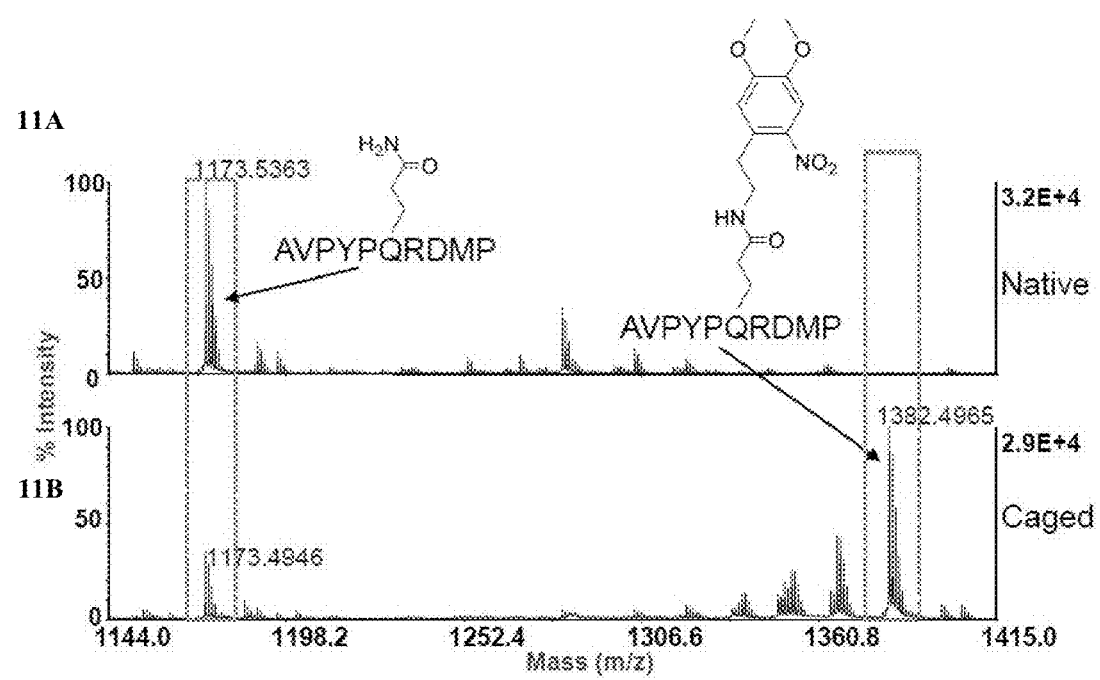
FIG. 11A is a positive mode MALDI TOF-MS of unmodified beta casein thermolysin peptide AVPYPQRDMP (SEQ ID NO:1) (amino acids 177-186; see peak at m/z 1173.53).
FIG. 11B is a mass spectrum of 4,5-dimethoxynitrophenylethyl-modified beta casein (peak at m/z 1382.49).
Figure 11C:
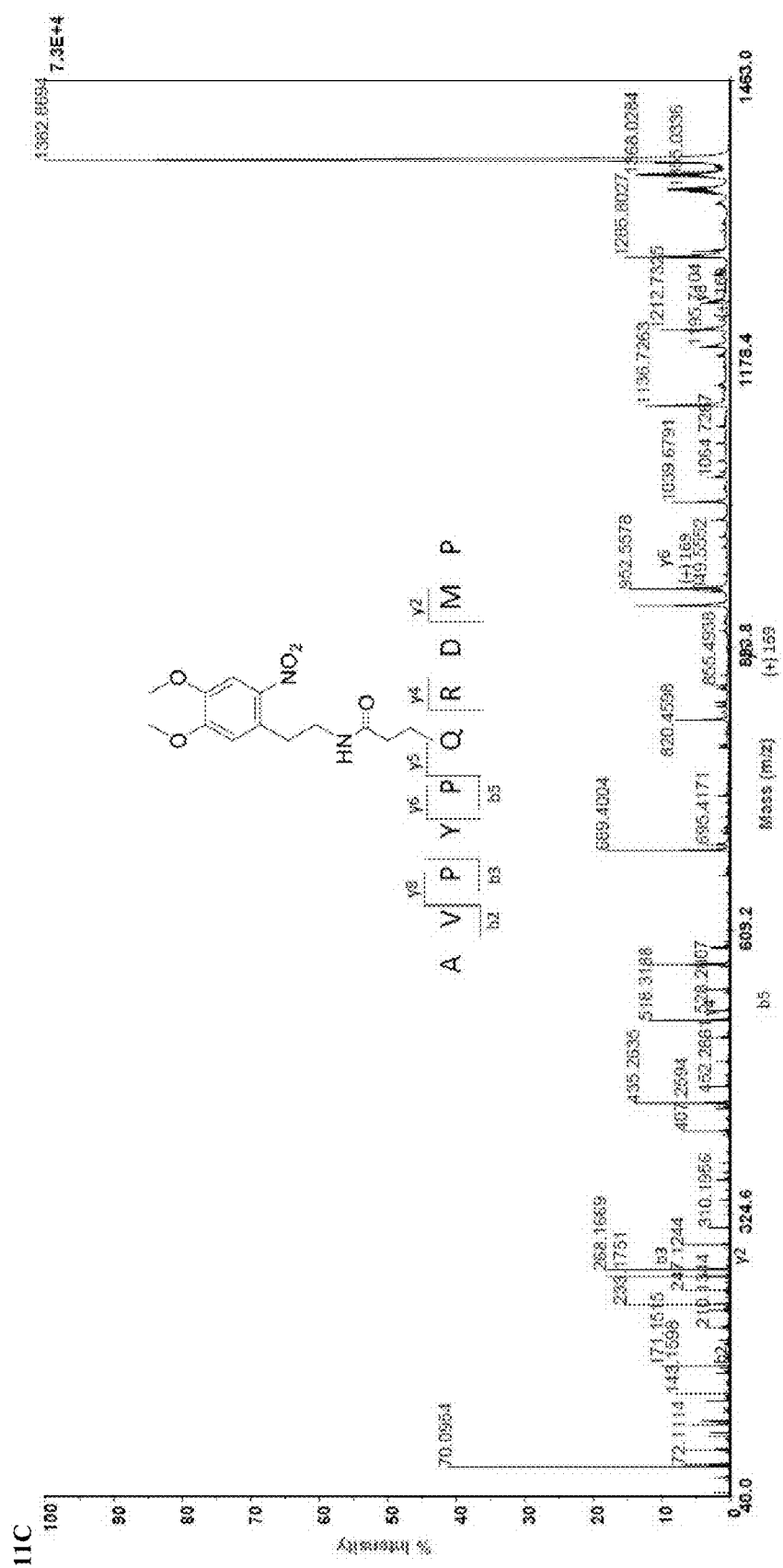
FIG. 11C shows SEQ ID NO: 1 and is a collision-induced dissociation (CID) MS/MS spectrum of precursor having m/z 1382.49 confirming modification of Q182. Fragment ions y5, y6, and y8 display the expected (+) 169 Dalton shift for 4, 5-dimethoxynitrophenylethyl caging group on the glutamine side chain. Additional unmodified ions (y2, y4, b2, b3, and b5) further confirm that modification occurs on the glutamine residue.

The chromophore 4,5-dimethoxy-2-nitrophenylethylamine allows for multiphoton photolysis, which has the advantages of less photo damage, deeper tissue penetration and high resolution using focused light. This chromophore was used to modify beta casein. As seen in FIG. 11A, the peak at m/z 1173.53, corresponds to unmodified beta casein thermolysin peptide AVPYPQRDMP, SEQ ID NO: 1, (amino acids 177-186). The mass spectrum of 4, 5-dimethoxynitrophenylethyl-modified beta casein is shown in FIG. 11B (peak at m/z 1382.49). Modification of Q182 was confirmed by the CID MS/MS (FIG. 11C) of precursor modified beta casein thermolysin peptide. The expected (+) 169 dalton shift for 4, 5-dimethoxynitrophenylethyl group on the glutamine side chain can be observed in the fragment ions y5, y6, and y8. Unmodified ions (y2, y4, b2, b3, and b5) further confirm that modification occurs on glutamine.

Example 2. Chemo-Enzymatic Site-Specific Modification and Reversal Using Metal

Chemo-enzymatic site-specific installation of dynamic switches onto glutamine using a transamidation enzyme (e.g. transglutaminase or engineered transglutaminase) followed by metal-catalyzed cleavage to generate the glutamine residue is schematically shown below. The switch used for this purpose is an amine-containing metal-cleavable reagent. Cleavage is achieved by the addition of metal ions, which regenerates native peptide or protein and releases the metal-cleavable group.

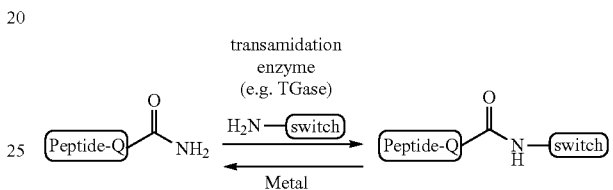

Degree of incorporation of the metal-cleavable group can be controlled by optimizing reaction conditions (pH, temperature, time, enzyme concentration, nitrogen-containing reagent concentration, etc.).

The feasibility of this approach was tested by using two metal-cleavable reagents, propargylamine and 3-phenylprop-2-yn-1-amine, in microbial transglutaminase-mediated transamidation reactions. Alpha gliadin peptide LGQQQPFPPQQPY (SEQ ID NO: 3), (amino acids 31-43) was used as the glutamine-containing peptide. The transglutaminase reaction mixture included 100 mM Tris buffer (pH 8), 1 mg/ml or 70 μM gliadin peptide $^{31}$LGQQQPFPPQQPY$^{43}$, (SEQ ID NO: 3), amines (propargylamine, 30 mM; 3-phenylprop-2-yn-1-amine, 10 mM; allylamine, 30 mM; all final concentrations), and 1 mM DTT. The reaction was initiated with 0.1 μM microbial transglutaminase and continued for 3 to 4 hours at 37° C. To remove excess unreacted reagent, each reaction mix was desalted using GE Healthcare PlusOne Mini Dialysis Kit (MWCO 1,000 Da) against 100 mM Tris at pH 8 and at room temperature for 6 hours. Each reaction mixture underwent a metal-catalyzed reaction using 167 μM of Allyl$_2$Pd$_2$Cl$_2$ (allylpalladium(II) chloride dimer) or 190 μM cisplatin for 1 to 15 hours at 37° C. Mass spectrometric analyses were carried out as described in the previous section.

Modification with Propargylamine

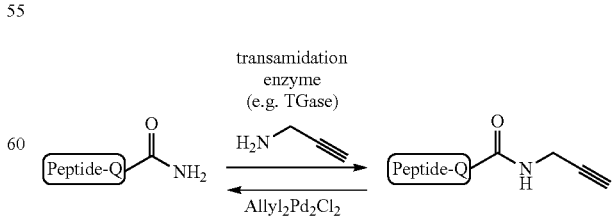

Figure 5C:
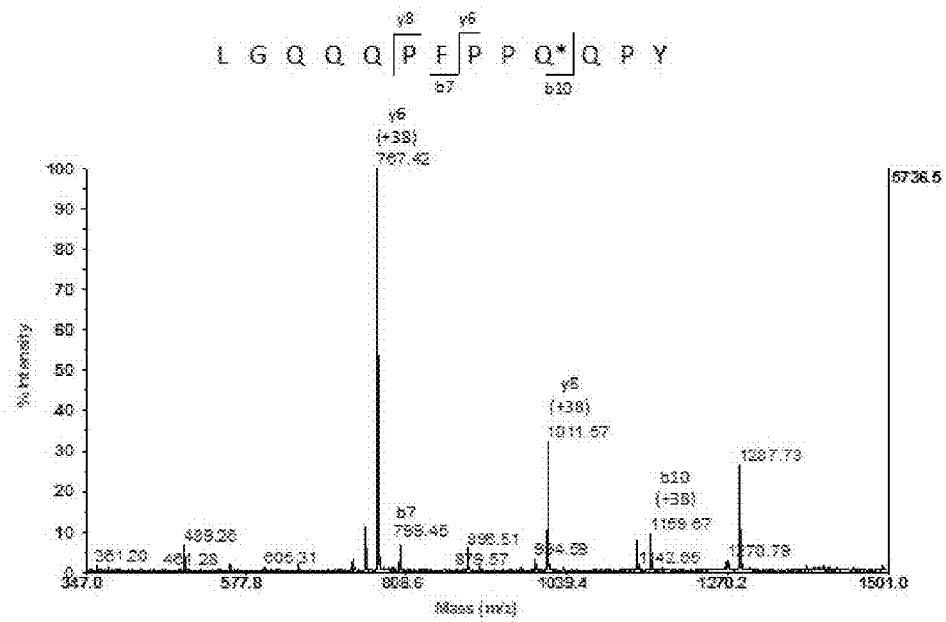
FIG. 5C shows SEQ ID NO:3 and is a MALDI-TOF/TOF MS/MS spectrum of fragment ions derived from singly charged precursor ion having m/z 1563 (photocaged glutamine product; see FIG. 5A). One glutamine residue (Q10) was modified.
Figure 5D:
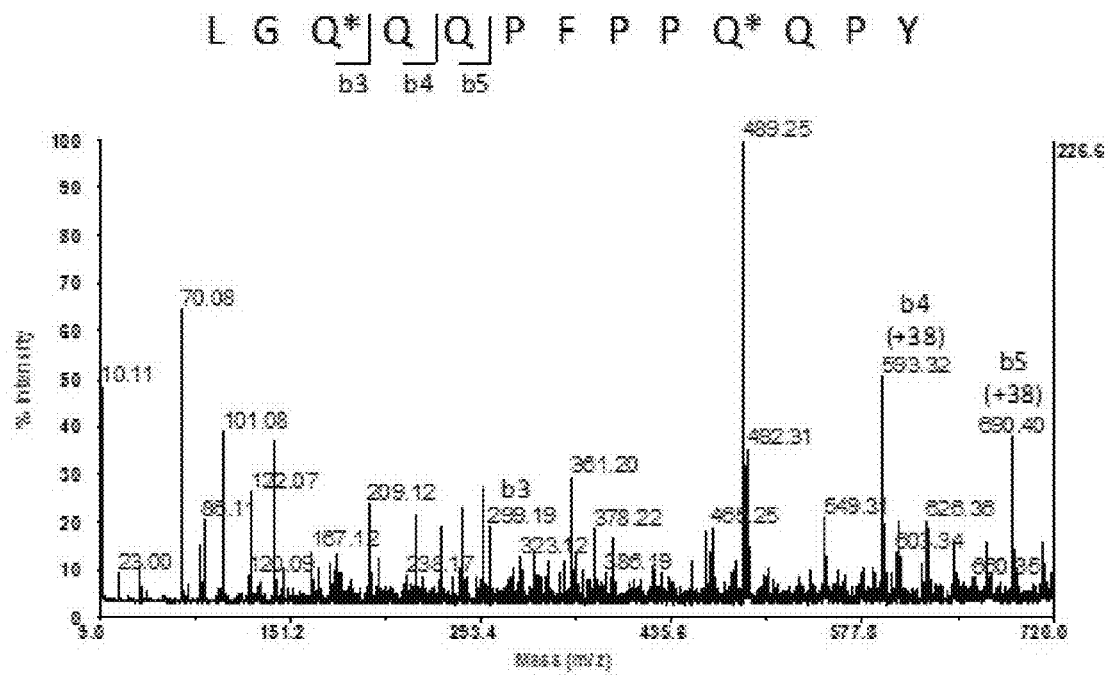
FIGS. 5D and 5E show SEQ ID NO:3 and are MALDI-TOF/TOF MS/MS spectra of fragment ions derived from singly charged precursor ion m/z 1603. Two glutamine residues (Q3/Q4 and Q10) were modified.
Figure 5E:
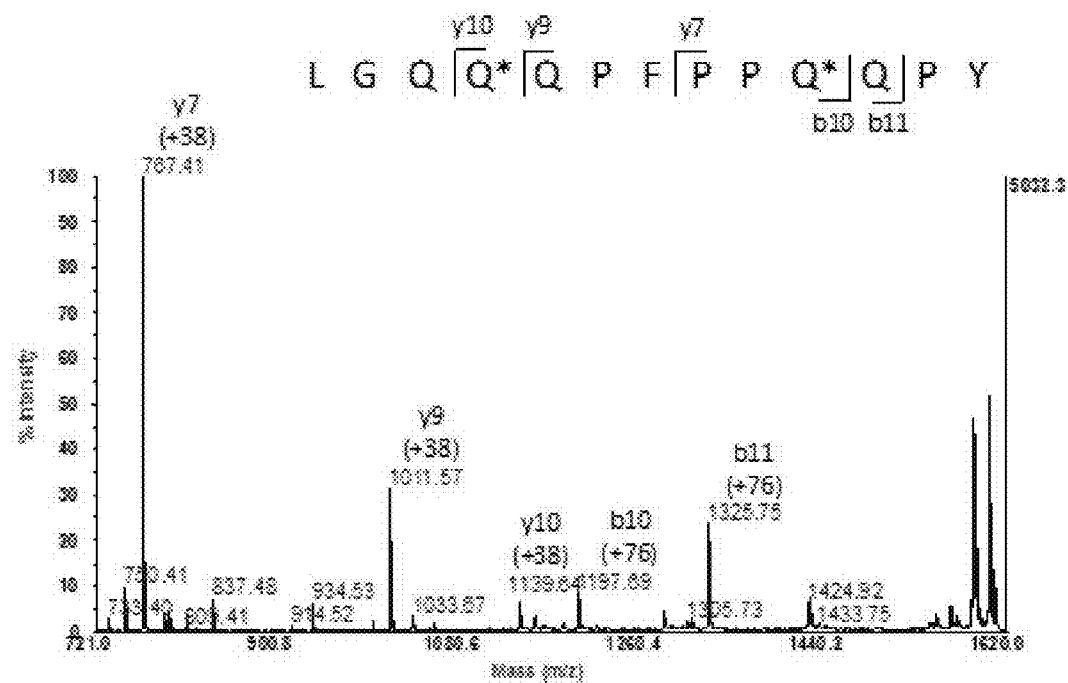

Using mass spectrometry, it was shown that propargylamine is incorporated into glutamines of the alpha gliadin peptide following transamidation reactions with microbial transglutaminase (FIG. 5A). Additionally, it was shown that the propargyl group was effectively removed by metal ions (allyl$_2$Pd$_2$Cl$_2$) to regenerate the native peptide (FIG. 5B). MALDI-TOF/TOF MS/MS spectrum of fragment ions derived from singly charged precursor ion having m/z 1563 showed that one glutamine residue (Q10) was modified (FIG. 5C). MALDI-TOF/TOF MS/MS spectrum of fragment ions derived from singly charged precursor ion having m/z 1603 (two glutamines modified) showed modification of Q3/Q4 and Q10 (5D).

Figures 8A, 8B, 8C:
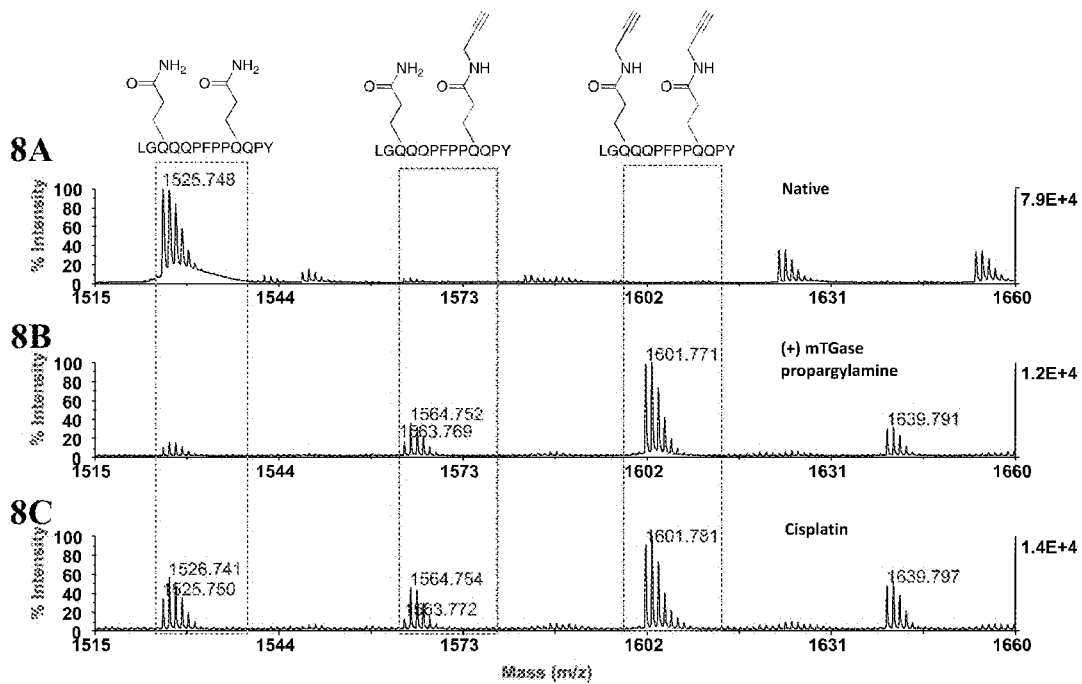
FIG. 8A is a negative mode MALDI TOF-MS spectrum of alpha gliadin peptide LGQQQPFPPQQPY (SEQ ID NO:3) (peak at m/z 1525.748).
FIG. 8B is a negative mode MALDI-TOF-MS spectrum of alpha gliadin peptide following mTGase-catalyzed transamidation reaction with propargylamine for 4 hrs at 37° C. Two major products having peaks at m/z 15634.8 and m/z 1601.8 were observed.
FIG. 8C is a negative mode MALDI-TOF-MS spectrum of modified alpha gliadin peptide (FIG. 8B) subjected to a metal-mediated cleavage reaction for regenerating the alpha-gliadin peptide. The reaction was metal-mediated and performed using cisplatin (15 hrs at 37° C.) (see peak at m/z 1526.7 for regenerated alpha-gliadin peptide).

Regeneration of the alpha gliadin peptide was also performed using cisplatin (15 hrs at 37° C.). See FIGS. 8A-8C.

Modification with 3-phenylprop-2-yn-1-amine

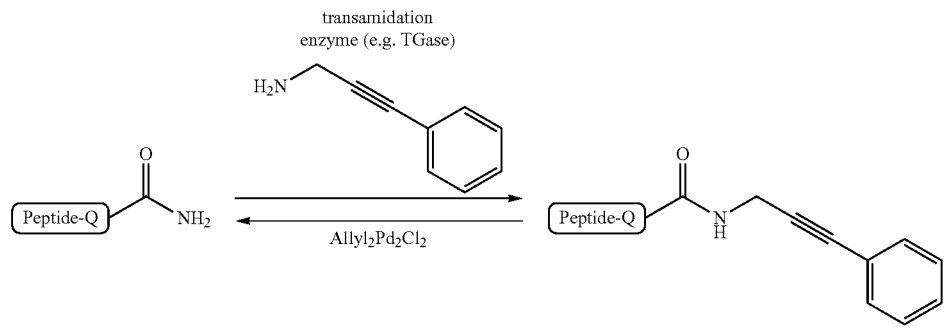

Figures 6A, 6B, 6C, 6D:
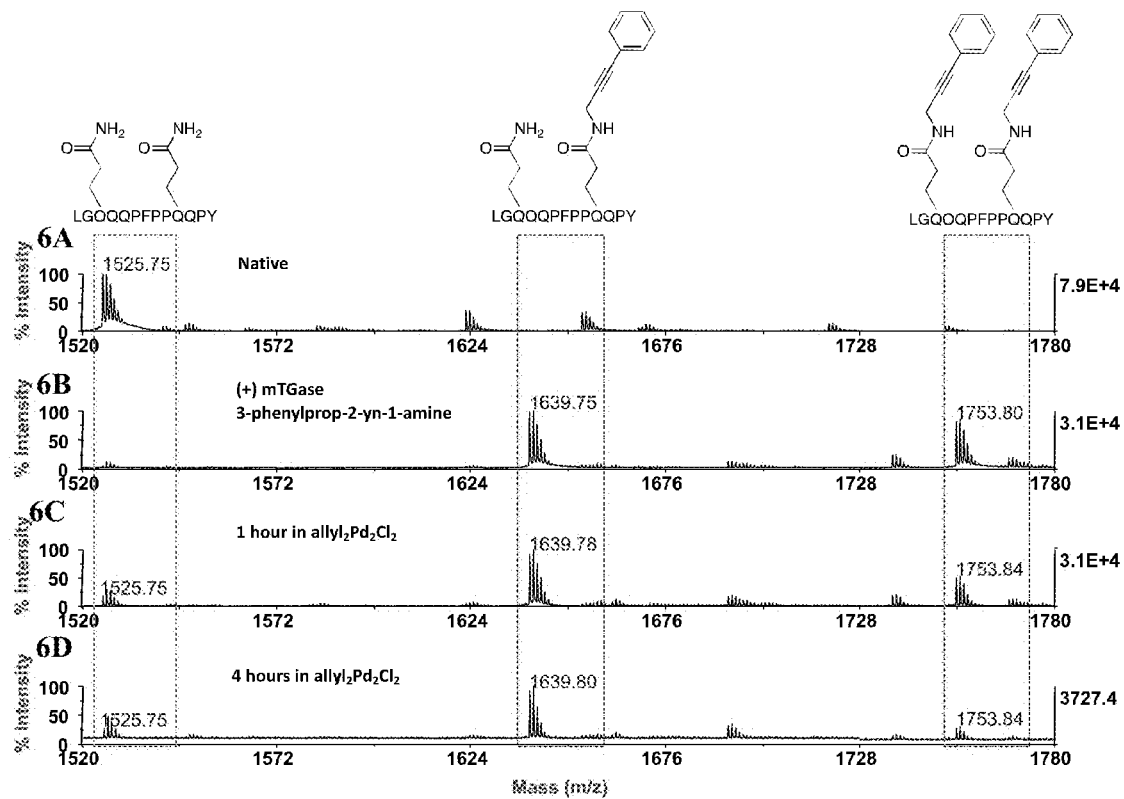
FIG. 6A is a negative mode MALDI-TOF-MS spectrum of alpha gliadin peptide LGQQQPFPPQQPY (SEQ ID NO:3) (peak at m/z 1525.75).
FIG. 6B is a negative mode MALDI-TOF-MS spectrum of alpha gliadin peptide following mTGase-catalyzed transamidation reaction with 3-phenylprop-2-yn-1-amine for 4 hrs at 37° C., pH 8. Two major modified peptide products corresponding to peaks at m/z 1639.75 and m/z 1753.80 were observed.
FIG. 6C is a negative mode MALDI-TOF-MS spectrum of modified alpha gliadin peptide (FIG. 6B) subjected to a reaction for regenerating alpha-gliadin peptide. The reaction was metal-mediated and performed using 0.1 eq. of allyl$_2$Pd$_2$Cl$_2$ for 1 hr at 37° C. (see peak at m/z 1525.75 for regenerated peptide).
FIG. 6D is a negative mode MALDI-TOF-MS spectrum of modified alpha gliadin peptide (FIG. 6B) subjected to regeneration for 4 hrs. The regenerated alpha-gliadin peptide peak is observed at m/z 1525.75.
Figure 6E:
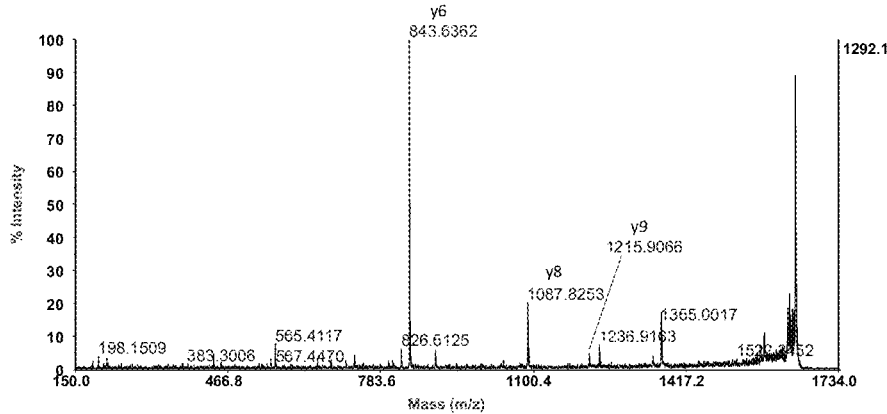
FIG. 6E shows SEQ ID NO: 3 and shows MALDI-TOF/TOF MS/MS spectrum of fragment ions derived from singly charged precursor ion having m/z 1639.75 (photocaged product.
Figure 6F:
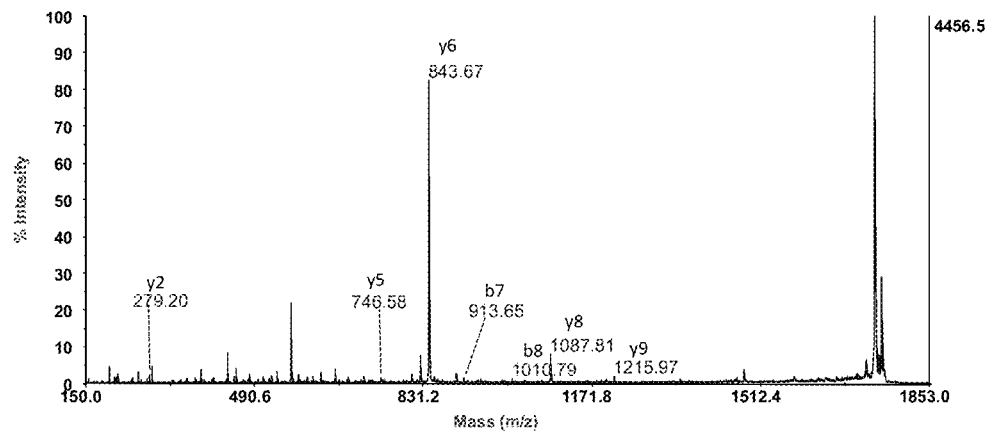
FIG. 6F shows SEQ ID NO: 3 and shows MALDI-TOF/TOF MS/MS spectrum of fragment ions derived from singly charged precursor ion having m/z 1753.80 (metal-cleavable product.

3-Phenylprop-2-yn-1-amine was incorporated into glutamine residues of alpha gliadin following transamidation as determined by mass spectrometric analysis (FIGS. 6A, 6B). Further, it was observed that the 3-phenylprop-2-yn-1-amine group was removed to a degree by treatment with allyl$_2$Pd$_2$Cl$_2$ for 1 hr., thereby regenerating the native peptide (FIG. 6C). Treatment for 4 hours. led to a higher degree of removal of the 3-phenylprop-2-yn-1 group (FIG. 6D). MALDI-TOF/TOF MS/MS spectrum of fragment ions derived from the singly charged precursor ion having m/z 1639.75 showed that one glutamine (Q10) residue was modified (FIG. 6E). MALDI-TOF/TOF MS/MS spectrum of fragment ions derived from the singly charged precursor ion having m/z 1753.79 showed two glutamine residues (Q3 and Q10) to be modified (FIG. 6F).

Figures 9A, 9B, 9C:
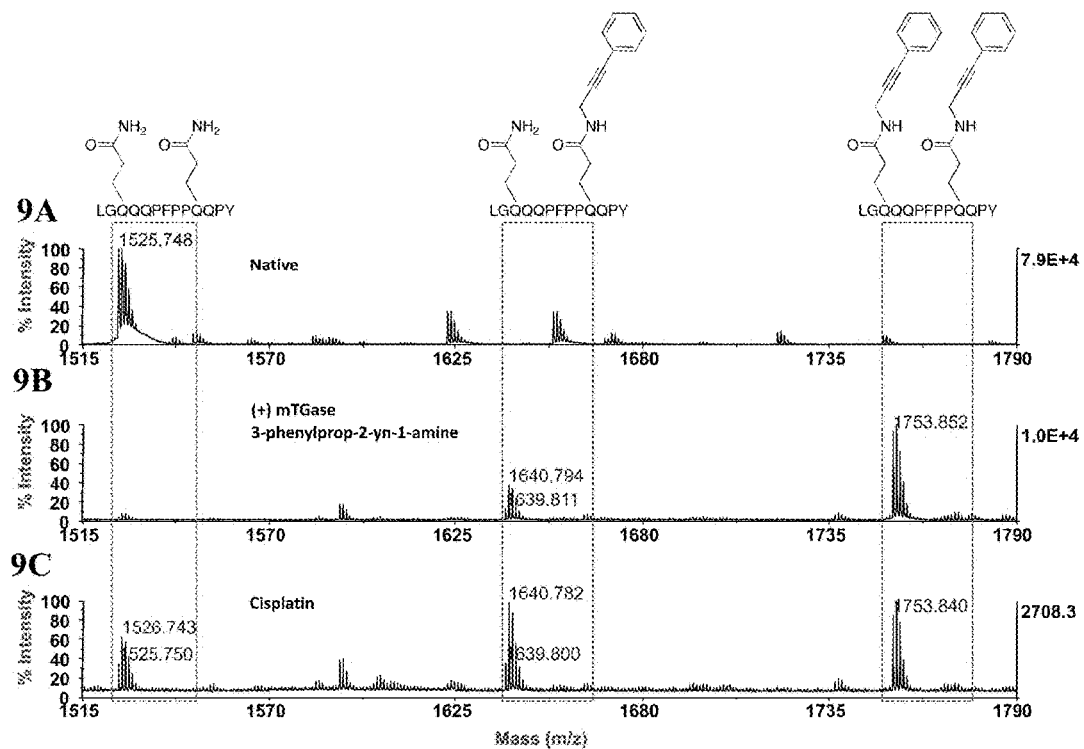
FIG. 9A is a negative mode MALDI TOF-MS spectrum of alpha gliadin peptide LGQQQPFPPQQPY (SEQ ID NO:3) (see peak at m/z 1525.748).
FIG. 9B is a negative mode MALDI-TOF-MS spectrum of alpha gliadin peptide following mTGase-catalyzed transamidation reaction with 3-phenylprop-2-yn-1-amine for 4 hrs at 37° C. Two major products having peaks at m/z 1640 and m/z 1753 were observed.
FIG. 9C shows negative mode MALDI-TOF-MS spectrum of modified alpha gliadin peptide (FIG. 8B) subjected to a metal-mediated cleavage reaction for regenerating the alpha-gliadin peptide. The reaction was metal-mediated and performed using cisplatin (15 hrs at 37° C.) (see peak at m/z 1526.7 for regenerated alpha-gliadin peptide).

Regeneration of the alpha gliadin peptide was also performed using cisplatin (15 hrs at 37° C.). See FIGS. 9A-9C.

Modification with Allylamine

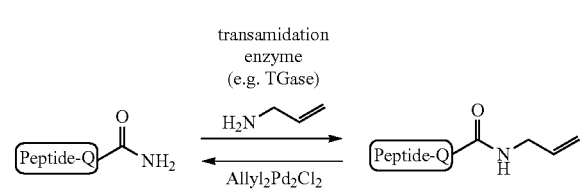

Figures 7A, 7B, 7C:
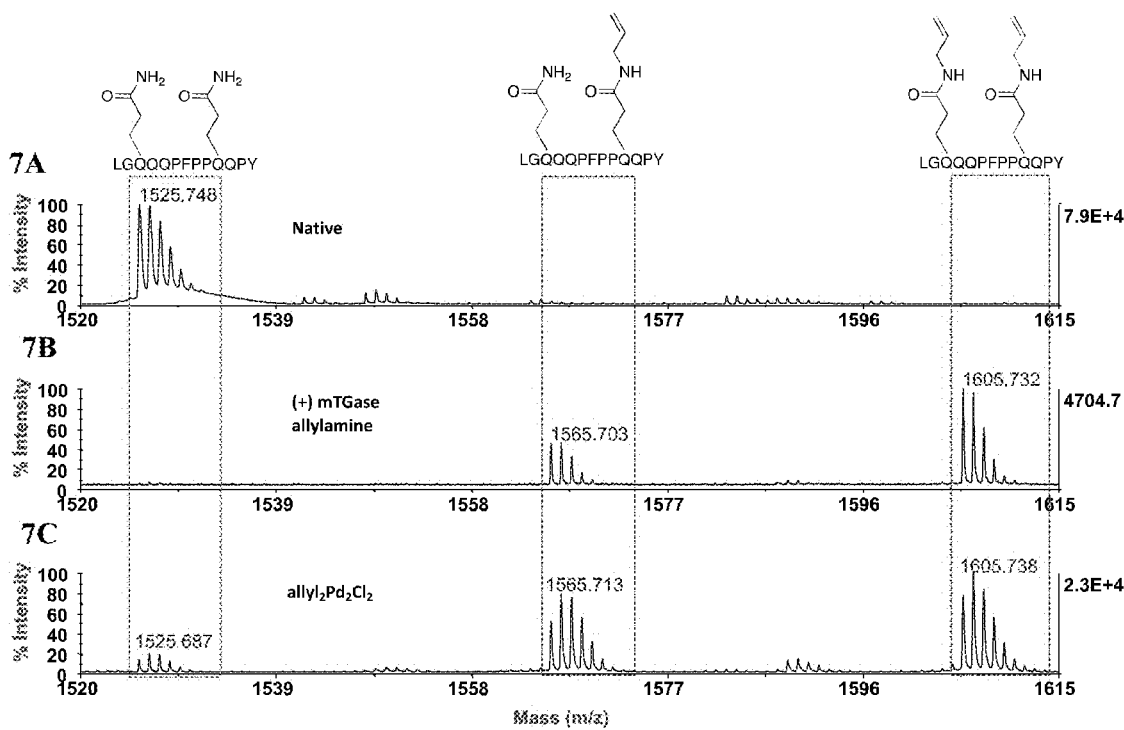
FIG. 7A is a negative mode MALDI TOF-MS spectrum of alpha gliadin peptide LGQQQPFPPQQPY (SEQ ID NO:3) (see peak at m/z 1525.75).
FIG. 7B is a negative mode MALDI-TOF-MS spectrum of alpha gliadin peptide following mTGase-catalyzed transamidation reaction with allylamine for 4 hrs at 37° C., pH 8. Two major products with peaks at m/z 1565.70 and m/z 1605.73 were observed.
FIG. 7C is a negative mode MALDI-TOF-MS spectrum of modified alpha gliadin peptide (FIG. 7B) subjected to a metal-mediated cleavage reaction for regenerating alpha-gliadin peptide. The reaction was metal-catalyzed and performed using allyl$_2$Pd$_2$Cl$_2$ for 4 hrs at 37° C. (see peak at m/z 1525.69 for regenerated alpha-gliadin peptide).

Negative mode MALDI TOF-MS spectrum of alpha gliadin peptide LGQQQPFPPQQPY (SEQ ID NO: 3) showed a peak at m/z 1525.75 (FIG. 7A). Microbial TGase-catalyzed transamidation reaction with allylamine for 4 hrs at 37° C., pH 8 led to incorporation of the allylamine group into the peptide as determined by the negative mode MALDI-TOF-MS spectrum shown in FIG. 7B. Two major products were observed at m/z 1565.70 and m/z 1605.73. Treatment with allyl$_2$Pd$_2$Cl$_2$ for 4 hrs at 37° C. led to regeneration of alpha-gliadin peptide (FIG. 7C). The reaction was metal-catalyzed and performed using allyl$_2$Pd$_2$Cl$_2$ for 4 hrs at 37° C. Alpha-gliadin peptide LGQQQPFPPQQPY (SEQ ID NO: 3) was regenerated FIG. 7C, peak at m/z 1525.69.

Example 3. Photocaging of UmuD

Figures 13A, 13B, 13C:
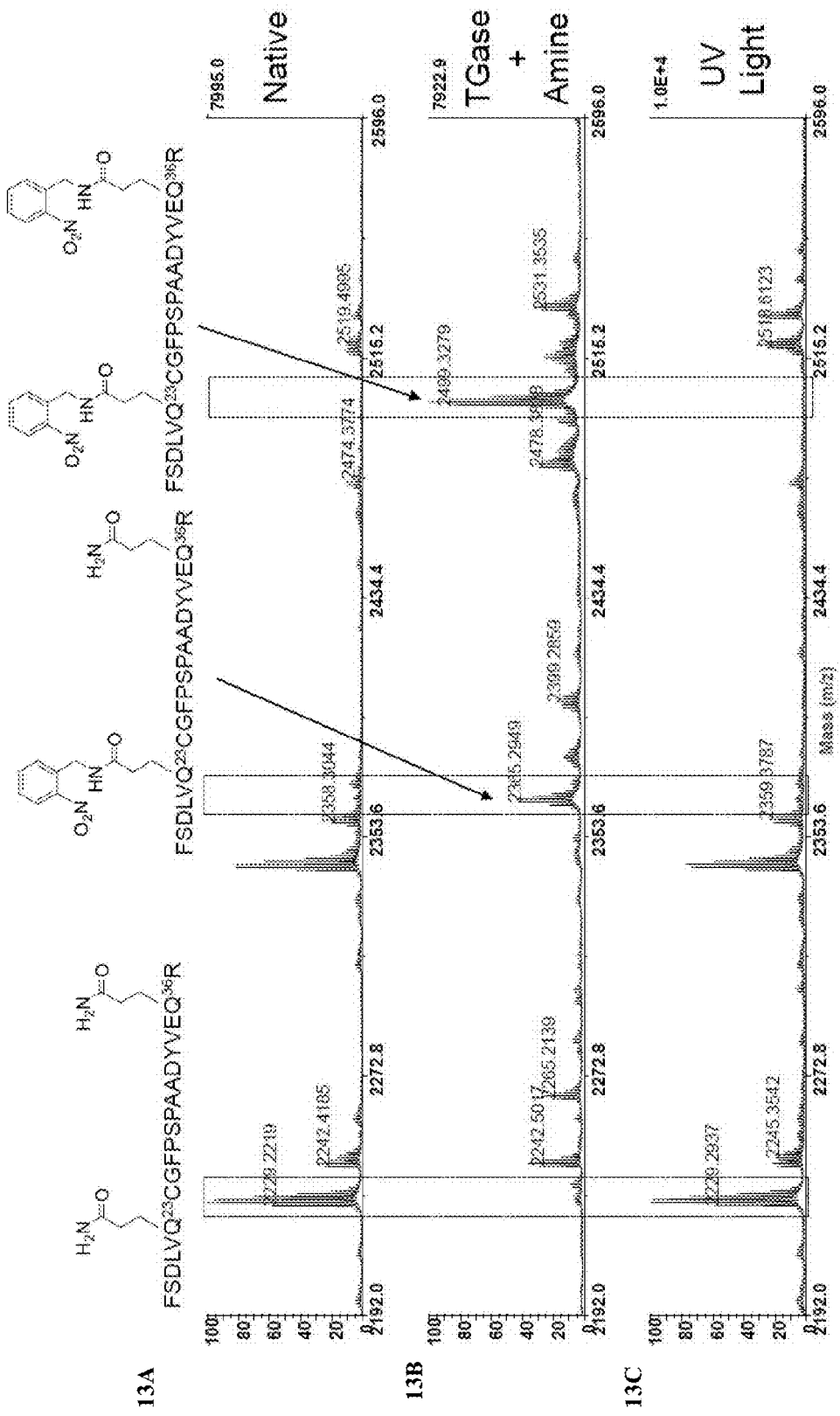
FIG. 13A is a MALDI-TOF-MS spectrum of UmuD tryptic peptide FSDLVQCGFPSPAADYVEQR (SEQ ID NO:5) (see peak at m/z 2229.22).
FIG. 13B is the spectrum of the nitrobenzyl-modified UmuD tryptic peptide (see peaks at m/z 2365.29 and m/z 2499.32).
FIG. 13C is the spectrum of the nitrobenzyl-modified UmuD tryptic peptide (see peak at m/z see peak at m/z 2229.29).

Photocaging of the protein UmuD using transglutaminase and the chromophore 2-nitrobenzylamine was examined. UmuD, together with UmuC and DNA polymerase III, is involved in the induced multigene SOS response to replication-blocking DNA lesion in *Escherichia coli*. A MALDI-TOF-MS spectrum of UmuD tryptic peptide FSDLVQCGFPSPAADYVEQR (SEQ ID NO: 5) exhibits a peak at m/z 2229.22 (FIG. 13A). Nitrobenzyl-modified UmuD tryptic peptide exhibited peaks at m/z 2365.29 and m/z 2499.32 (FIG. 13B).

Figure 13D:
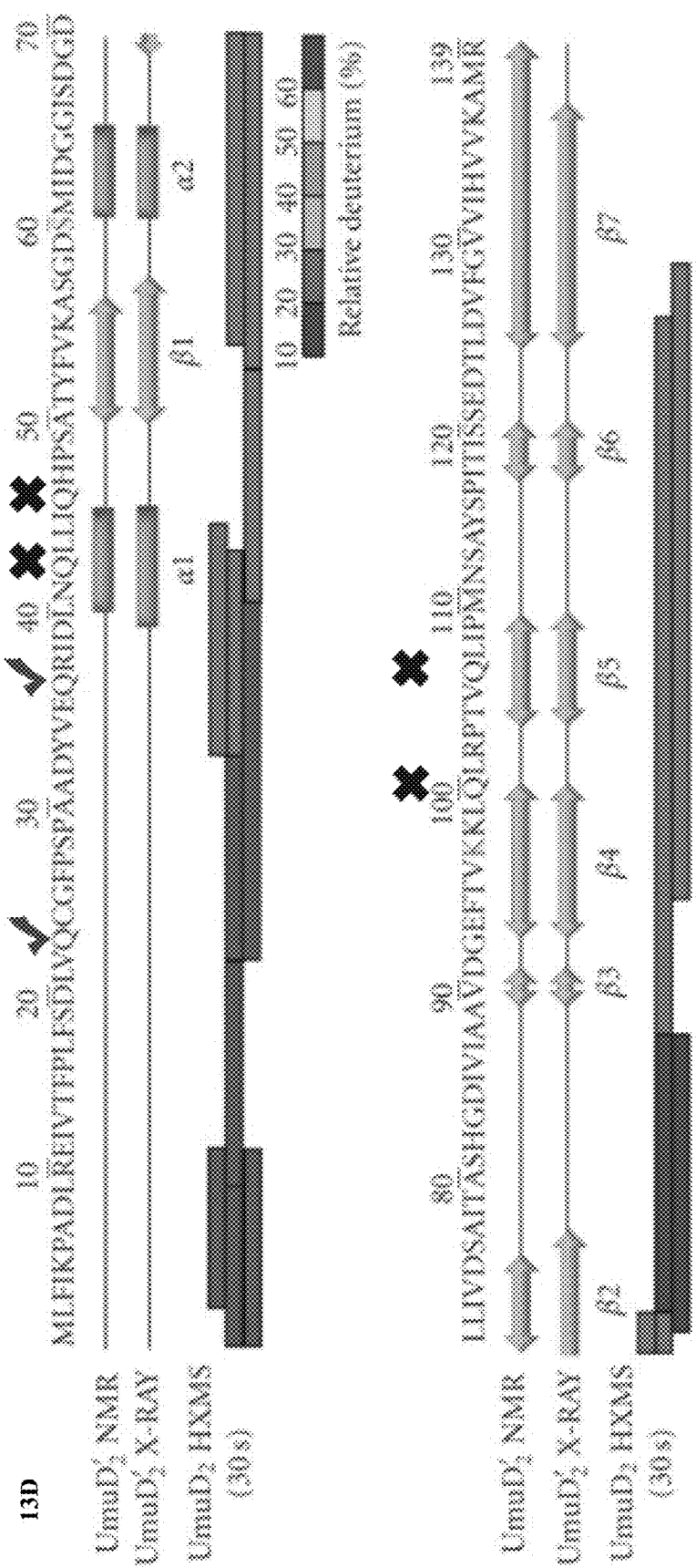
FIG. 13D shows the amino acid sequence (SEQ ID NO: 9) MLFIKPADLREIVTFPLFSDLVQCGFPSPAADYVEQ-RIDLNQLLIQHPSATYFVKASGDSMIDGGISDGDLLI-VDSAITASHGDIVIAAVDGEFTVKKLQLRPTVQLIPM-NSAYSPITI SSEDTLDVFGVVIHVVKAMR of UmuD and indicates flexibility of different regions of the protein (Ollivierre, J N et al., J Nucleic Acids, Vol. 2010, Article ID 947680). Modified and unmodified glutamine residues are indicated.
Figure 13E:
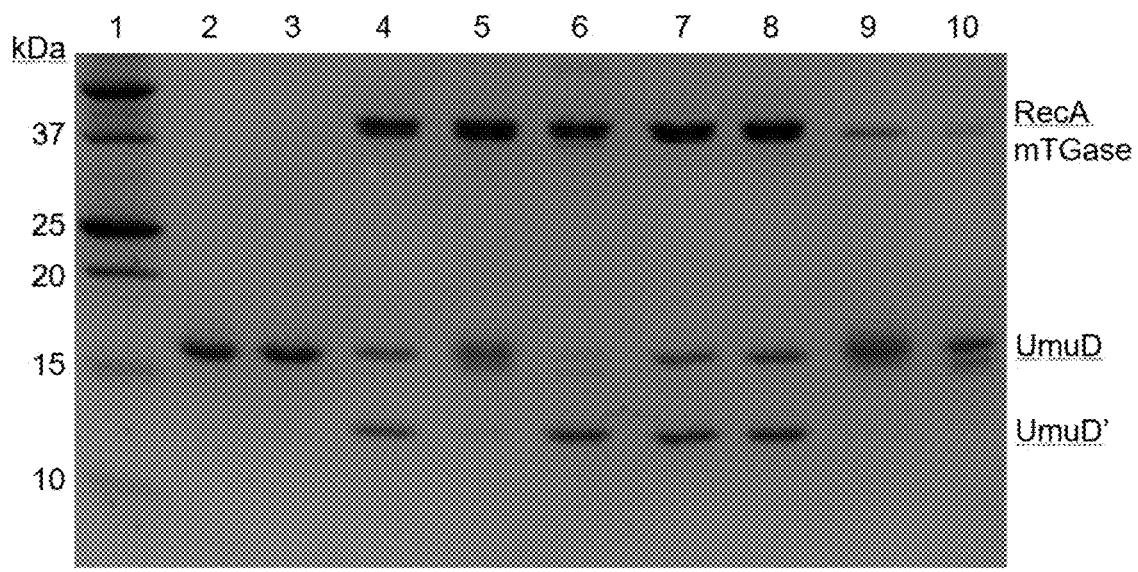
FIG. 13E shows gel electrophoresis results of self-cleavage of UmuD in caged and decaged forms. In the presence of RecA/ssDNA, the UmuD protein (~15 kDa) autocleaves to UmuD' (~12 kDa). Note that mTGase and RecA are each ~37 kDa proteins. Lane assignments of gel above are as follows: 1) MW ladder, 2) UmuD standard, 3) UmuD control, 4) UmuD standard+RecA, 5) UmuD modified+RecA, 6) UmuD modified+UV light+RecA, 7) UmuD control+RecA, 8) UmuD control+UV light+RecA, 9) UmuD modified, and 10) UmuD modified+UV light. Caging results in nearly complete inhibition of self-cleavage (lane 5) while decaging (photolysis) restores the self-cleavage activity (lane 6).

Photolysis led to regeneration of the tryptic peptide (FIG. 13C). UmuD has multiple glutamine residues, two of which are in the highly flexible N-terminal region of the protein (FIG. 13D; Olivierre et al., 2010 and Oliverre et al., 2011). Glutamine residues that are modified, Q23 and Q36, are in the flexible region of UmuD. A close view of the 3D structure of the active site of UmuD (Paetzel, M and Strynadka, N C J, Protein Science, 1999, 8:2533-2536) shows Q23 to be proximal to the cleavage site Cys24/Gly25. Consistent with the location of Q23 near the active site of UmuD, modification of the protein led to inhibition of self-cleavage as can be seen from a reduction in the level of the lower molecular weight species UmuD' (FIG. 13E). Decaging led to reversal of the inhibition (FIG. 13E).

REFERENCES

Adams, S., & Tsien, R. Controlling Cell Chemistry with Caged Compounds. *Annual Review of Physiology*, 1993, 55(1), 755-784.

Alewine, C., Hassan, R., Pastan, I., Advances in Anticancer Immunotoxin Therapy. *The Oncologist* 2015, 20, 176-185.

Alouane, A., Labruere, R., Le Saux, T., Schmidt, F., and Jullien, L., Self-Immolative Spacers: Kinetic Aspects, Structure-Property Relationships, and Applications. *Angewandte Chemie* International Edition 2015, 54, 7492-7509.

Awad, L., Jejelava, N., Burai, R., & Lashuel, H. A New Caged-Glutamine Derivative as a Tool to Control the Assembly of Glutamine-Containing Amyloidogenic Peptides. *ChemBioChem*, 2016, 17(24), 2353-2360.

Banghart, & Sabatini. Photoactivatable Neuropeptides for Spatiotemporally Precise Delivery of Opioids in Neural Tissue. *Neuron*, 2012, 73(2), 249-259.

Bao, C., Zhu, L., Lin, Q., & Tian, H. Building Biomedical Materials using Photochemical Bond Cleavage. *Advanced Materials,* 2015, 27(10), 1647-1662.

Chankeshwara, S. V.; Indrigo, E.; Bradley, M., Palladium-mediated chemistry in living cells. *Curr Opin Chem Biol* 2014, 21, 128-35.

Cho, Chung, & Shim. Engineered photo-responsive materials for near-infrared-triggered drug delivery. *Journal of Industrial and Engineering Chemistry,* 2015, 31, 15-25.

Clara B., Falk R., Alexander G., Gunter M., and Alexander H., Light-Controlled Tools. *Angewandte Chemie* International Edition 2012, 51, 8446-8476

Connel, D. R.; Rein, T.; Akermark, B.; Helquist, P., An Efficient, Palladium-Catalyzed Route to Protected Allylic Amines. *J Org Chem* 1988, 53, 3845-3849.

Csosz, E., Mesko, B., Fesus, L., Transdab wiki: the interactive transglutaminase substrate database on web 2.0 surface. *Amino Acids* 2009, 36, 615-617.

Czimadia, V. M., Koshy, K. M., Lau, K. C. M., McClelland, R. A., Nowland, V. J., and Tidwell, T. T., Acid-Catalyzed Hydrolysis of N-Vinylacetamides (Enamides). Substituent Effects of the Acetamido and Amino Groups and Linear Free Energy Correlations of Cyclohexene Reactivities. *Journal of the American Chemical Society* 1979, 101 (4), 974-979.

Dennler, P., Chiotellis, A., Fischer, E., Bregeon, D., Belmant, C., Gauthier, L., Lhospice, F., Romagne, F., Schibli, R., Transglutaminase-Based Chemo-Enzymatic Conjugation Approach Yields Homogeneous Antibody—Drug Conjugates. *Bioconjugate Chemistry,* 2014, 25, 569-578.

Dougherty, T., Gomer, C., Henderson, B., Jori, G., Kessel, D., Korbelik, M., Moan, J., Peng, Q., Photodynamic therapy. *Journal of the National Cancer Institute,* 1998, 90(12), 889-905.

Folk, J., & Cole, P. Mechanism of action of guinea pig liver transglutaminase. I. Purification and properties of the enzyme: Identification of a functional cysteine essential for activity. *The Journal of Biological Chemistry,* 1966, 241(23), 5518-5525.

Fishkin, N., Maloney, E. K., Chari, R. V. J., and Singh, R., A novel pathway for maytansinoid release from thioether linked antibody-drug conjugates (ADCs) under oxidative conditions. *Chemical Communications* 2011, 47, 10752-10754.

Fosgerau, K., and Hoffmann, T., Peptide therapeutics: current status and future directions. Drug Discovery Today 2015, 20 (1), 122-128.

Fricker, L. D., Neuropeptides and Other Bioactive Peptides: From Discovery to Function. 2012. Colloquium series on Neuropeptides.

Furuta, T., Wang, S., Dantzker, J., Dore, T., Bybee, W., Callaway, E., Denk, W., Tsien, R. Brominated 7-hydroxycoumarin-4-ylmethyls: Photolabile protecting groups with biologically useful cross-sections for two photon photolysis. *Proceedings of the National Academy of Sciences of the United States of America,* 1999, 96(4), 1193-1200.

Gao, X., Pellois, J., Na, P., Kim, Y., Gulari, Y., & Zhou, E. High density peptide microarrays. In situ synthesis and applications. *Molecular Diversity,* 2004, 8(3), 177-187.

Givens, R., Conrad, Peter G., I., Yousef, A., & Lee, J. *Photoremovable Protecting Groups.* CRC Handbook of Organic Photochemistry and Photobiology, 2, 2004.

Gnaccarini, C., Ben-tahar, W., Mulani, A., Roy, I., Lubell, W., Pelletier, J., & Keillor, J. Site-specific protein propargylation using tissue transglutaminase. *Organic & Biomolecular Chemistry,* 2012, 10(27), 5258-5265.

Graham C. R. Ellis-Davies. Caged compounds: Photorelease technology for control of cellular chemistry and physiology. *Nature Methods,* 2007, 4(8), 619-628.

Gundersen, M., Keillor, T., & Pelletier, J. Microbial transglutaminase displays broad acyl-acceptor substrate specificity. *Applied Microbiology and Biotechnology,* 2014, 98(1), 219-230.

Hansch, C., Leo, A., and Taft, R. W., A Survey of Hammett Substituent Constants and Resonance and Field Parameters. *Chemical Reviews* 1991, 91, 165-195.

Hiraoka, & Hamachi. Caged RNase: Photoactivation of the enzyme from perfect off-state by site-specific incorporation of 2-nitrobenzyl moiety. *Bioorganic & Medicinal Chemistry Letters,* 2003, 13(1), 13-15.

Johnstone, T. C.; Suntharalingam, K.; Lippard, S. J., The Next Generation of Platinum Drugs: Targeted Pt(II) Agents, Nanoparticle Delivery, and Pt(IV) Prodrugs. *Chem Rev* 2016, 116 (5), 3436-86.

Klan, P., Solomek, T., Bochet, C., Blanc, A., Givens, R., Rubina, M., Popik, V., Kostikov, A., Wirz, J., Photoremovable Protecting Groups in Chemistry and Biology: Reaction Mechanisms and Efficacy. *Chemical Reviews,* 2013, 113(1), 119-191.

Kotzur, N., Briand, B., Beyermann, M., & Hagen, V. Wavelength-selective photoactivatable protecting groups for thiols. *Journal of the American Chemical Society,* 2009, 131(46), 16927-16931.

Li, J.; Chen, P. R., Development and application of bond cleavage reactions in bioorthogonal chemistry. *Nat Chem Biol* 2016, 12 (3), 129-37.

Li, J.; Yu, J.; Zhao, J.; Wang, J.; Zheng, S.; Lin, S.; Chen, L.; Yang, M.; Jia, S.; Zhang, X.; Chen, P. R., Palladium-triggered deprotection chemistry for protein activation in living cells. *Nat Chem* 2014, 6 (4), 352-61

Liu, B.; Wang, H.; Wang, T.; Bao, Y.; Du, F.; Tian, J.; Li, Q.; Bai, R., A new ratiometric ESIPT sensor for detection of palladium species in aqueous solution. *Chem Commun (Camb)* 2012, 48 (23), 2867-9.

Malesevic, M., Migge, A., Hertel, T. C., Pietzsch, M., A fluorescence-based array screen for transglutaminase substrates. *ChemBioChem* 2015, 16 (8), 1169-1174.

Marriott, G., Ottl, J., Heidecker, M., & Gabriel, D. Light-directed activation of protein activity from caged protein conjugates. *Methods in Enzymology,* 1998, 291, 95-116.

Marriott, G. Caged protein conjugates and light-directed generation of protein activity: Preparation, photoactivation, and spectroscopic characterization of caged G-actin conjugates. *Biochemistry,* 1994, 33(31), 9092-9097.

Mazora, R., Kinga, M. K., Ondaa, M., Cuburub, N., Addissiea, S., Crownc, D., Liva, X., Kishimotod, T. K., Pastana, I., Tolerogenic nanoparticles restore the antitumor activity of recombinant immunotoxins by mitigating immunogenicity. *Proceedings of the National Academy of Sciences of the United States of America,* 2018, E733-E742.

McGrath, N. A., Brichacek, M., and Njardson, J. T., A Graphical Journey of Innovative Organic Architectures That Have Improved Our Lives. *Journal of Chemical Education* 2010, 87 (12), 1348-1349.

Miesenbck, G. Optogenetic Control of Cells and Circuits. *Annual Review of Cell and Developmental Biology,* 2011, 27, 731-758.

Mullard, A., 2017 FDA drug approvals. *Nature Reviews Drug Discovery* 2018, 17, 81-85.

Obrecht, J., Hellberg, L., and Somanathan, R., Synthesis of Some Naturally-occurring Styrylamides. *Journal of the Chemical Society, Chemical Communications* 1987, (16), 1219-1220.

Ohtsuka, T., Ota, M., Nio, N., & Motoki, M. Comparison of Substrate Specificities of Transglutaminases Using Synthetic Peptides as Acyl donors. *Bioscience, Biotechnology, and Biochemistry,* 2000, 64(12), 2608-2613.

Olejniczak, Carling, & Almutairi. Photocontrolled release using one-photon absorption of visible or NIR light. *Journal of Controlled Release,* 2015, 219, 18-30.

Ollivierre J N, Fang J, Beuning P J. The Roles of UmuD in Regulating Mutagenesis. *J Nucleic Acids.* 2010 Sep. 30; 2010, Article ID 947680, 12 pages Ollivierre, J N, Sikora, J L and Beuning P J. The Dimeric SOS Mutagenesis Protein UmuD Is Active as a Monomer. *J Biol Chem.* 2011 Feb. 4; 286(5): 3607-3617.

Pastan, I., Hassan, R., Fitzgerald, D. J., Kreitman, R. J., Immunotoxin therapy of cancer. *Nature Reviews Cancer.* 2006, 6 (7), 559-565.

Perboni, S., Vignoni, M., Inui, A., NPY: *Handbook of Biologically Active Peptides: Ingestive Peptides,* 2013, Ch. 154.

Piant, S., Bolze, F., & Specht, A. Two-photon uncaging, from neuroscience to materials. *Optical Materials Express,* 2016, 6(5), 1679-1691.

Rambabu, D., S. Bhavani, S., Swamy, N. K., Rao, M. V. B., Pal, M., Pd/C-mediated depropargylation of propargyl ethers/amines in water. *Tetrahedron Letters* 2013, 54, 1169-1173.

Ramesh, Doraiswamy, Wieboldt, Raymond, Billington, Andrew P., Carpenter, Barry K., & Hess, George P. Photolabile precursors of biological amides: Synthesis and characterization of caged o-nitrobenzyl derivatives of glutamine, asparagine, glycinamide, and gamma-aminobutyramide. *Journal of Organic Chemistry,* 1993, 58(17), 4599-4605.

Read, J., Pirrung, M., Stryer, L., Lu, A., & Solas, D. Light-Directed, Spatially Addressable Parallel Chemical Synthesis. *Science,* 1991, 251(4995), 767-773.

Strop, P. Versatility of Microbial Transglutaminase. *Bioconjugate Chemistry,* 2014, 25(5), 855-862.

Sugimura, Yokoyama, Nio, Maki, & Hitomi. Identification of preferred substrate sequences of microbial transglutaminase from *Streptomyces mobaraensis* using a phage-displayed peptide library. *Archives of Biochemistry and Biophysics,* 2008, 477(2), 379-383.

Tatsu, Shigeri, Sogabe, Yumoto, & Yoshikawa. Solid-Phase Synthesis of Caged Peptides Using Tyrosine Modified with a Photocleavable Protecting Group: Application to the Synthesis of Caged Neuropeptide Y. *Biochemical and Biophysical Research Communications,* 1996, 227(3), 688-693.

Tatsu, Y., Nishigaki, T., Darszon A., and Yumoto, N. A caged sperm-activating peptide that has a photocleavable protecting group on the backbone amide. Febs Letters, 2002, 525 (1-3), 20-24.

Volker, T., Meggers, E., Transition-metal-mediated uncaging in living human cells—an emerging alternative to photolabile protecting groups. *Current Opinion Chemical Biology* 2015, 25, 48-54.

Walsh, G., Biopharmaceutical benchmarks 2014. Nature Biotechnology 2014, 32 (10), 992-1000.

Weinrich, D., Lin, P., Jonkheijm, P., Nguyen, U., Schröder, H., Niemeyer, C., Alexandrov, K., Goody, R., Waldmann, H., Oriented Immobilization of Farnesylated Proteins by the Thiol-Ene Reaction. *Angewandte Chemie International Edition,* 2010, 49(7), 1252-1257.

Walsh, G., Biopharmaceutical benchmarks 2014. Nature Biotechnology 2014, 32 (10), 992-1000.

Wang, J., Zheng, S., Liu, Y., Zhang, Z., Lin, Z., Li, J., Zhang, G., Wang, X., Li, J., Chen, P. R., Palladium-Triggered Chemical Rescue of Intracellular Proteins via Genetically Encoded Allene-Caged Tyrosine. *Journal of the American Chemical Society* 2016, 138 (46), 15118-15121.

Wang, Z., Zheng, Q., Zhang, H., Bronson, R. T., Madsen, J. C., Sachs, D. H., Huang, C. A., Wang, Z., Ontak-like human IL-2 fusion toxin. *Journal of Immunological Methods* 2017, 448, 51-58.

Zhao, X., Shaw, A. C., Wang, J., Chang, C., Deng, J., Su, J., A Novel High-Throughput Screening Method for Microbial Transglutaminases with High Specificity toward Gln141 of Human Growth Hormone. *Journal of Biomolecular Screening* 2010, 15, 206-212

Zhou, Z. S., Jiang, N., and Hilvert, D., An Antibody-Catalyzed Selenoxide Elimination. *Journal of the American Chemical Society* 1997, 119, 3623-3624.

As used herein, "consisting essentially of" allows the inclusion of materials or steps that do not materially affect the basic and novel characteristics of the claim. Any recitation herein of the term "comprising", particularly in a description of components of a composition or in a description of elements of a device, can be exchanged with "consisting essentially of" or "consisting of".

The content of the ASCII text file of the sequence listing named Substitute-Sequence-Listing-19815-0477_ST25, having a size of 3.02 kilobytes and a creation date of 24 May 2021, and electronically submitted via EFS-Web, is incorporated herein by reference in its entirety.

What is claimed is:

1. A method for modifying a protein or peptide having one or more glutamine residues, the method comprising:
performing a transglutaminase-catalyzed reaction between the protein or peptide and an amine-containing reagent, thereby producing a first derivative of the protein or peptide, wherein the reagent becomes covalently linked through its amine function to a side chain of at least one of said one or more glutamine residues; wherein the original protein or peptide, or a second derivative thereof, can be obtained by a treatment of the first derivative of the protein or peptide;
wherein the treatment comprises a photolysis reaction; and
wherein the amine-containing reagent is a compound having the formula

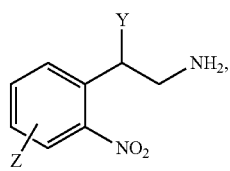

wherein
Y is selected from the group consisting of hydrogen, halogen, hydroxy, thiol, cyano, isocyano, thiocyano, isothiocyano, $(C_1-C_3)$alkyl, halo$(C_1-C_3)$alkyl, $(C_1-C_3)$alkyloxy; halo$(C_1-C_3)$alkyloxy, and cyclopropyl; and
Z is selected from the group consisting of hydrogen; halogen; hydroxy; nitro; cyano; isocyano; thiocyano; isothiocyano; $(C_1-C_6)$alkyl; halo$(C_1-C_6)$alkyl; phenyl $(C_1-C_6)$alkyl; phenyl optionally substituted with halogen, $(C_1-C_3)$alkyl, halo$(C_1-C_3)$alkyl or $(C_1-C_3)$alkyloxy; $(C_1-C_3)$alkyloxy; cyclopropyl; halo$(C_1-C_3)$alkyloxy; $(C_2-C_4)$alkenyl; $(C_2-C_4)$alkynyl; $(C_1-C_6)$alkylthio; $C(O)OR^1$; $COR^1$; $CON(R^1)_2$; azide; sulfinyl; sulfonyl; sulfonyl halide; sulfino; sulfo; thiol; $(C_4-C_6)$diene; and aryl or aryloxy optionally substituted halogen or $(C_1-C_3)$alkyl; wherein $R^1$ is hydrogen, halogen, $(C_1-C_3)$alkyl, halo$(C_1-C_3)$alkyl, or aryl optionally substituted with halogen or $(C_1-C_3)$alkyl.

2. The method of claim 1, further comprising carrying out said treatment of the first derivative.

3. A method for modifying a protein or peptide having one or more glutamine residues, the method comprising:
performing a transglutaminase-catalyzed reaction between the protein or peptide and an amine-containing reagent, thereby producing a first derivative of the protein or peptide, wherein the reagent becomes covalently linked through its amine function to a side chain of at least one of said one or more glutamine residues; wherein the original protein or peptide, or a second derivative thereof, can be obtained by a treatment of the first derivative of the protein or peptide;
wherein the treatment comprises a photolysis reaction;
wherein the amine-containing reagent comprises a hydroxylamine group, and the reagent is linked through the hydroxylamine group to the side chain of the at least one glutamine residue;
wherein the reagent comprising a hydroxylamine group is a compound having the formula

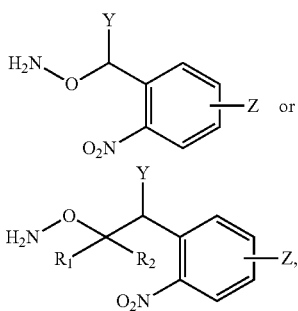

wherein

Y is selected from the group consisting of hydrogen, halogen, hydroxy, thiol, cyano, isocyano, thiocyano, isothiocyano, $(C_1$-$C_3)$alkyl, halo$(C_1$-$C_3)$alkyl, $(C_1$-$C_3)$alkyloxy; halo$(C_1$-$C_3)$alkyloxy, and cyclopropyl; and Z is selected from the group consisting of hydrogen; halogen; hydroxy; nitro; cyano; isocyano; thiocyano; isothiocyano; $(C_1$-$C_6)$alkyl; halo$(C_1$-$C_6)$alkyl; phenyl$(C_1$-$C_6)$alkyl; phenyl optionally substituted with halogen, $(C_1$-$C_3)$alkyl, halo$(C_1$-$C_3)$alkyl or $(C_1$-$C_3)$alkyloxy; $(C_1$-$C_3)$alkyloxy; cyclopropyl; halo$(C_1$-$C_3)$alkyloxy; $(C_2$-$C_4)$alkenyl; $(C_2$-$C_4)$alkynyl; $(C_1$-$C_6)$alkylthio; C(O)OR$^1$; COR$^1$; CON(R$^1$)$_2$; azide; sulfinyl; sulfonyl; sulfonyl halide; sulfino; sulfo; thiol; $(C_4$-$C_6)$diene; and aryl or aryloxy optionally substituted halogen or $(C_1$-$C_3)$alkyl; wherein R$^1$ is hydrogen, halogen, $(C_1$-$C_3)$alkyl, halo$(C_1$-$C_3)$alkyl, or aryl optionally substituted with halogen or $(C_1$-$C_3)$alkyl.

4. A method for modifying a protein or peptide having one or more glutamine residues, the method comprising:

performing a transglutaminase-catalyzed reaction between the protein or peptide and an amine-containing reagent, thereby producing a first derivative of the protein or peptide, wherein the reagent becomes covalently linked through its amine function to a side chain of at least one of said one or more glutamine residues; wherein the original protein or peptide, or a second derivative thereof, can be obtained by a treatment of the first derivative of the protein or peptide;

wherein the treatment comprises a photolysis reaction;

wherein the amine-containing reagent comprises a hydrazine group, and the reagent is linked through the hydrazine group to the side chain of the at least one glutamine residue;

wherein the reagent comprising a hydrazine group is a compound having the formula

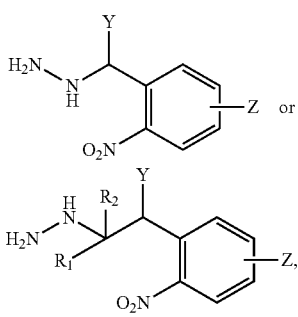

wherein

Y, R$_1$ and R$_2$ are selected from the group consisting of hydrogen, halogen, hydroxy, thiol, cyano, isocyano, thiocyano, isothiocyano, $(C_1$-$C_3)$alkyl, halo$(C_1$-$C_3)$alkyl, $(C_1$-$C_3)$alkyloxy; halo$(C_1$-$C_3)$alkyloxy, and cyclopropyl; and Z is selected from the group consisting of hydrogen; halogen; hydroxy; nitro; cyano; isocyano; thiocyano; isothiocyano; $(C_1$-$C_6)$alkyl; halo$(C_1$-$C_6)$alkyl; phenyl$(C_1$-$C_6)$alkyl; phenyl optionally substituted with halogen, $(C_1$-$C_3)$alkyl, halo$(C_1$-$C_3)$alkyl or $(C_1$-$C_3)$alkyloxy; $(C_1$-$C_3)$alkyloxy; cyclopropyl; halo$(C_1$-$C_3)$alkyloxy; $(C_2$-$C_4)$alkenyl; $(C_2$-$C_4)$alkynyl; $(C_1$-$C_6)$alkylthio; C(O)OR$^1$; COR$^1$; CON(R$^1$)$_2$; azide; sulfinyl; sulfonyl; sulfonyl halide; sulfino; sulfo; thiol; $(C_4$-$C_6)$diene; and aryl or aryloxy optionally substituted halogen or $(C_1$-$C_3)$alkyl; wherein R$^1$ is hydrogen, halogen, $(C_1$-$C_3)$alkyl, halo$(C_1$-$C_3)$alkyl, or aryl optionally substituted with halogen or $(C_1$-$C_3)$alkyl.

5. A method for modifying a protein or peptide having one or more glutamine residues, the method comprising:

performing a transglutaminase-catalyzed reaction between the protein or peptide and an amine-containing reagent, thereby producing a first derivative of the protein or peptide, wherein the reagent becomes covalently linked through its amine function to a side chain of at least one of said one or more glutamine residues; wherein the original protein or peptide, or a second derivative thereof, can be obtained by a treatment of the first derivative of the protein or peptide;

wherein the treatment comprises a reaction catalyzed by a metal in elemental form, a metal in ionic form, or a metal that is part of a complex;

wherein the amine-containing reagent is a reagent comprising a hydroxylamine group, wherein the reagent is linked through the hydroxylamine group to a side chain of the at least one glutamine residue; or a reagent comprising a hydrazine group, wherein the reagent is linked through the hydrazine group to a side chain of the at least one glutamine residue.

6. The method of claim 5, wherein the reagent comprising a hydroxylamine group is a compound having the formula

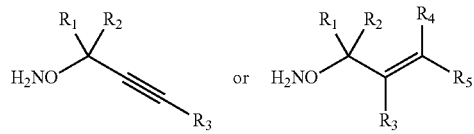

wherein R$_1$, R$_2$, R$_3$, R$_4$, and R$_5$ are independently selected from the group consisting of: selected from the group consisting of: hydrogen; halogen; hydroxy; nitro; cyano; isocyano; thiocyano; isothiocyano; $(C_1$-$C_6)$alkyl; halo$(C_1$-$C_6)$alkyl; phenyl$(C_1$-$C_6)$alkyl; phenyl optionally substituted with halogen, $(C_1$-$C_3)$alkyl, halo$(C_1$-$C_3)$alkyl or $(C_1$-$C_3)$alkyloxy; $(C_1$-$C_3)$alkyloxy; cyclopropyl; halo$(C_1$-$C_3)$alkyloxy; $(C_2$-$C_4)$alkenyl; $(C_2$-$C_4)$alkynyl; $(C_1$-$C_6)$alkylthio; C(O)OR$^1$; COR$^1$; CON(R$^1$)$_2$; azide; sulfinyl; sulfonyl; sulfonyl halide; sulfino; sulfo; thiol; $(C_4$-$C_6)$diene; and aryl or aryloxy optionally substituted halogen or $(C_1$-$C_3)$alkyl; wherein R$^1$ is hydrogen, halogen, $(C_1$-$C_3)$alkyl, halo$(C_1$-$C_3)$alkyl, or aryl optionally substituted with halogen or $(C_1$-$C_3)$alkyl.

7. The method of claim 5, wherein the reagent comprising a hydrazine group is a compound having the formula

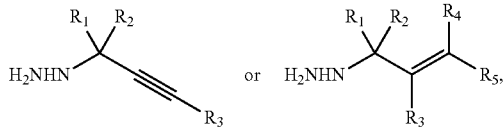

wherein $R_1$, $R_2$, $R_3$, $R_4$, and $R_5$ are independently selected from the group consisting of: selected from the group consisting of hydrogen; halogen; hydroxy; nitro; cyano; isocyano; thiocyano; isothiocyano; ($C_1$-$C_6$)alkyl; halo($C_1$-$C_6$)alkyl; phenyl($C_1$-$C_6$)alkyl; phenyl optionally substituted with halogen, ($C_1$-$C_3$)alkyl, halo($C_1$-$C_3$)alkyl or ($C_1$-$C_3$)alkyloxy; ($C_1$-$C_3$)alkyloxy; cyclopropyl; halo($C_1$-$C_3$)alkyloxy; ($C_2$-$C_4$)alkenyl; ($C_2$-$C_4$)alkynyl; ($C_1$-$C_6$) alkylthio; $C(O)OR^1$; $COR^1$; $CON(R^1)_2$; azide; sulfinyl; sulfonyl; sulfonyl halide; sulfino; sulfo; thiol; ($C_4$-$C_6$) diene; and aryl or aryloxy optionally substituted halogen or ($C_1$-$C_3$)alkyl; wherein is hydrogen, halogen, ($C_1$-$C_3$)alkyl, halo($C_1$-$C_3$)alkyl, or aryl optionally substituted with halogen or ($C_1$-$C_3$)alkyl.

8. The method of claim 5, wherein the metal is palladium, iron, ruthenium, or platinum.

9. A method for modifying a protein or peptide having one or more glutamine residues, the method comprising:
performing a transglutaminase-catalyzed reaction between the protein or peptide and an amine-containing reagent, thereby producing a first derivative of the protein or peptide, wherein the reagent becomes covalently linked through its amine function to a side chain of at least one of said one or more glutamine residues; wherein the original protein or peptide, or a second derivative thereof, can be obtained by a treatment of the first derivative of the protein or peptide;
wherein the treatment comprises exposure to a physiological condition, altered pH, altered ionic strength, or elevated temperature;
wherein the amine-containing reagent is

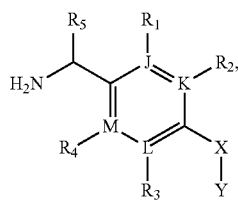

(I)

wherein

X is oxygen, sulfur, nitrogen, phosphorous, or selenium;
Y is hydrogen, alkyl, acyl, sulfo, or phospho;
J, K, L, and M are each independently carbon or nitrogen;
$R_1$, $R_2$, $R_3$, and $R_4$ are each independently hydrogen, halogen, hydroxyl, nitro, cyano, isocyano, thiocyano, isothiocyano, aryl, alkyl, alkenyl, alkynyl, alkoxy, alkylthio, amino, monoalkylamino, dialkylamino, acyl, carbonyl, carboxyl, azide, sulfinyl, sulfonyl, sulfino, sulfo, or thiol; and
$R_5$ is hydrogen, cyano, isocyano, aryl, alkyl, alkenyl, alkynyl, acyl, carbonyl, or carboxyl.

10. A method for modifying a protein or peptide having one or more glutamine residues, the method comprising:
performing a transglutaminase-catalyzed reaction between the protein or peptide and an amine-containing reagent, thereby producing a first derivative of the protein or peptide, wherein the reagent becomes covalently linked through its amine function to a side chain of at least one of said one or more glutamine residues; wherein the original protein or peptide, or a second derivative thereof, can be obtained by a treatment of the first derivative of the protein or peptide;
wherein the treatment comprises exposure to a physiological condition, altered pH, altered ionic strength, or elevated temperature;
wherein the amine-containing reagent is

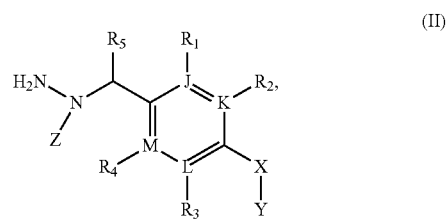

(II)

wherein:

Z is alkyl, aryl, acyl, acyloxy, alkenyl, alkynyl, silyl, sulfo, sulfonyl, sulfinyl, phospho, phosphonyl, acyl, cyano, alkoxy, or nitroso;

X is oxygen, sulfur, nitrogen, phosphorous, or selenium;

Y is hydrogen, alkyl, dialkyl, acyl, sulfo, sulfonyl, sulfinyl, phospho, phosphonyl, hydroxyl, silyl, nitrosyl, thiol, sulfide, or oxo;

J, K, L, and M are each independently carbon or nitrogen;

$R_1$, $R_2$, $R_3$, and $R_4$ are each independently hydrogen, halogen, hydroxyl, nitro, nitroso, cyano, isocyano, thiocyano, isothiocyano, aryl, alkyl, alkenyl, alkynyl, alkoxy, alkylthio, amino, monoalkylamino, dialkylamino, acyl, carbonyl, carboxyl, azide, sulfinyl, sulfonyl, sulfino, sulfo, or thiol; and $R_5$ is hydrogen, cyano, isocyano, aryl, alkyl, alkenyl, alkynyl, acyl, carbonyl, or carboxyl.

11. A method for modifying a protein or peptide having one or more glutamine residues, the method comprising:
performing a transglutaminase-catalyzed reaction between the protein or peptide and an amine-containing reagent, thereby producing a first derivative of the protein or peptide, wherein the reagent becomes covalently linked through its amine function to a side chain of at least one of said one or more glutamine residues; wherein the original protein or peptide, or a second derivative thereof, can be obtained by a treatment of the first derivative of the protein or peptide;
wherein the treatment comprises exposure to a physiological condition, altered pH, altered ionic strength, or elevated temperature;

wherein the amine-containing reagent is

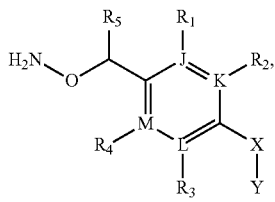
(III)

wherein:
X is oxygen, sulfur, nitrogen, phosphorous, or selenium;
Y is hydrogen, alkyl, dialkyl, acyl, sulfo, sulfonyl, sulfinyl, phospho, phosphonyl, hydroxyl, silyl, nitrosyl, thiol, sulfide, or oxo;
J, K, L, and M are each independently carbon or nitrogen;
$R_1$, $R_2$, $R_3$, and $R_4$ are each independently hydrogen, halogen, hydroxyl, nitro, nitroso, cyano, isocyano, thiocyano, isothiocyano, aryl, alkyl, alkenyl, alkynyl, alkoxy, alkylthio, amino, monoalkylamino, dialkylamino, acyl, carbonyl, carboxyl, azide, sulfinyl, sulfonyl, sulfino, sulfo, or thiol; and
$R_5$ is hydrogen, cyano, isocyano, aryl, alkyl, alkenyl, alkynyl, acyl, carbonyl, or carboxyl.

12. A method for modifying a protein or peptide having one or more glutamine residues, the method comprising:
performing a transglutaminase-catalyzed reaction between the protein or peptide and an amine-containing reagent, thereby producing a first derivative of the protein or peptide, wherein the reagent becomes covalently linked through its amine function to a side chain of at least one of said one or more glutamine residues; wherein the original protein or peptide, or a second derivative thereof, can be obtained by a treatment of the first derivative of the protein or peptide;
wherein the treatment comprises exposure to a physiological condition, altered pH, altered ionic strength, or elevated temperature;
wherein the amine-containing reagent is

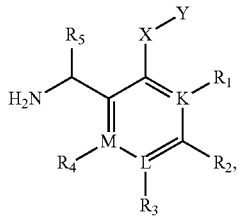
(IV)

wherein:
X is oxygen, sulfur, nitrogen, phosphorous, or selenium;
Y is hydrogen, alkyl, acyl, sulfo, or phospho;
J, K, L, and M are each independently carbon or nitrogen;
$R_1$, $R_2$, $R_3$, and $R_4$ are each independently hydrogen, halogen, hydroxyl, nitro, cyano, isocyano, thiocyano, isothiocyano, aryl, alkyl, alkenyl, alkynyl, alkoxy, alkylthio, amino, monoalkylamino, dialkylamino, acyl, carbonyl, carboxyl, azide, sulfinyl, sulfonyl, sulfino, sulfo, or thiol; and
$R_5$ is hydrogen, cyano, isocyano, aryl, alkyl, alkenyl, alkynyl, acyl, carbonyl, or carboxyl.

13. A method for modifying a protein or peptide having one or more glutamine residues, the method comprising:
performing a transglutaminase-catalyzed reaction between the protein or peptide and an amine-containing reagent, thereby producing a first derivative of the protein or peptide, wherein the reagent becomes covalently linked through its amine function to a side chain of at least one of said one or more glutamine residues; wherein the original protein or peptide, or a second derivative thereof, can be obtained by a treatment of the first derivative of the protein or peptide;
wherein the treatment comprises exposure to a physiological condition, altered pH, altered ionic strength, or elevated temperature;
wherein the amine-containing reagent is

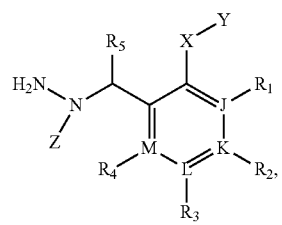
(V)

wherein
Z is alkyl, aryl, acyl, acyloxy, alkenyl, alkynyl, silyl, sulfo, sulfonyl, sulfinyl, phospho, phosphonyl, acyl, cyano, alkoxy, or nitroso;
X is oxygen, sulfur, nitrogen, phosphorous, or selenium;
Y is hydrogen, alkyl, dialkyl, acyl, sulfo, sulfonyl, sulfinyl, phospho, phosphonyl, hydroxyl, silyl, nitrosyl, thiol, sulfide, or oxo;
J, K, L, and M are each independently carbon or nitrogen;
$R_1$, $R_2$, $R_3$, and $R_4$ are each independently hydrogen, halogen, hydroxyl, nitro, nitroso, cyano, isocyano, thiocyano, isothiocyano, aryl, alkyl, alkenyl, alkynyl, alkoxy, alkylthio, amino, monoalkylamino, dialkylamino, acyl, carbonyl, carboxyl, azide, sulfinyl, sulfonyl, sulfino, sulfo, or thiol; and
$R_5$ is hydrogen, cyano, isocyano, aryl, alkyl, alkenyl, alkynyl, acyl, carbonyl, or carboxyl.

14. A method for modifying a protein or peptide having one or more glutamine residues, the method comprising:
performing a transglutaminase-catalyzed reaction between the protein or peptide and an amine-containing reagent, thereby producing a first derivative of the protein or peptide, wherein the reagent becomes covalently linked through its amine function to a side chain of at least one of said one or more glutamine residues; wherein the original protein or peptide, or a second derivative thereof, can be obtained by a treatment of the first derivative of the protein or peptide;
wherein the treatment comprises exposure to a physiological condition, altered pH, altered ionic strength, or elevated temperature;

wherein the amine-containing reagent is

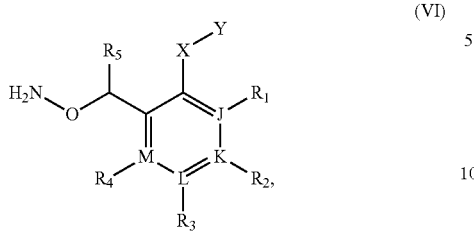

(VI)

wherein:
X is oxygen, sulfur, nitrogen, phosphorous, or selenium;
Y is hydrogen, alkyl, dialkyl, acyl, sulfo, sulfonyl, sulfinyl, phospho, phosphonyl, hydroxyl, silyl, nitrosyl, thiol, sulfide, or oxo;
J, K, L, and M are each independently carbon or nitrogen;
$R_1$, $R_2$, $R_3$, and $R_4$ are each independently hydrogen, halogen, hydroxyl, nitro, nitroso, cyano, isocyano, thiocyano, isothiocyano, aryl, alkyl, alkenyl, alkynyl, alkoxy, alkylthio, amino, monoalkylamino, dialkylamino, acyl, carbonyl, carboxyl, azide, sulfinyl, sulfonyl, sulfino, sulfo, thiol; and
$R_5$ is hydrogen, cyano, isocyano, aryl, alkyl, alkenyl, alkynyl, acyl, carbonyl, or carboxyl.

15. A method for modifying a protein or peptide having one or more glutamine residues, the method comprising:
performing a transglutaminase-catalyzed reaction between the protein or peptide and an amine-containing reagent, thereby producing a first derivative of the protein or peptide, wherein the reagent becomes covalently linked through its amine function to a side chain of at least one of said one or more glutamine residues; wherein the original protein or peptide, or a second derivative thereof, can be obtained by a treatment of the first derivative of the protein or peptide;
wherein the treatment comprises exposure to a physiological condition, altered pH, altered ionic strength, or elevated temperature;
wherein the amine-containing reagent is

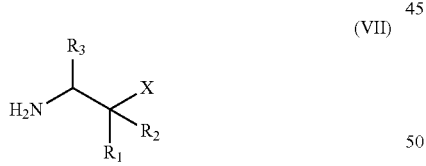

(VII)

wherein:
X is halogen, sulfonyl, sulfinyl, sulfoxo, cyano, isocyano, alkoxy, alkylthio, nitro, phospho, sulfo, or thiol;
$R_1$, and $R_2$ are each independently hydrogen, halogen, hydroxyl, nitro, cyano, isocyano, aryl, alkyl, alkenyl, alkynyl, alkoxy, alkylthio, amino, monoalkylamino, dialkylamino, acyl, carbonyl, carboxyl, azide, sulfinyl, sulfonyl, sulfino, sulfo, or thiol; and
$R_3$ is hydrogen, cyano, aryl, alkyl, alkenyl, alkynyl, acyl, carbonyl, or carboxyl.

16. A method for modifying a protein or peptide having one or more glutamine residues, the method comprising:
performing a transglutaminase-catalyzed reaction between the protein or peptide and an amine-containing reagent, thereby producing a first derivative of the protein or peptide, wherein the reagent becomes covalently linked through its amine function to a side chain of at least one of said one or more glutamine residues; wherein the original protein or peptide, or a second derivative thereof, can be obtained by a treatment of the first derivative of the protein or peptide;
wherein the treatment comprises exposure to a physiological condition, altered pH, altered ionic strength, or elevated temperature;
wherein the amine-containing reagent is

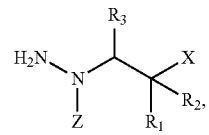

(VIII)

wherein:
Z is alkyl, aryl, acyl, acyloxy, alkenyl, alkynyl, silyl, sulfo, sulfonyl, sulfinyl, phospho, phosphonyl, acyl, cyano, alkoxy, or nitroso;
X is halogen, sulfonyl, sulfinyl, sulfo, sulfino, selenide, selenoxide, selenone, cyano, isocyano, alkoxy, alkylthio, nitro, amine oxide, phospho, or thiol;
$R_1$, and $R_2$ are each independently hydrogen, halogen, hydroxyl, nitro, cyano, isocyano, aryl, alkyl, alkenyl, alkynyl, alkoxy, alkylthio, amino, monoalkylamino, dialkylamino, acyl, carbonyl, carboxyl, azide, sulfinyl, sulfonyl, sulfino, sulfo, or thiol; and
$R_3$ is hydrogen, cyano, aryl, alkyl, alkenyl, alkynyl, acyl, carbonyl, or carboxyl.

17. A method for modifying a protein or peptide having one or more glutamine residues, the method comprising:
performing a transglutaminase-catalyzed reaction between the protein or peptide and an amine-containing reagent, thereby producing a first derivative of the protein or peptide, wherein the reagent becomes covalently linked through its amine function to a side chain of at least one of said one or more glutamine residues; wherein the original protein or peptide, or a second derivative thereof, can be obtained by a treatment of the first derivative of the protein or peptide;
wherein the treatment comprises exposure to a physiological condition, altered pH, altered ionic strength, or elevated temperature;
wherein the amine-containing reagent is

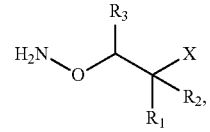

(IX)

wherein:
X is halogen, sulfonyl, sulfinyl, sulfo, sulfino, selenide, selenoxide, selenone, cyano, isocyano, alkoxy, alkylthio, nitro, amine oxide, phospho, or thiol;
$R_1$ and $R_2$ are each independently hydrogen, halogen, hydroxyl, nitro, cyano, isocyano, aryl, alkyl, alkenyl, alkynyl, alkoxy, alkylthio, amino, monoalkylamino, dialkylamino, acyl, carbonyl, carboxyl, azide, sulfinyl, sulfonyl, sulfino, sulfo, or thiol; and R₃ is hydrogen, cyano, aryl, alkyl, alkenyl, alkynyl, acyl, carbonyl, or carboxyl.

18. The method of claim 1, wherein a $^{15}$N label is introduced into or removed from said one or more glutamine residues.

19. The method of claim 1, wherein the treatment comprises photolysis of the first derivative.

20. The method of claim 1, wherein a protein is modified, and wherein the protein is an enzyme.

21. The method of claim 3, wherein a protein is modified, and wherein the protein is an enzyme.

22. The method of claim 4, wherein a protein is modified, and wherein the protein is an enzyme.

23. The method of claim 6, wherein a protein is modified, and wherein the protein is an enzyme.

24. The method of claim 7, wherein a protein is modified, and wherein the protein is an enzyme.

25. The method of claim 9, wherein a protein is modified, and wherein the protein is an enzyme.

26. The method of claim 10, wherein a protein is modified, and wherein the protein is an enzyme.

27. The method of claim 11, wherein a protein is modified, and wherein the protein is an enzyme.

28. The method of claim 12, wherein a protein is modified, and wherein the protein is an enzyme.

29. The method of claim 13, wherein a protein is modified, and wherein the protein is an enzyme.

30. The method of claim 14, wherein a protein is modified, and wherein the protein is an enzyme.

31. The method of claim 15, wherein a protein is modified, and wherein the protein is an enzyme.

32. The method of claim 16, wherein a protein is modified, and wherein the protein is an enzyme.

33. The method of claim 17, wherein a protein is modified, and wherein the protein is an enzyme.

* * * * *

SEQUENCE LISTING

```
<160> NUMBER OF SEQ ID NOS: 9

<210> SEQ ID NO 1
<211> LENGTH: 10
<212> TYPE: PRT
<213> ORGANISM: Bos taurus

<400> SEQUENCE: 1

Ala Val Pro Tyr Pro Gln Arg Asp Met Pro
1               5                   10

<210> SEQ ID NO 2
<211> LENGTH: 13
<212> TYPE: PRT
<213> ORGANISM: Bos taurus
```

-continued

```
<400> SEQUENCE: 2

Ala Val Pro Tyr Pro Gln Arg Asp Met Pro Ile Gln Ala
1               5                   10

<210> SEQ ID NO 3
<211> LENGTH: 13
<212> TYPE: PRT
<213> ORGANISM: Triticum aestivum

<400> SEQUENCE: 3

Leu Gly Gln Gln Gln Pro Phe Pro Pro Gln Gln Pro Tyr
1               5                   10

<210> SEQ ID NO 4
<211> LENGTH: 11
<212> TYPE: PRT
<213> ORGANISM: Human immunodeficiency virus

<400> SEQUENCE: 4

Tyr Gly Arg Lys Lys Arg Arg Gln Arg Arg Arg
1               5                   10

<210> SEQ ID NO 5
<211> LENGTH: 20
<212> TYPE: PRT
<213> ORGANISM: Escherichia coli

<400> SEQUENCE: 5

Phe Ser Asp Leu Val Gln Cys Gly Phe Pro Ser Pro Ala Ala Asp Tyr
1               5                   10                  15

Val Glu Gln Arg
            20

<210> SEQ ID NO 6
<211> LENGTH: 5
<212> TYPE: PRT
<213> ORGANISM: Artificial Sequence
<220> FEATURE:
<223> OTHER INFORMATION: Photocaging moiety

<400> SEQUENCE: 6

Gly Phe Asp Leu Ser
1               5

<210> SEQ ID NO 7
<211> LENGTH: 5
<212> TYPE: PRT
<213> ORGANISM: Artificial Sequence
<220> FEATURE:
<223> OTHER INFORMATION: Photocaging moiety

<400> SEQUENCE: 7

Gly Gly Gly Val Gly
1               5

<210> SEQ ID NO 8
<211> LENGTH: 10
<212> TYPE: PRT
<213> ORGANISM: Artificial Sequence
<220> FEATURE:
<223> OTHER INFORMATION: Photocaging moiety

<400> SEQUENCE: 8

Gly Phe Asp Leu Ser Gly Gly Gly Val Gly
```

```
1               5                   10

<210> SEQ ID NO 9
<211> LENGTH: 139
<212> TYPE: PRT
<213> ORGANISM: Escherichia coli

<400> SEQUENCE: 9

Met Leu Phe Ile Lys Pro Ala Asp Leu Arg Glu Ile Val Thr Phe Pro
1               5                   10                  15

Leu Phe Ser Asp Leu Val Gln Cys Gly Phe Pro Ser Pro Ala Ala Asp
            20                  25                  30

Tyr Val Glu Gln Arg Ile Asp Leu Asn Gln Leu Leu Ile Gln His Pro
        35                  40                  45

Ser Ala Thr Tyr Phe Val Lys Ala Ser Gly Asp Ser Met Ile Asp Gly
    50                  55                  60

Gly Ile Ser Asp Gly Asp Leu Leu Ile Val Asp Ser Ala Ile Thr Ala
65                  70                  75                  80

Ser His Gly Asp Ile Val Ile Ala Ala Val Asp Gly Glu Phe Thr Val
                85                  90                  95

Lys Lys Leu Gln Leu Arg Pro Thr Val Gln Leu Ile Pro Met Asn Ser
            100                 105                 110

Ala Tyr Ser Pro Ile Thr Ile Ser Ser Glu Asp Thr Leu Asp Val Phe
        115                 120                 125

Gly Val Val Ile His Val Val Lys Ala Met Arg
    130                 135
```